US008480716B2

United States Patent
Perrow et al.

(10) Patent No.: US 8,480,716 B2
(45) Date of Patent: Jul. 9, 2013

(54) BONE PLATE SYSTEM

(75) Inventors: Scott J. Perrow, Ishpeming, MI (US); Brad Fredin, Negaunee, MI (US)

(73) Assignee: Pioneer Surgical Technology, Inc., Marquette, MI (US)

( * ) Notice: Subject to any disclaimer, the term of this patent is extended or adjusted under 35 U.S.C. 154(b) by 766 days.

(21) Appl. No.: 12/429,934

(22) Filed: Apr. 24, 2009

(65) Prior Publication Data

US 2009/0270927 A1    Oct. 29, 2009

Related U.S. Application Data

(60) Provisional application No. 61/047,926, filed on Apr. 25, 2008.

(51) Int. Cl.
*A61B 17/80*               (2006.01)
(52) U.S. Cl.
USPC ........... 606/286; 606/290; 606/289; 606/280; 606/291
(58) Field of Classification Search
USPC ................... 606/70–71, 53, 62–68, 279–299, 606/300–308; 411/85, 95, 96, 97, 342, 349, 411/552, 553, 352, 353, 371.1, 371.2
See application file for complete search history.

(56) References Cited

U.S. PATENT DOCUMENTS

| | | | |
|---|---|---|---|
| 4,484,570 A | 11/1984 | Sutter et al. | |
| 5,057,111 A | 10/1991 | Park | |
| 5,520,690 A | 5/1996 | Errico et al. | |
| 5,531,746 A | 7/1996 | Errico et al. | |
| 5,607,426 A * | 3/1997 | Ralph et al. | 606/287 |
| 5,681,311 A | 10/1997 | Foley et al. | |
| 5,713,900 A | 2/1998 | Benzel et al. | |
| 5,735,853 A | 4/1998 | Olerud | |
| 5,800,433 A | 9/1998 | Benzel et al. | |
| 5,843,082 A | 12/1998 | Yuan et al. | |
| 5,904,683 A | 5/1999 | Pohndorf et al. | |
| 5,954,722 A | 9/1999 | Bono | |
| 6,030,389 A | 2/2000 | Wagner et al. | |
| 6,036,693 A | 3/2000 | Yuan et al. | |
| 6,117,173 A | 9/2000 | Taddia et al. | |

(Continued)

FOREIGN PATENT DOCUMENTS

| | | | |
|---|---|---|---|
| DE | 10226496 | * | 6/2001 |
| WO | 8803781 | | 6/1988 |

(Continued)

*Primary Examiner* — Sameh Boles
*Assistant Examiner* — Samuel Hanna
(74) *Attorney, Agent, or Firm* — Fitch, Even, Tabin & Flannery LLP

(57) ABSTRACT

A bone plate system is provided that includes bone plates and bone anchor assemblies for being inserted into bone plate bores to secure the bone plates to one or more bones. In one aspect, the bone plate system includes a bone anchor assembly having a locking cap and a locking fastener connected to a head portion of a bone anchor. The bone anchor assembly is driven into a bone plate bore before the locking fastener is shifted to expand the locking cap and fix the bone anchor assembly within the bore. In another aspect, the bone plate system includes a bone anchor assembly having a locking cap that deflects radially inward due to contact with the bone plate at large bone anchor assembly insertion angles. In addition, a bone anchor assembly having a preassembled condition with a locking cap resisting back out of a locking fastener.

18 Claims, 44 Drawing Sheets

U.S. PATENT DOCUMENTS

| | | |
|---|---|---|
| 6,193,720 B1 | 2/2001 | Yuan et al. |
| 6,214,005 B1 | 4/2001 | Benzel et al. |
| 6,228,085 B1 * | 5/2001 | Theken et al. ............... 606/289 |
| 6,235,033 B1 | 5/2001 | Brace et al. |
| 6,241,731 B1 | 6/2001 | Fiz |
| 6,306,136 B1 | 10/2001 | Baccelli |
| 6,331,179 B1 | 12/2001 | Freid et al. |
| 6,342,055 B1 | 1/2002 | Eisermann et al. |
| 6,454,769 B2 | 9/2002 | Wagner et al. |
| 6,575,975 B2 | 6/2003 | Brace et al. |
| 6,579,290 B1 | 6/2003 | Hardcastle et al. |
| 6,595,993 B2 | 7/2003 | Donno et al. |
| 6,669,697 B1 | 12/2003 | Pisharodi |
| 6,679,883 B2 | 1/2004 | Hawkes et al. |
| 6,740,088 B1 | 5/2004 | Kozak et al. |
| 6,793,658 B2 | 9/2004 | LeHuec et al. |
| 6,884,242 B2 | 4/2005 | LeHuec et al. |
| 6,890,334 B2 | 5/2005 | Brace et al. |
| 6,964,664 B2 | 11/2005 | Freid et al. |
| 7,048,739 B2 | 5/2006 | Konieczynski et al. |
| 7,264,621 B2 | 9/2007 | Coates et al. |
| 7,273,481 B2 | 9/2007 | Lombardo et al. |
| 7,981,142 B2 * | 7/2011 | Konieczynski et al. ...... 606/290 |
| 2001/0021851 A1 | 9/2001 | Eberlein et al. |
| 2001/0037112 A1 * | 11/2001 | Brace et al. .................. 606/69 |
| 2002/0016595 A1 | 2/2002 | Michelson |
| 2002/0022843 A1 | 2/2002 | Michelson |
| 2002/0058939 A1 | 5/2002 | Wagner et al. |
| 2002/0128655 A1 | 9/2002 | Michelson |
| 2003/0208204 A1 | 11/2003 | Bailey et al. |
| 2004/0127897 A1 | 7/2004 | Freid et al. |
| 2004/0127900 A1 * | 7/2004 | Konieczynski et al. ........ 606/69 |
| 2004/0153069 A1 | 8/2004 | Paul |
| 2004/0204712 A1 | 10/2004 | Kolb et al. |
| 2004/0210221 A1 | 10/2004 | Kozak et al. |
| 2005/0027293 A1 | 2/2005 | LeHuec et al. |
| 2005/0033298 A1 | 2/2005 | Hawkes et al. |
| 2005/0234456 A1 | 10/2005 | Malandain |
| 2005/0251137 A1 | 11/2005 | Ball |
| 2005/0273105 A1 | 12/2005 | Konieczynski et al. |
| 2006/0041260 A1 | 2/2006 | Orbay |
| 2006/0079900 A1 | 4/2006 | Mathieu et al. |
| 2006/0122602 A1 | 6/2006 | Konieczynski et al. |
| 2006/0122604 A1 * | 6/2006 | Gorhan et al. .................. 606/69 |
| 2006/0149256 A1 | 7/2006 | Wagner et al. |
| 2006/0161157 A1 | 7/2006 | Mosca et al. |
| 2006/0200147 A1 | 9/2006 | Ensign et al. |
| 2006/0235399 A1 | 10/2006 | Carls et al. |
| 2006/0235411 A1 | 10/2006 | Blain et al. |
| 2006/0241616 A1 | 10/2006 | Konieczynski |
| 2007/0093838 A1 | 4/2007 | Khodadadyan-Klostermann et al. |
| 2007/0123879 A1 | 5/2007 | Songer et al. |
| 2007/0225717 A1 | 9/2007 | Hawkes |
| 2008/0009870 A1 | 1/2008 | Lombardo et al. |
| 2008/0015597 A1 | 1/2008 | Whipple |
| 2008/0114359 A1 | 5/2008 | Murner et al. |
| 2008/0172094 A1 * | 7/2008 | Mathieu et al. ............... 606/280 |
| 2008/0177330 A1 * | 7/2008 | Ralph et al. .................. 606/290 |
| 2008/0243192 A1 | 10/2008 | Jacene et al. |
| 2009/0036933 A1 | 2/2009 | Dube et al. |

FOREIGN PATENT DOCUMENTS

| | | |
|---|---|---|
| WO | 9608206 | 3/1996 |
| WO | 9722306 | 6/1997 |
| WO | 9834553 | 8/1998 |
| WO | 0066011 | 11/2000 |
| WO | 0149191 | 7/2001 |

* cited by examiner

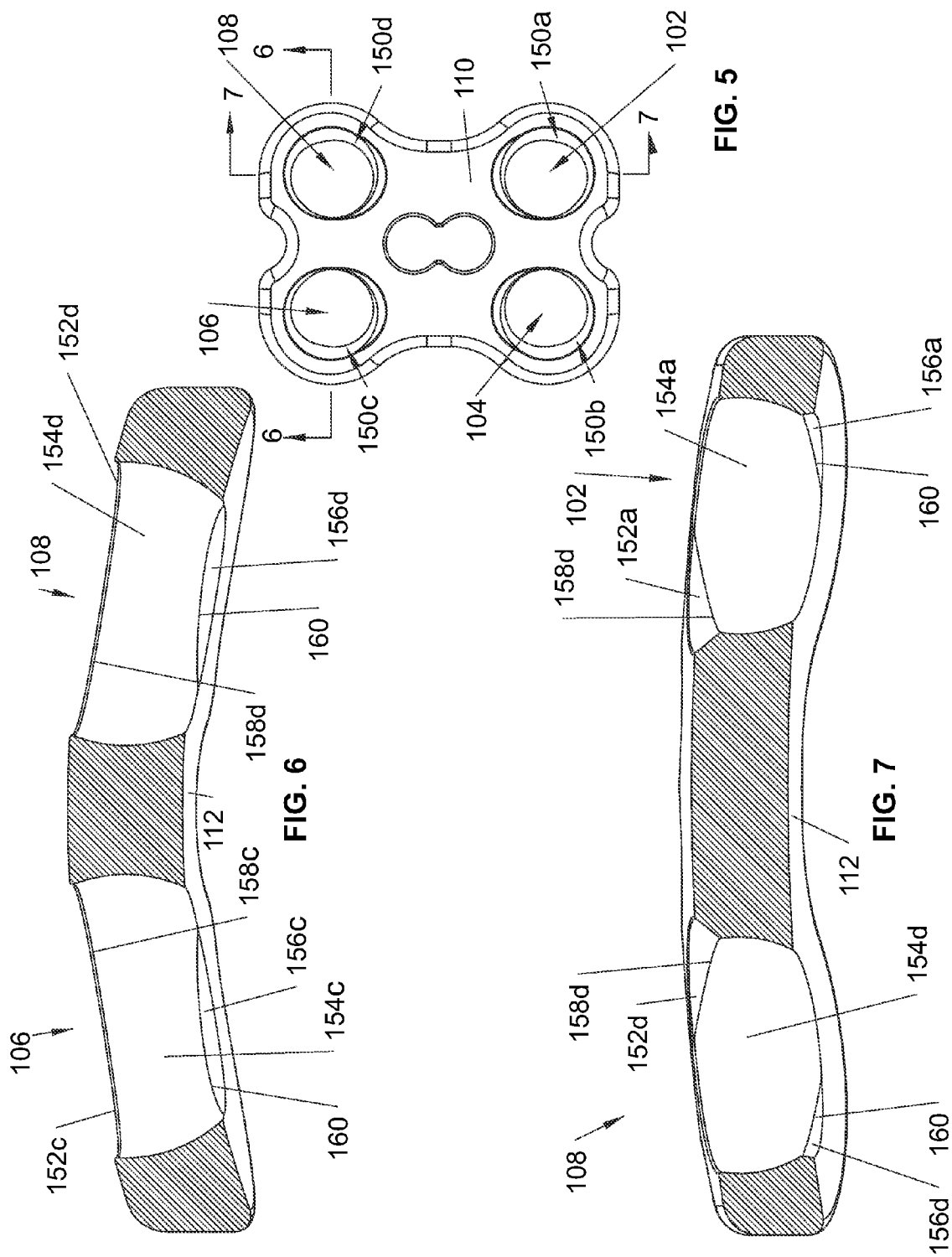

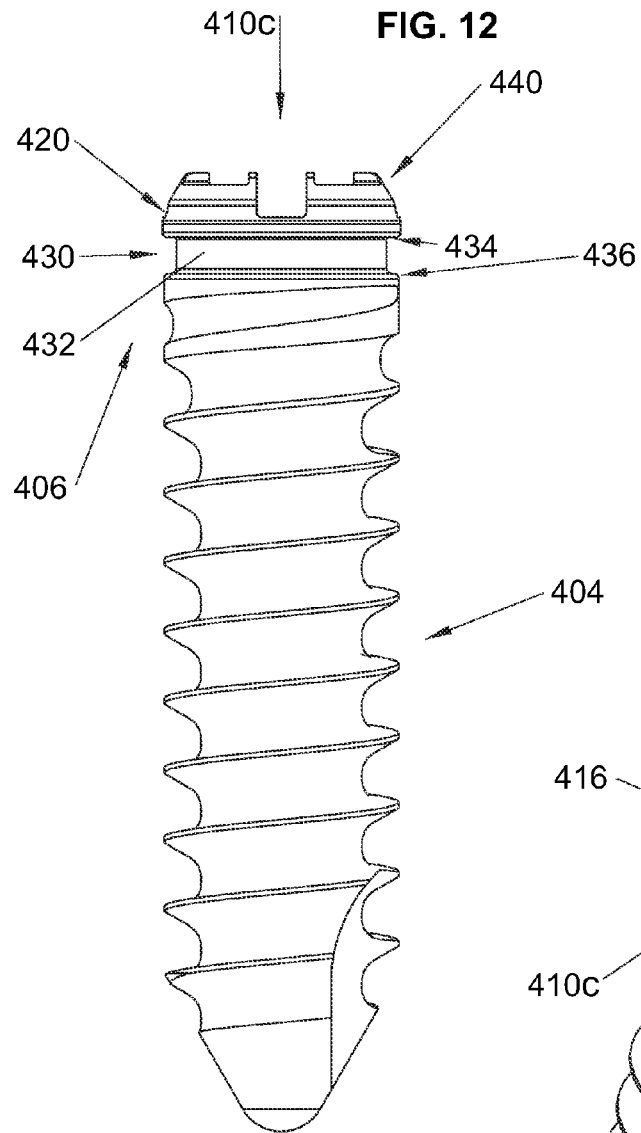
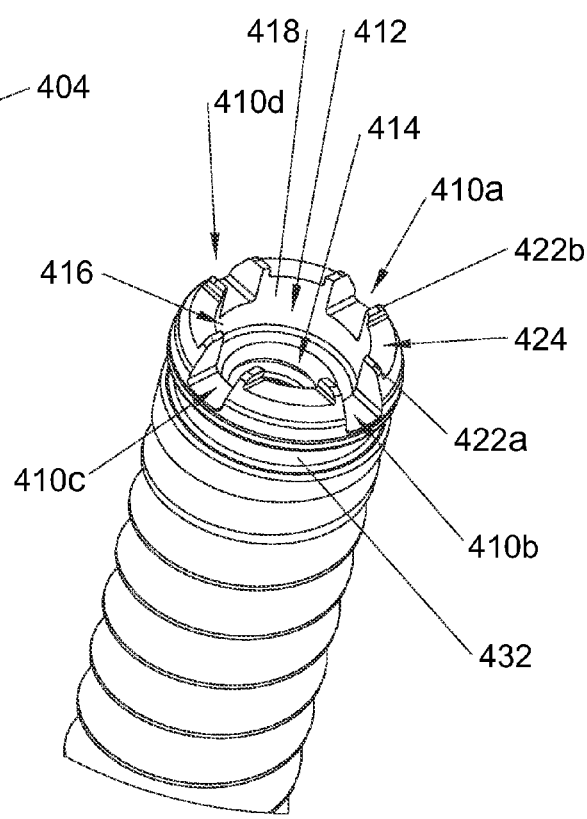
FIG. 12
FIG. 11

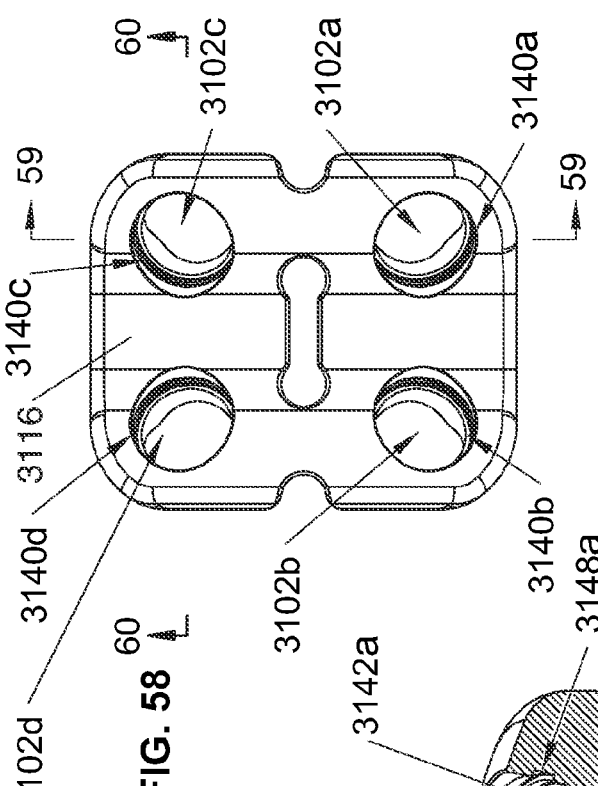
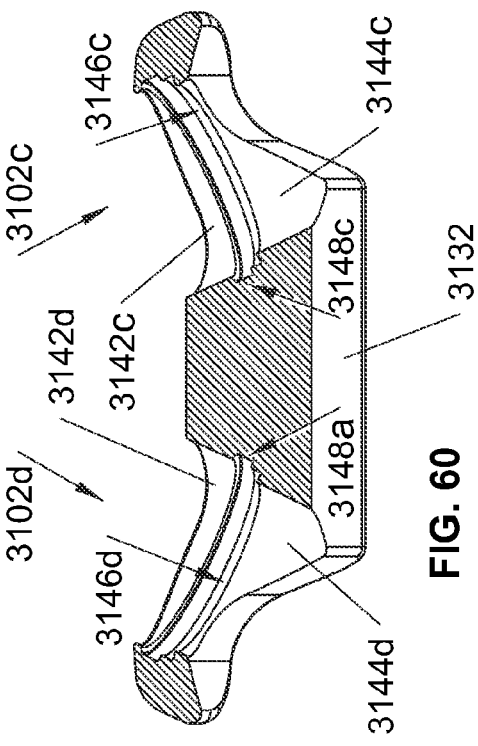
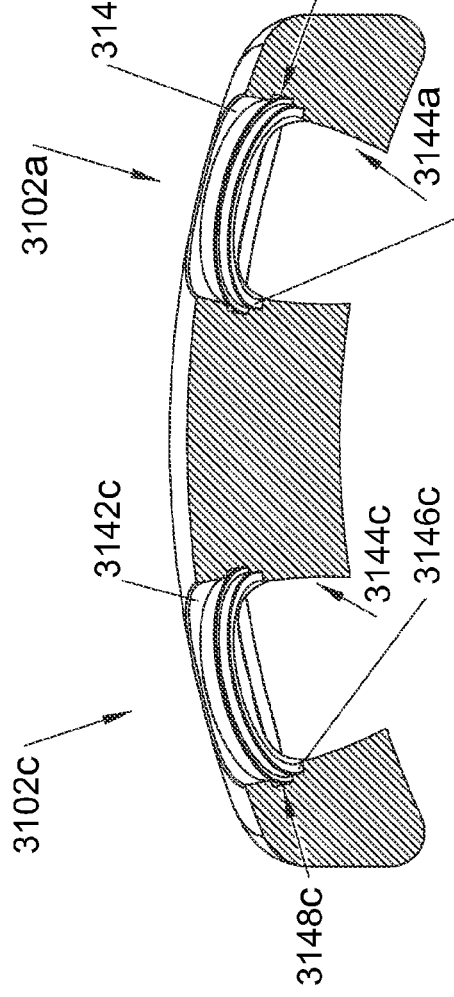
FIG. 58
FIG. 59
FIG. 60

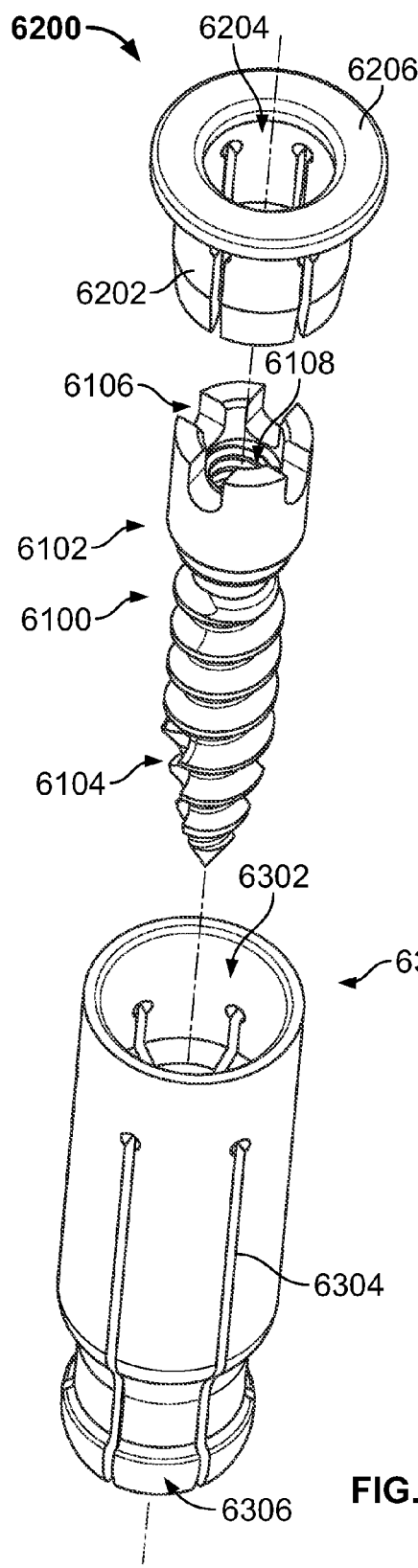
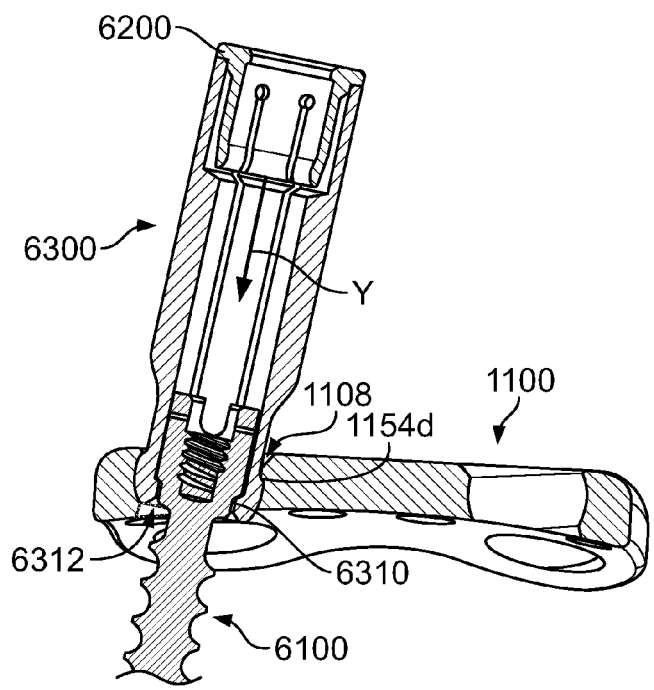
FIG. 71
FIG. 70

BONE PLATE SYSTEM

CROSS-REFERENCE TO RELATED APPLICATIONS

This application claims the benefit of U.S. Provisional Application Ser. No. 61/047,926, filed Apr. 25, 2008, which is hereby incorporated by reference as if fully set forth herein.

FIELD OF THE INVENTION

The invention relates to a bone plate system and, more particularly, to a bone plate system that allows for polyaxial bone anchor insertion and rigid fixation of the bone anchor relative to a bone plate.

BACKGROUND OF THE INVENTION

There are presently many different types of plate and fixture systems for securing two or more bones or bone fragments in relative position so that the bones may fuse or heal, or so that tissue adjacent the bones may heal without disruption from the movement of the secured bones. As used herein, the term bone may refer to a bone, or a bone fragment or portion, and the term may refer to a portion of a bone that is covered with another material, such as the endplates covering the top and bottom surface of a vertebra. Also as used herein, the term fusion refers to the joining of materials, such as bone or graft material, and the fusion site is the entire region in which fusion may be desired. As is apparent, bone plate systems may be used to fuse a variety of different types of bone, including spinal vertebrae.

The bones and connective tissues of a normal human spinal column include vertebrae that support the weight of the human body as well as protect the spinal cord and other elements of the nervous system. A typical vertebra consists of a vertebral body and a vertebral arch positioned posterior to the vertebral body. The vertebral body is generally aligned with the vertebral bodies of the adjacent vertebrae to transmit loading forces along the spinal column. The vertebral arch, on the other hand, is formed by a pair of pedicles and a pair of laminae that surround and protect the spinal cord.

The vertebrae of the spine are classified into five regions based on their position along the spinal column: cervical, thoracic, lumbar, sacral, and coccygeal (tail bone). The cervical region contains seven small vertebrae located near the neck and base of the skull, while the thoracic region contains twelve larger vertebrae near the rib cage that increase in size going downward along the spine. The lumbar region is generally in the lower back area and has five vertebrae that are larger than the other vertebrae in the spinal column in order to support the full weight of the upper torso. Normally, the cervical, thoracic, and lumbar vertebrae have intervertebral discs positioned between adjacent vertebral bodies that allow slight movement of the vertebrae and dampen jarring forces which act on the vertebrae.

The sacral and coccygeal vertebrae, on the other hand, are fused in maturity and lack intervertebral discs. More specifically, the sacral region consists of five vertebrae fused together to form the sacrum, a large triangular bone positioned between the hip bones. The sacrum is relatively concave and faces inward to the body such that the first sacral vertebra (S1) extends obliquely relative to the last lumbar vertebra (L5). Additionally, the anterior-most point of the S1 vertebra includes a formation referred to as the sacral promontory positioned adjacent the intervertebral disc located between the S1 and L5 vertebrae.

Various types of injury or deformity may affect the structure and function of the spinal column. For example, sudden trauma may break bones or tear soft tissues which support the spine. Alternatively, genetic disorders, tumors, or infections may cause bones to deteriorate. Further, excessive movement of one vertebral body relative to another may cause compression of the spinal cord or nerves. Patients who suffer from one or more of these conditions often experience extreme and debilitating pain, and may incur permanent neurologic damage if the conditions are not properly treated.

One technique for treating a number of spinal disorders is known as interbody spinal fusion. This procedure involves removing an intervertebral disc and replacing it with a bone graft in conjunction with stabilizing the vertebrae on either side of the intervertebral disc. The vertebrae eventually fuse together by growth of the bone across the disc space which rigidly connects the vertebrae. The stabilization of the vertebrae is often assisted by a surgically implanted bone plate and anchor system that holds the vertebral bodies in proper alignment and allows the bones to heal. Such techniques have been successfully used to reduce pain and restore the structural integrity of the affected bones.

Different applications of the bone plate may present different requirements for bone plate systems. For example, in some instances it may be desirable to utilize a bone plate system that limits post-operative subsidence of the vertebrae. More specifically, vertebrae may require a higher level of strength and stability to ensure fusion of the affected vertebrae. A bone plate system applied to the vertebrae under these conditions may rigidly fix the bone plate system and the affected vertebrae in the desired orientation to provide the required biomechanical stability while fusion is achieved.

In some instances, it is also highly desirable for a bone plate system to provide a bone anchor that may be driven into bone at a variety of different insertion angles. This functionality provides a surgeon with the flexibility to respond to anticipated or unanticipated features of the subject anatomy. Further, the ability to polyaxially drive the bone anchor into a vertebra also permits the surgeon to angle the bone anchor away from the end plates of the vertebral body. Engaging the bone anchor with the end plate in some instances is undesirable as the bone anchor may cause a weakened end plate to fracture or otherwise reduce the end plate's load bearing capacity.

Many prior bone plate systems fail to provide the desired functionality and ease of use required by a number of bone fusion procedures. One such shortcoming is that many bone plate systems fail to resist backing out or loosening of the bone anchors, which are often bone screws. If the bone screws loosen, the bones are not properly secured and may be allowed to move relative to one another in an uncontrolled manner. This may compromise the ability to achieve optimal bone fusion and bone alignment, and it may lead to loss of graft material and damage or loss of bone. Furthermore, when the plate is located in the lumbar or sacral regions of the spinal column with heavy loading and movement of the vertebrae, these issues may be further compounded or exacerbated. Additionally, in the case of anterior lumbar or anterior sacral plates, a bone screw backing out could cause irritation or a puncture wound to internal organs, or even damage to the circulatory or nervous systems.

Some prior bone plate systems seek to provide polyaxial insertion and fixation of a bone screw using a set screw that expands the bone screw head. In these systems, the bone screw is passed through a bore formed in a bone plate until the bone screw head is positioned within the bore. The set screw is inserted into the bone screw head to expand the head until the head presses against the walls of the bore such that the bone screw is held in place within the bore by the expanded head. However, to permit the bone screw head to expand, the head is constructed to be flexible for this purpose. For example, in U.S. Pat. No. 6,575,975 to Brace et al., the bone screw head is weakened by removing material which permits portions of the head to flex outwardly. When the bone plate is located in the lumbar or sacral region of the spinal column, this approach is undesirable because weakening the bone screw head may cause the head material to yield or otherwise deform when subjected to loading of the vertebra. Failure or deformation of the bone screw head may also compromise the stability of the bone plate system which, in turn, could cause the bone fusion procedure to fail. Another problem with these configurations is that the stress on the system may lead to the set screw backing out over time.

Other bone plate systems fix a bone screw within the bore of a bone plate using an annular bushing located within the bore before the bone screw is inserted therethrough. The bone screw is then inserted through an opening in the bushing until the bone screw head is positioned within the bushing. The bone screw head may have an outer profile that causes the bushing to expand into tight engagement with the bore surface. In prior bone plates, the movement of the bushing is limited to the confines of the bore in which the bushing is received. As is apparent, the angle at which the bone screw is inserted through the bore and into a bone is similarly limited by the limited movement of the bushing within the bone plate bore. Further, the insertion angle of the bone screw may also be limited by contact between the bone screw and the bone plate as the bone screw is driven into the bone plate bore. Specifically, the bone screw head may catch on the upper lip of the bone plate extending about the bore and resist passage into the bore, such that a different insertion angle may be required.

One problem with bushings that are placed into bone plate bores is the assembly time this requires. Another problem with this arrangement is that the surgeon has to align the bone screw with the opening in the bushing before passing the bone screw therethrough. This complicates the process of fastening the bone plate onto the bones and increases the duration of the surgical procedure. In addition, one approach as disclosed in U.S. Pat. No. 6,030,389 to Wagner et al. involves a separate step of screwing a set screw into an anchor head to expand the bone anchor head and fix the anchor relative to the bone plate. The set screw is necessarily larger than the bone anchor head in order to expand a bushing positioned within the bore. Not only does the large set screw require time-intensive installation, but it also extends a significant distance above the head of the bone anchor such that a thicker bone plate is required to limit the distance the set screw projects into the body.

SUMMARY OF THE INVENTION

In one aspect of the invention, a bone plate system is provided which includes a bone plate and a through bore having an annular surface extending about the through bore. The bone plate system also includes a bone anchor for extending through the bone plate bore and driving into a bone, the bone anchor having upper and lower ends and a longitudinal axis extending therebetween. The bone anchor has a rigid upper head portion with a central axial bore including an enlarged diameter upper opening portion thereof that opens to the bone anchor upper end and extends axially downward therefrom. The bone plate system also includes a locking cap carried on the anchor head portion and a locking fastener configured to be inserted into the bone anchor opening. The locking fastener shifts the locking cap into tight engagement with the through bore annular surface to keep the anchor fixed relative to the bone plate. Additionally, an upper head portion of the locking fastener is configured for driving the locking fastener into the axial bore of the bone anchor and is sized to be received in the upper opening portion of the bone anchor bore.

With respect to the locking cap, an annular wall portion of the locking cap extends axially along the bone anchor longitudinal axis and about the bone anchor head portion when the locking cap is carried on the anchor head portion. The annular wall portion includes a radially outer upper end portion configured to engage the bore annular surface and a radially inner lower end portion for engaging the bone anchor. The locking cap also includes a radially inner upper cam surface of the locking cap that cooperates with the locking fastener. As the locking fastener is inserted in the bone anchor opening, the locking fastener cams against the locking cap to deflect the annular wall portion. In this manner, the radially outer upper end portion shifts radially outward into tight engagement with the bore annular surface while the radially inner lower end portion shifts radially inward into tight engagement with the bone anchor.

In another form of the present invention, a bone plate system is provided including a bone plate having a through bore and a central axis extending therethrough. The bone plate system also includes an elongate bone anchor having a longitudinal axis with the bone anchor being configured for polyaxial insertion through the bone plate bore. The bone anchor includes an upper head portion that carries a locking cap and is configured to be received within the bone plate bore. The locking cap has an annular wall portion of the locking cap that extends axially along the bone anchor longitudinal axis and about the bone anchor upper head portion. The locking cap also has a plurality of projections that extend radially inward from the annular wall portion. A set screw is threadingly engaged to the anchor head portion and has a narrow portion that is aligned with the locking cap projections when the set screw is threadingly engaged to the anchor head portion at a predetermined axial position. Further, the set screw narrow portion is spaced from radially inner ends of the locking cap projections when the set screw is in the predetermined axial position. The spacing between the projection inner ends and the set screw permits the projections to shift radially inward due to contact of the locking cap annular wall portion with the bone plate during insertion of the bone anchor through the through bore. This way, the bone anchor may be inserted into the through bore at large angles between the bone anchor longitudinal axis and the bore central axis without the annular wall portion getting caught on the bone plate.

In another aspect of the invention, a bone anchor assembly is provided including an elongate bone anchor having a head portion and a locking cap carried on the anchor head portion. The locking cap has a plurality of projections extending over the anchor head portion that have substantially flat lower surfaces which face the anchor head portion. The bone anchor assembly also includes a locking fastener having an annular collar portion that is received within the anchor head portion. Cooperating cam surfaces of the locking cap projections and the locking fastener collar portion shift the locking cap projections radially outward as the locking fastener is driven into the anchor head portion. Further, the annular collar portion of the locking fastener has a substantially flat upper surface that is arranged below and in overlapping confronting relation with the substantially flat lower surfaces of the locking cap projections when the annular collar is advanced axially beyond the locking cap projections. In this way, the flat confronting surfaces of the annular collar portion and the locking cap projections resist locking fastener back out and maintain the anchor, locking cap, and locking fastener in a preassembled configuration.

A method of producing a bone anchor assembly is also provided and includes passing an open end of a locking cap over a head portion of a bone anchor and engaging surfaces of the locking cap and anchor head portion to retain the locking cap on the anchor head portion. The method also includes connecting a fastener to the bone anchor and passing an annular collar of the fastener beyond projections of the locking cap such that the projections retain the fastener on the anchor head. In this form, the bone anchor is ready to be driven through a bone plate bore and into a bone.

BRIEF DESCRIPTION OF THE DRAWINGS

FIG. 5 is a plan view of the bone plate;

FIG. 6 is a cross sectional view taken across line 6-6 of FIG. 5 showing annular surfaces of the bone plate through bores;

FIG. 7 is a cross sectional view taken across line 7-7 of FIG. 5 showing upper and lower chamfered surfaces of the bone plate through bores;

FIG. 11 is a perspective view of the bone anchor of FIG. 8 showing an upwardly opening bore extending axially downward through the upper head portion of the bone anchor;

FIG. 12 is a side elevational view of the bone anchor of FIG. 8 showing an annular channel formed in the bone anchor head portion;

FIG. 58 is a plan view of the bone plate of FIG. 54 showing sidewalls of the bone plate through bores;

FIG. 59 is a cross-sectional view taken along line 59-59 in FIG. 58 showing a plurality of surfaces that interact with the bone anchor assembly;

FIG. 60 is a cross-sectional view taken along line 60-60 in FIG. 58 showing lower bore surfaces that cooperate with a cylindrical outer surface of the respective bone anchor assembly;

FIG. 70 is a schematic view of a threaded pin, pin cap, and a pin centering tip showing the assembly thereof; and FIG. 71 is a cross-sectional view of the threaded pin, pin cap, and pin centering tip of FIG. 70 showing the threaded pin driven from the pin cap along the interior of the pin centering tip and into engagement with a bone plate.

DETAILED DESCRIPTION OF THE PREFERRED EMBODIMENTS

Figure 1:
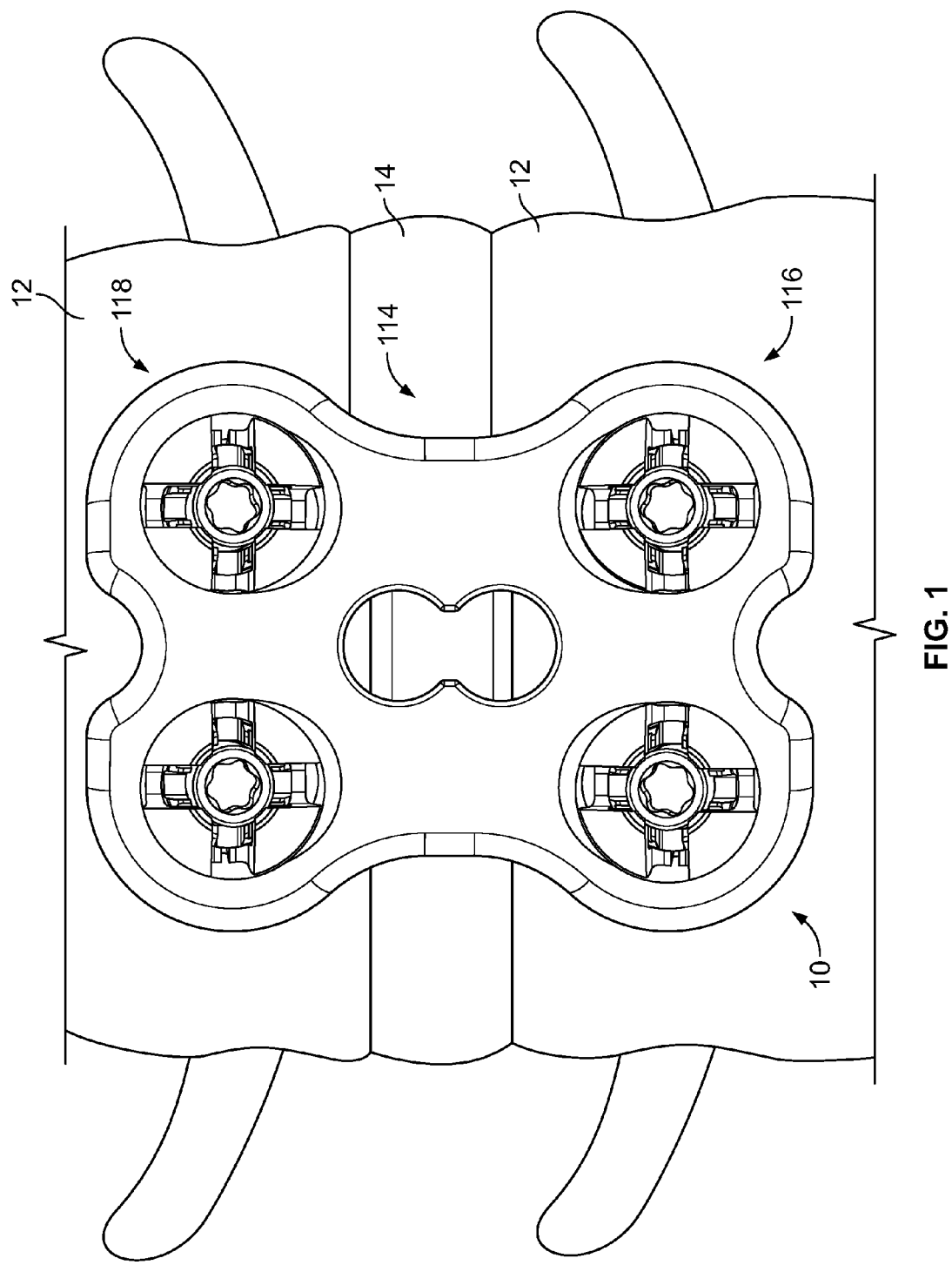
FIG. 1 is a plan view of a bone plate system in accordance with the present invention showing a bone plate fastened to vertebral bones.

Referring initially to FIG. 1, a bone plate system 10 is depicted shown connected on the anterior surface of adjacent lumbar vertebrae 12 that are spaced by an intervertebral disc 14. In general, the bone plate system 10 may be used to secure one or more bones in a desired spatial relationship to aid in their healing. The bone plate system 10 may also be used to assist in the healing necessary after trauma or degenerative disorders have affected the intervertebral disc 14. Furthermore, the bone plate system 10 may be used to correct and/or relieve a variety of spinal disorders, including but not limited to degenerative disorders, disorders induced by trauma, and pinched nerves.

Figure 2:
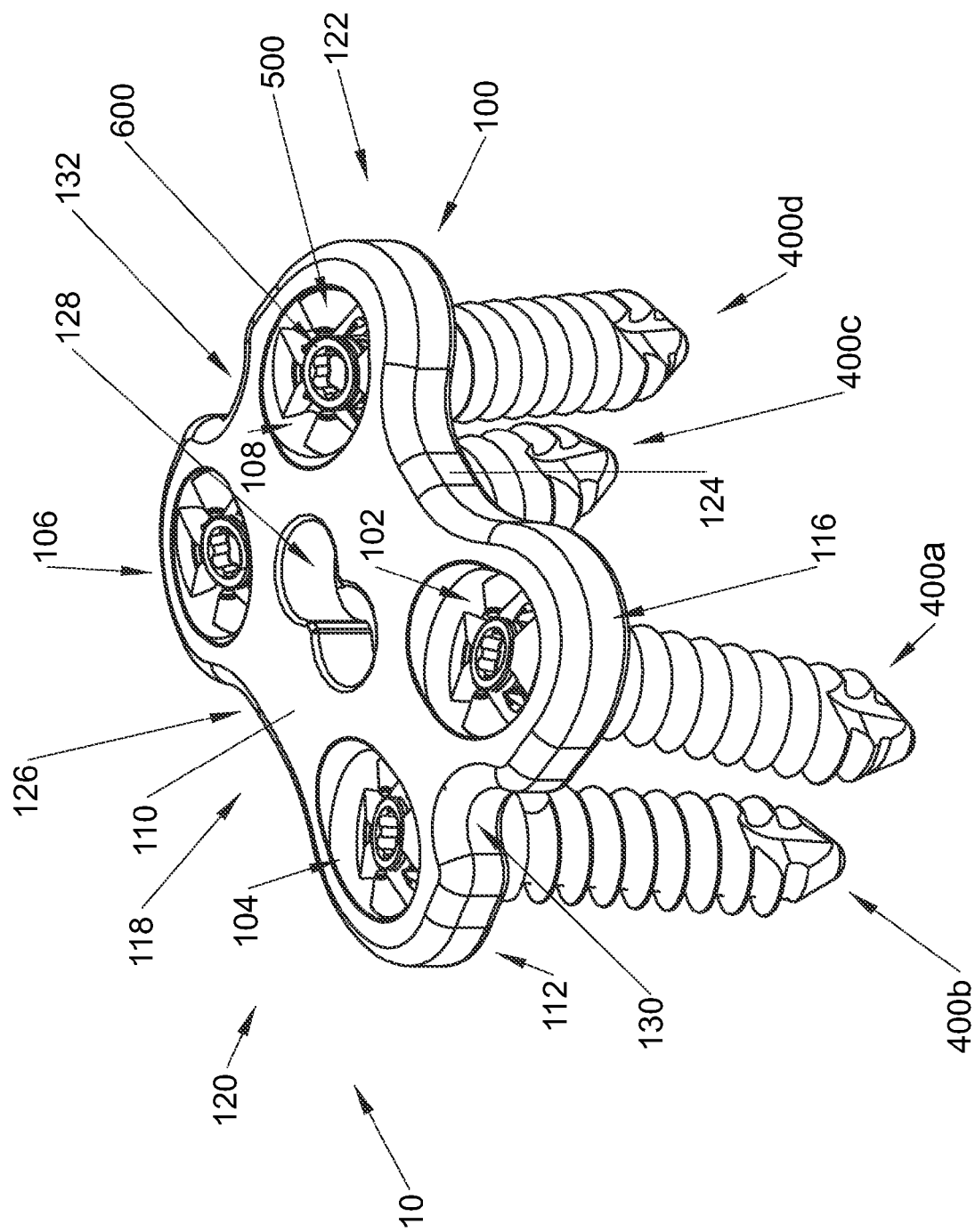
FIG. 2 is a perspective view of the bone plate system showing the bone plate and bone anchor assemblies received in through bores of the bone plate.

Turning to FIG. 2, the bone plate system 10 is shown having a bone plate 100 and bone anchor assemblies 400a-400d. The bone plate 100 is generally configured to be placed on one or more bones before bone anchor assemblies 400 are inserted into through bores 102, 104, 106, 108 which extend between upper and lower surfaces 110, 112 of the bone plate 100. More specifically, bone system 10 permits a bone anchor assembly 400 to be polyaxially inserted into one of the bores 102, 104, 106, and 108 at a range of angles relative to the bone plate 100. In this manner, a surgeon may drive the bone anchor assembly through a bore of the bone plate 100 and into an underlying bone at a predetermined angle. Once the bone anchor assembly 400 is positioned within the bone anchor bore, a locking fastener 600 of the bone anchor assembly 400 is axially shifted to expand a locking cap 500 and fix the bone anchor assembly 400 within the bore.

An outer sidewall 116 extends around the periphery of the bone plate 100 and generally extends between the upper surface 110 and lower surface 112. The bone plate 100 has a generally dog-bone shape with a narrow middle portion 118 and enlarged opposing ends 120, 122. The dog-bone shape reduces the overall footprint of the bone plate system 10 on the bone and provides sidewall portions 124, 126 that may be more easily grasped with surgical tools as needed during surgery.

The bone plate 100 has several features which improve the ease with which the bone plate 100 may be installed onto vertebrae 12. First, the bone plate 100 has double-lobed tool slot 128 for receiving a plate insertion tool (not pictured). In a preferred embodiment, the tool slot 128 is configured to receive an expanding tip of the plate insertion tool which temporarily holds the bone plate 100 on the plate insertion tool. The bone plate 100 may then be positioned onto one or more bones, such as the vertebrae 12, using the plate insertion tool and secured to the vertebrae 12 by way of bone anchor assemblies 400.

Second, the bone plate 100 has notches 130, 132 formed by arcuate depressions in sidewall 116. The notches 130, 132 are sized to accept temporary holding pins (not shown) that hold the bone plate 100 onto one or more bones. For example, once the bone plate 100 has been positioned on the vertebrae 12, a temporary holding pin, such as a push pin, is placed in close abutting relation to both notches 130, 132 to temporarily secure the bone plate 100 to the vertebrae 12.

Figure 3:
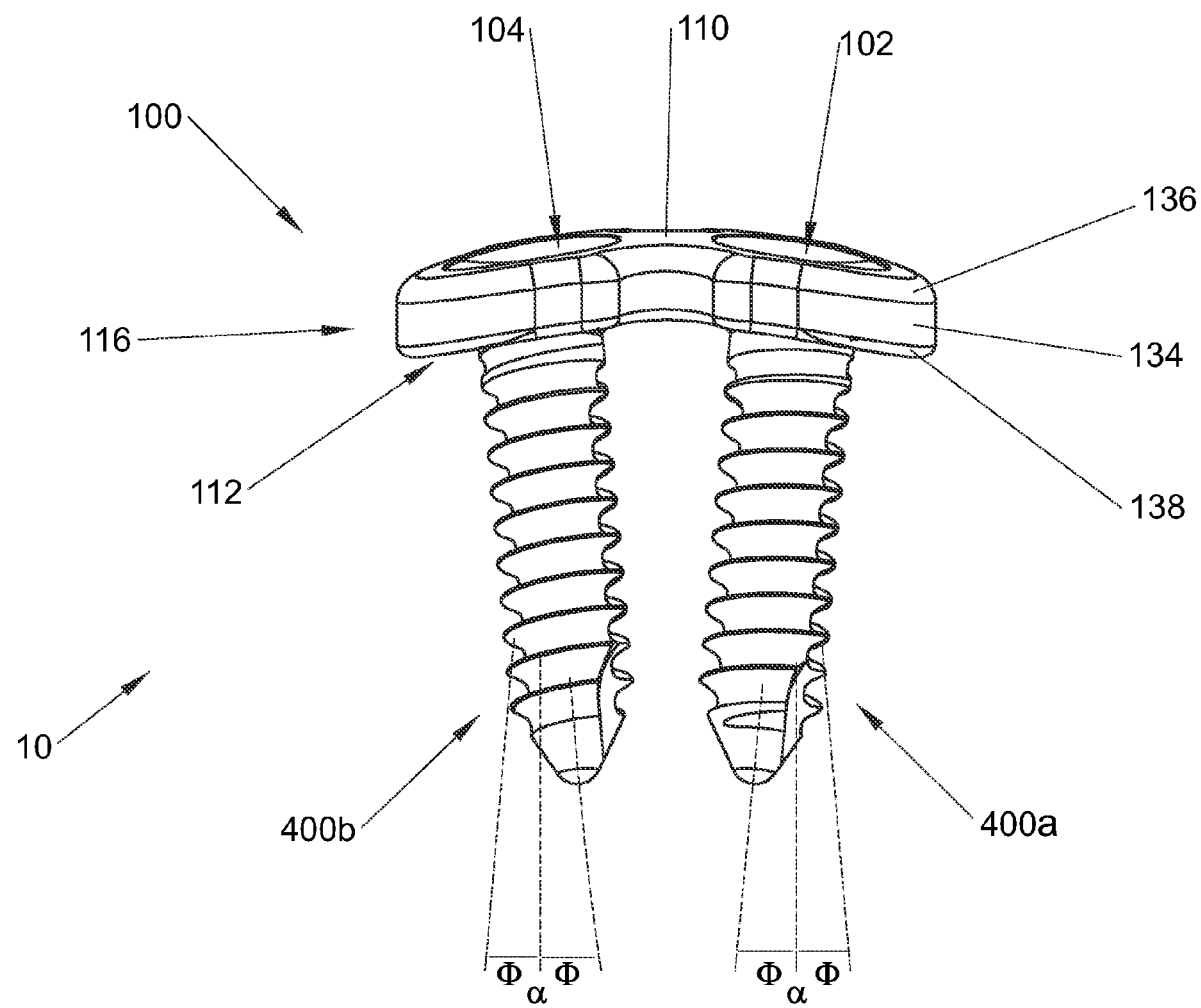
FIG. 3 is an end elevational view of the bone plate system showing a range of insertion angles of bone anchors in the bone plate through bores.
Figure 4:
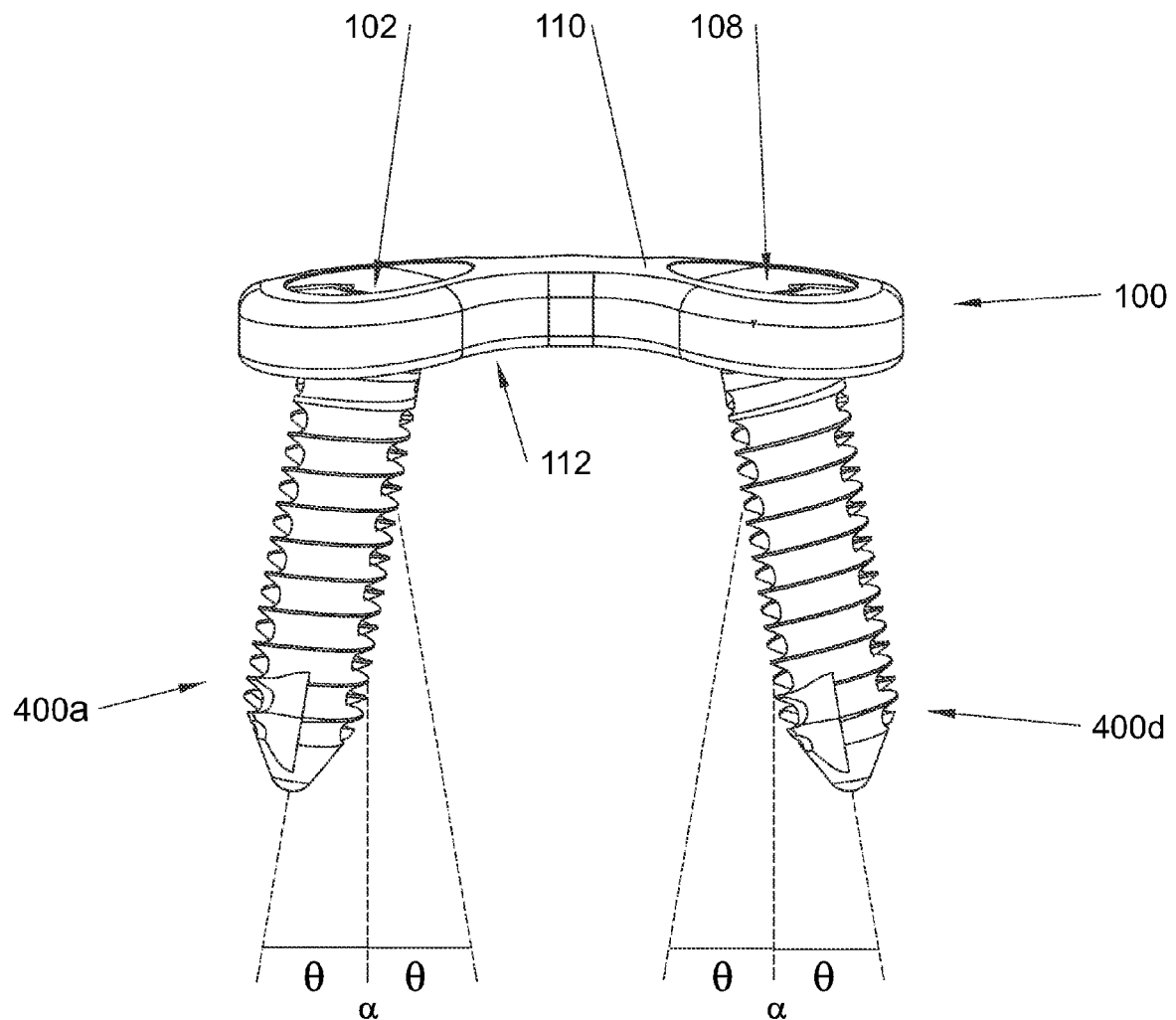
FIG. 4 is a side elevational view of the bone plate system showing the range of bone anchor assembly insertion angles.

As shown in FIGS. 3 and 4, the bone plate 100 may be provided with a curvature in the longitudinal and lateral directions so that the bone plate may conform to the natural curvature of the bone, as well as reduce interference with surrounding tissues. Additionally, the sidewall 116 may include a flat outer surface 134 and curved upper and lower surfaces 136, 138 which provide a smooth transition between the flat outer surface 134 and the upper and lower surfaces 110, 112. The curved upper and lower surfaces 136, 138 also tend to reduce interference of the bone plate 100 with surrounding tissues.

As previously mentioned, the bone plate system 10 permits a bone anchor assembly 400 to be driven into one of the bone plate bores 102, 104, 106, 108 at an angle inclined relative to the bone plate upper surface 110. Driving the bone anchor assembly 400 at an angle relative to the plate may be desirable for a number of reasons, including to secure the bone anchor assembly 400 to a stronger section of the bone. To illustrate the range of potential bone anchor angles in a lateral direction relative to the bone plate 110, FIG. 3 discloses axes a that extend along a respective bore central axis. The bone anchor assemblies 400a, 400b may be driven through the respective bore 102, 104 at angles along the lateral width of the bone plate 110 that are ±Φ relative to the axis α. Conversely, FIG. 4 shows a range of bone anchor assembly 400 insertion angles along the longitudinal length of the bone plate 100 that are ±Φ from the normal axes α. In a preferred embodiment, the bone plate system 10 permits a range of bone anchor assembly 400 insertion angles that are ±5° in the lateral direction and ±20° in the longitudinal direction. To provide the polyaxial insertion capability, the bores 102, 104, 106, and 108 are configured to receive a bone anchor assembly driving end 402, shown in FIG. 8, at a variety of positions within the bores 102, 104, 106, and 108 such that the range of positions for an anchor shank 404 is generally eliptical.

Specifically, the bone plate 100 has bore sidewalls 150a, 150b, 150c, and 150d that extend between the upper and lower surfaces 110, 112 of the bone plate 100 and which generally define the bores 102, 104, 106, and 108, as shown in FIGS. 5-7. Although only four bores are shown, the bone plate 100 may have any number of bores as desired to adequately secure the bone plate 100 to bones using anchor assemblies 400. The bore sidewalls 150 each have a number of interior bore surfaces, including an upper chamfer 152, an annular surface 154, and a lower chamfer 156 (designated by letters a, b, c, or d for the corresponding annular surface). The annular surface 154 generally defines a spherical pocket for receiving the head portion 402 of the bone anchor assembly 400, the driving end 402 expanding into contact with the annular surface 154 to fix the bone anchor assembly 400 relative to the bone plate 100, as will be discussed in greater detail below. Further, the driving end 402 is complimentary to the annular surface 154 so that the driving end 402 may be in contact with the annular surface 154 throughout the range of insertion angles of the bone anchor assembly 400.

The upper chamfer 152 tapers radially outward from the annular surface 154 to accommodate a bone anchor assembly 400 as it passes into the respective bone plate bore at an angle relative to the bone plate 100. Similarly, the lower chamfer 156 tapers radially outward from the annular surface 154 to accommodate the bone anchor assembly 400 as it extends from the lower surface 112 of the bone plate 100. At the junction of the annular surface 154 and the upper chamfer 152 there is an upper lip 158 that projects radially inward which restricts back out of the bone anchor assembly 400 from within the bores 102, 104, 106, and 108. There is also a lower lip 160 at the junction of the annular surface 154 and the lower chamfer 156 that generally defines a lower diameter that is smaller than at least a portion of the bone anchor assembly driving end 402 such that the lower lip 160 restricts the driving end 402 from passing completely beyond the bone plate 100.

Figure 8:
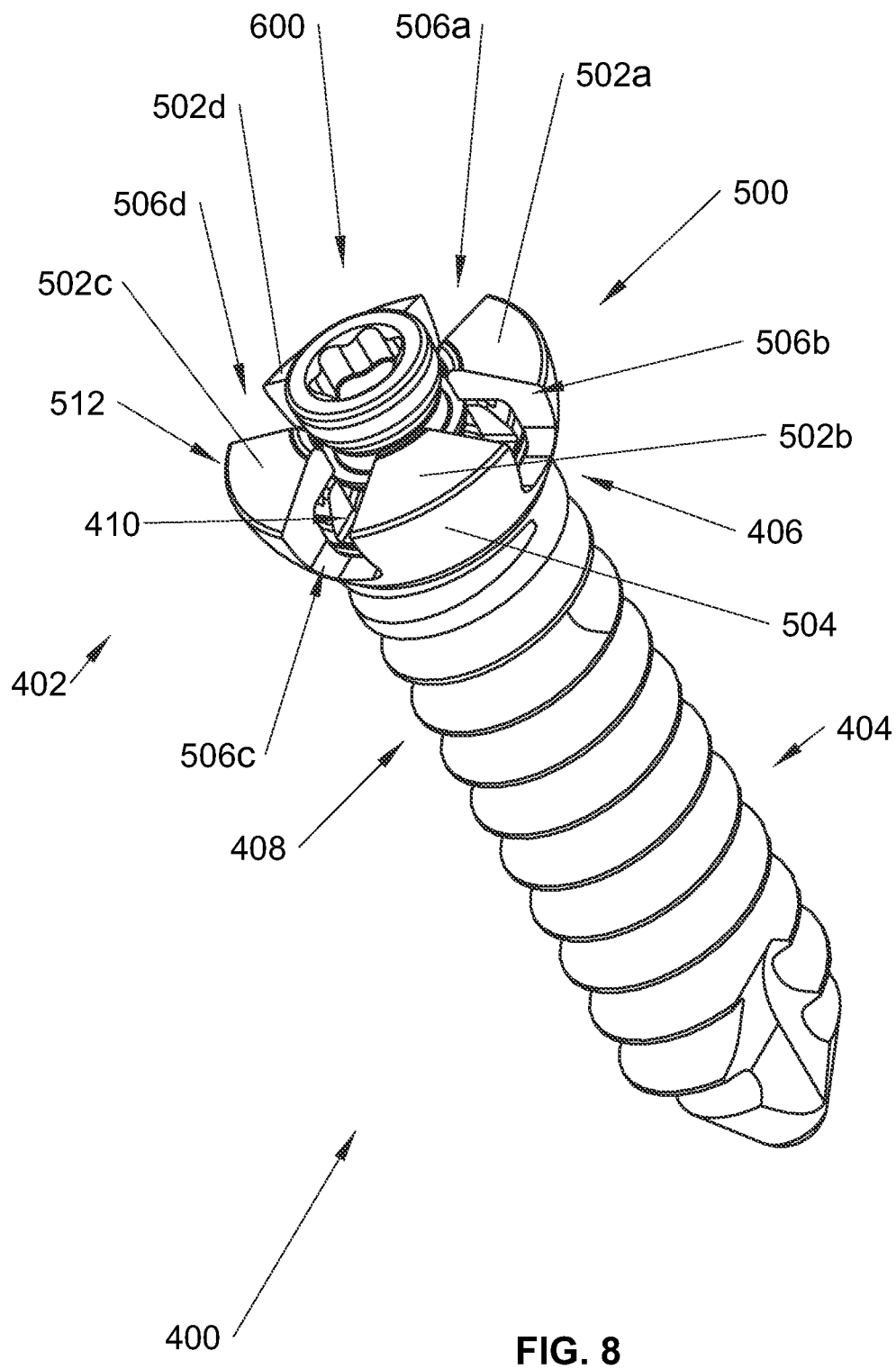
FIG. 8 is a perspective view of one of the bone anchor assemblies of FIG. 2 showing a locking cap and locking fastener connected to a head portion of a bone anchor.

The bone anchor assembly 400 is generally elongate and includes a driving end 402 and a shank end 404, as shown in FIG. 8. The shank end 404 may be threaded or non-threaded according to the desired bone engagement. Alternatively, the shank end 404 may be configured to engage a member (not shown) pre-positioned within the subject bore. In a preferred form, the shank end 404 is a threaded self-tapping design having a primary diameter of 6 mm. The driving end 402, on the other hand, includes a locking cap 500 carried on a head portion 406 of a bone anchor 408, as well as a locking fastener 600 connected to the anchor head portion 406. In one embodiment, the locking cap 500 includes a plurality of projections 502a, 502b, 502c, and 502d extending radially inward from an annular wall 504 of the locking cap 500. Slots 506a, 506b, 506c, and 506d separate the projections 502 and are generally aligned with circumferentially spaced depressions 410a, 410b, 410c, and 410d formed in the anchor head portion 406, as shown in FIG. 11. The aligned slots 506 and depressions 410 permit a driver to be passed axially downward into contact with the depressions 410 to drive the bone anchor shank end 404 into a bone without turning the locking cap 500 relative to the anchor head portion 406.

Figures 9, 10:
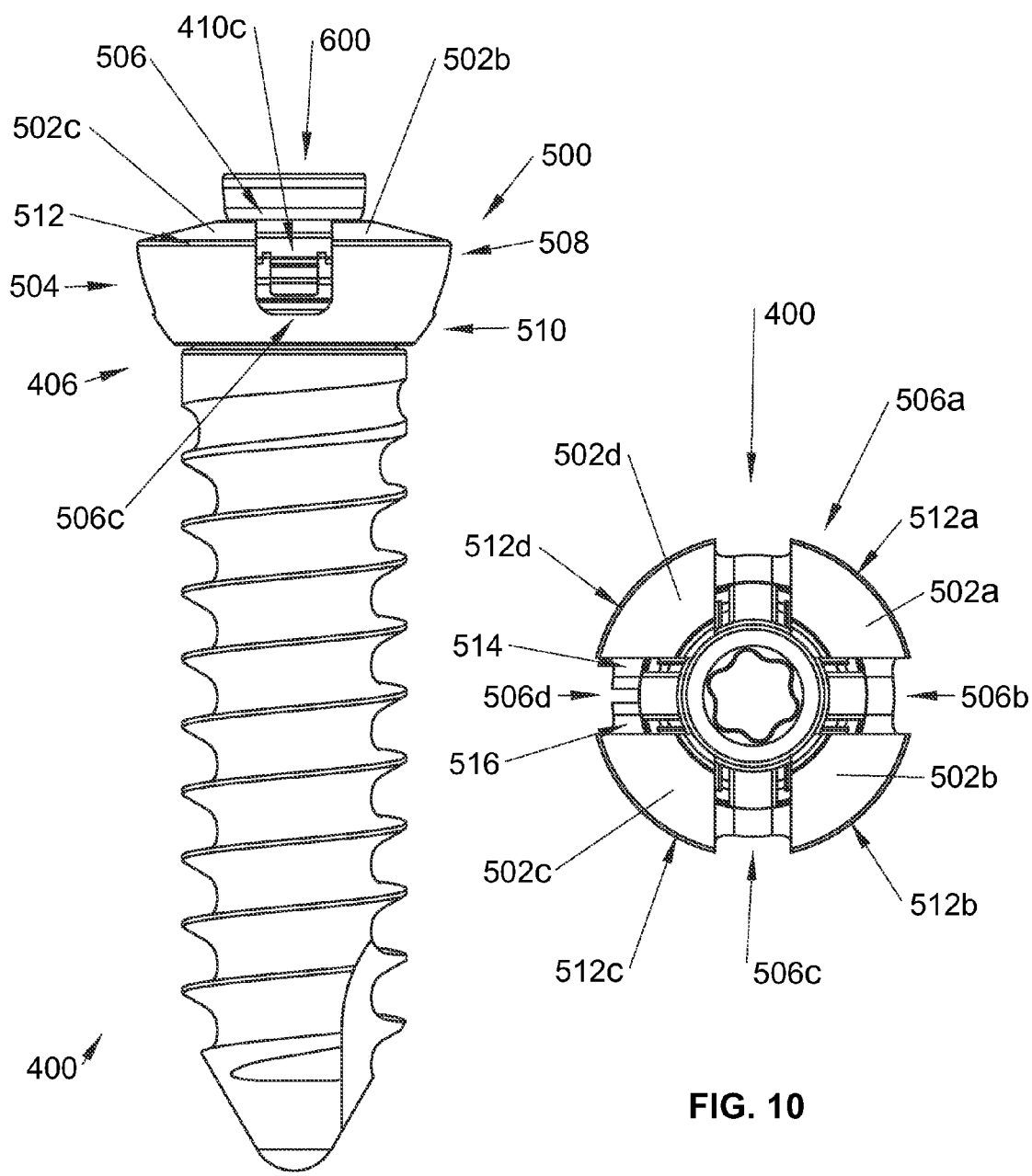
FIG. 9 is an elevational view of the bone anchor assembly of FIG. 8 showing alignment between a slot of the locking cap and a depression of the bone anchor head portion.
FIG. 10 is a plan view of the bone anchor assembly of FIG. 8 showing radial projections of the locking cap.

Turning now to FIGS. 9 and 10, the locking cap annular wall 504 extends axially along the anchor head portion 406 and includes a radially outer upper end portion 508 that is configured to be shifted radially outward and into tight engagement with the bore annular surface 154 as the locking fastener 600 is driven into the anchor head portion 406. In one embodiment, the radially outer upper end portion 508 may include a plurality of spaced upper circumferentially extending shoulders 512a, 512b, 512c, and 512d that expand apart radially outward toward the bore annular surface 154 as the locking fastener 600 cams against the locking cap 500, which will be discussed in greater detail below. The annular wall 504 may also include a lower radially raised arcuate outer surface portion 510 that is complimentary to the curvature of the bore annular surface 154 such that the annular surface 154 urges the outer surface portion 510 radially inward as the bone anchor assembly driving end 402 is seated within a bone plate through bore.

The locking cap 500 is generally C-shaped with opposing ends 514, 516 positioned between projections 502c, 502d, as shown in FIG. 10. The locking cap 500 is preferably resilient, such that the ends 514, 516 may expand apart when the locking cap 500 is installed onto the anchor head portion 406. Moreover, the slots 506 and the gap spacing between the ends 514, 516 provide flexibility to the locking cap 500 so that the radially outer upper end portion 508 and projections 502 may expand radially outward.

With the locking cap 500 and locking fastener 600 removed from the anchor head portion 406, an axial bore 412 of the anchor head portion 406 is exposed, as shown in FIGS. 11 and 12. The axial bore 412 includes an enlarged diameter upper opening portion 416 that opens to an upper end of the anchor head portion 406 and extends axially downward therefrom. The axial bore 412 may have a threaded portion 414. In one form, the axial bore 412 is partially defined by an inner annular surface 418 that is uninterrupted and is generally formed by a solid wall portion 420 of the anchor head portion 406. The anchor head portion 406 also includes pairs of axially upwardly projecting bosses 422a, 422b that each have a recess 424 therebetween that is sized and configured to receive one of the locking cap projections 502. If the locking cap 500 begins to rotate relative to the anchor head portion 406, the one or more projections 406 will rotate into contact with one of the corresponding bosses 422a, 422b. At this point, one of the bosses 422a, 422b will resist further rotation of the projection 406 to maintain the locking cap 500 in position on the anchor head portion 406.

As shown in FIG. 12, the anchor head portion 406 also includes an annular channel 430 having a cylindrical inner surface 432 extending substantially parallel to the longitudinal axis of the bone anchor 408. Annular upper and lower surfaces 434 and 436 extend toward the cylindrical inner surface 432 in a direction generally transverse to the bone anchor longitudinal axis. At the upper end of the bone anchor 408, the anchor head portion has a radially outer upper surface 440 that tapers radially inward going toward the upper end and away from the annular channel 430. In one form, the radially outer upper surface 440 may be conical.

Figure 13:
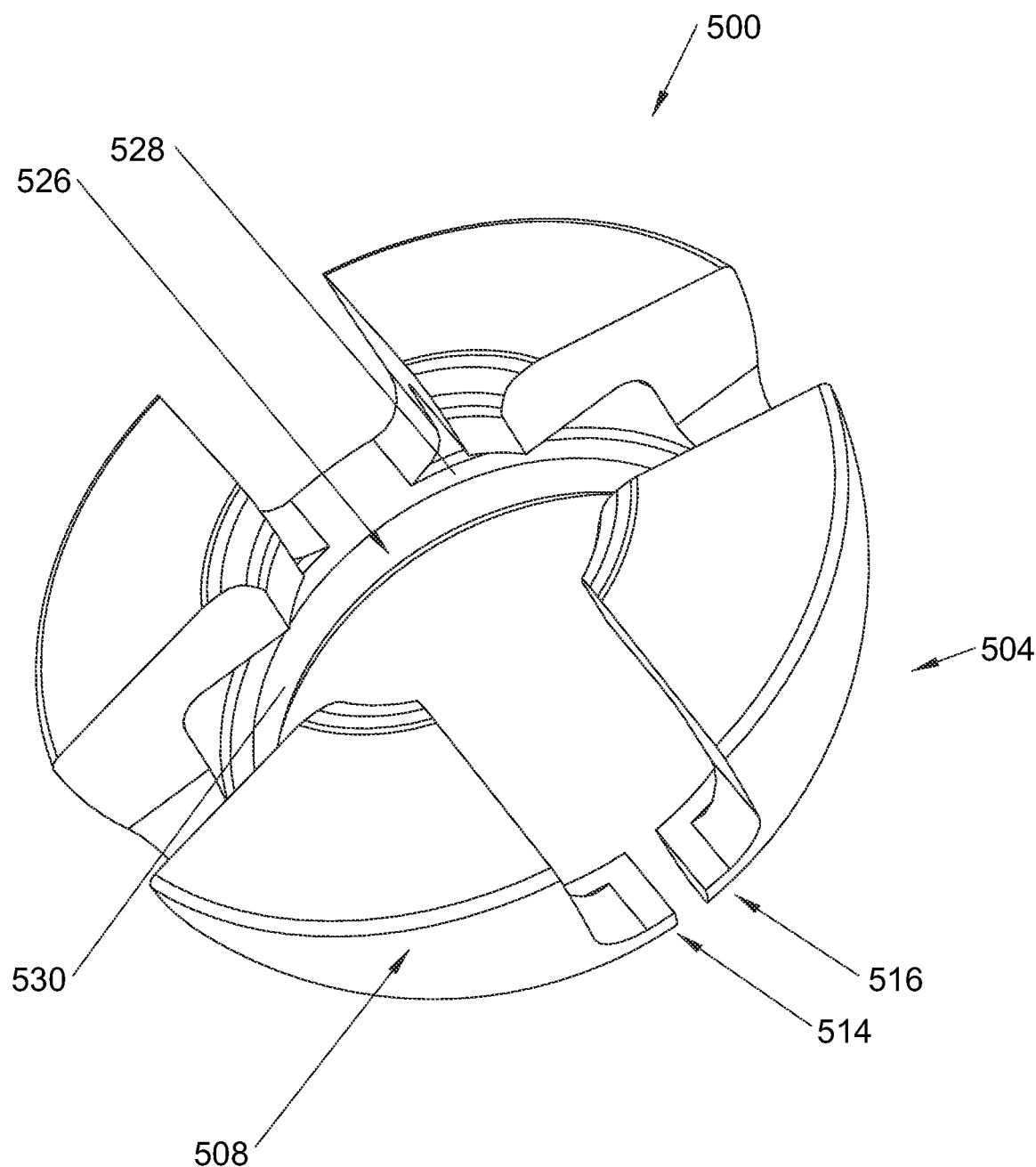
FIG. 13 is a perspective view of the locking cap of FIG. 8 showing a lower inner rim projection of the locking cap.
Figure 14:
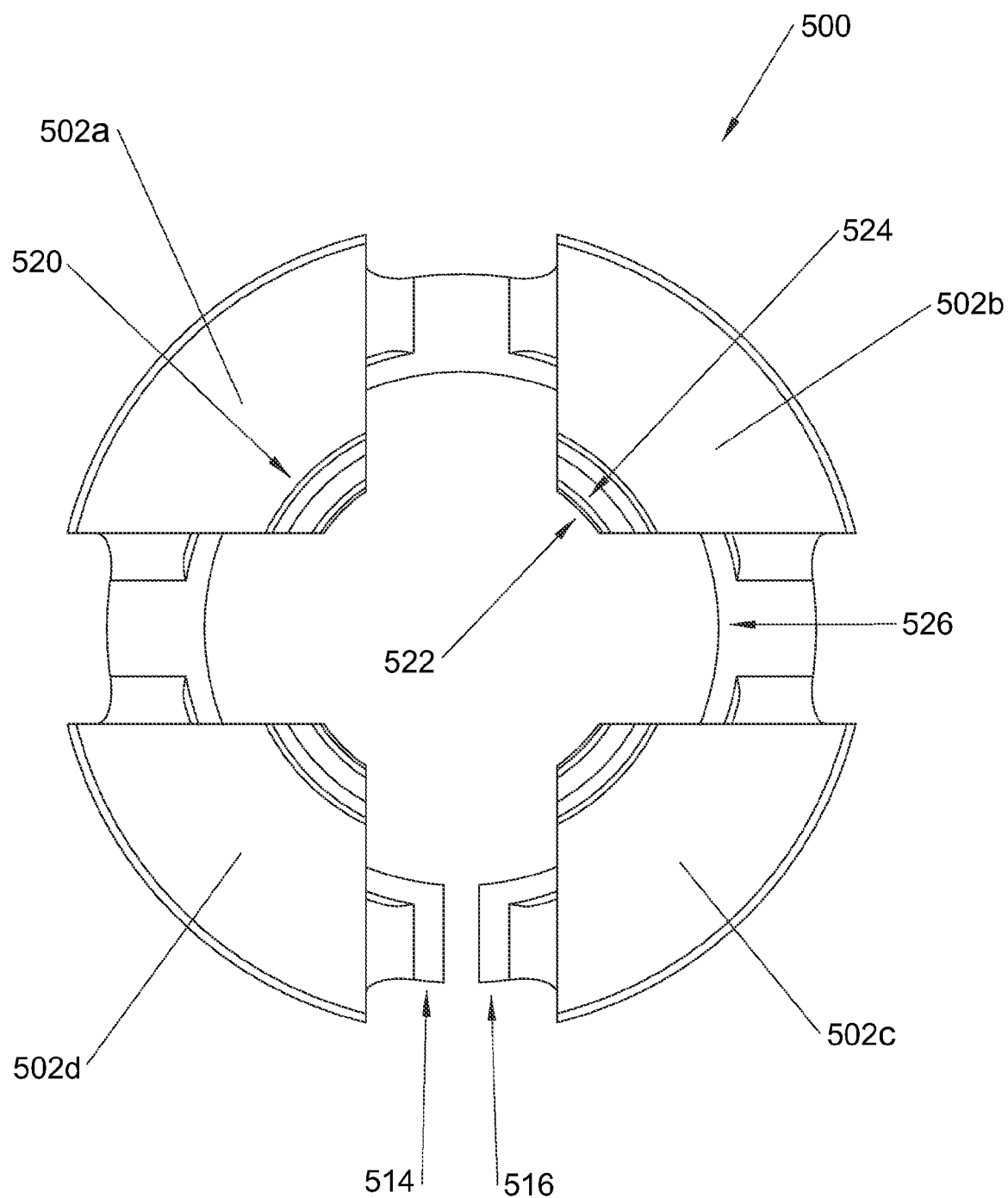
FIG. 14 is a plan view of the locking cap of FIG. 8 showing projections of the locking cap that extend radially inward.

Drawing attention to FIGS. 13 and 14, additional features of the locking cap 500 are presented. At the lower end of locking cap 500, a radially inner lower end portion 526 is sized and configured to fit into the annular channel 430 of the anchor head portion 406. The lower end portion 526 includes a flat annular upper surface 528 that abuts the annular upper surface 434 of the anchor head portion 406 when the locking cap 500 is carried on the anchor head portion 406. Additionally, a curved inner surface 530 of the lower end portion 526 contacts and is complimentary to the cylindrical inner surface 432 of the anchor head portion 406.

With respect to the interaction between the locking cap 500 and the locking fastener 600, the locking cap 500 includes a radially inner upper cam surface 520 that cooperates with the locking fastener 600. In one embodiment, the locking cap projections 502 may have radially inner ends 522. Here, the radially inner upper cam surface 520 may be in the form of a plurality of cam surfaces 524 on the radially inner ends 522. In greater detail, the plurality of cam surfaces 524 are arranged to be complimentary to the locking fastener 600 and are generally inclined away from the radially inner ends 522.

Figure 15:
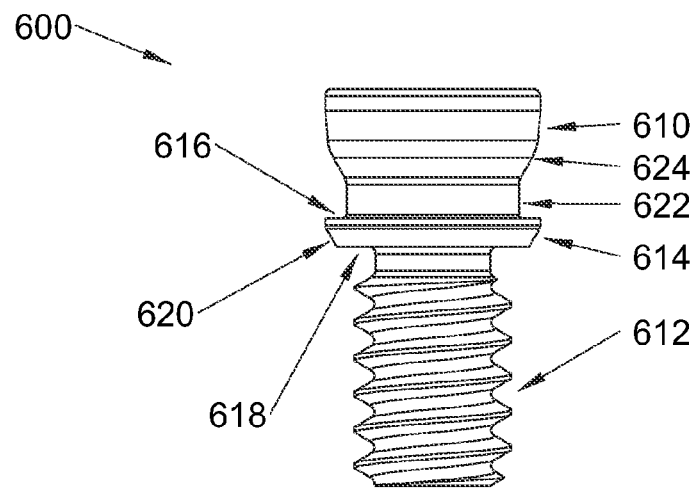
FIG. 15 is a perspective view of a locking fastener of the bone anchor assembly of FIG. 8 showing an enlarged upper head portion and depending threaded shank portion.
Figure 16:
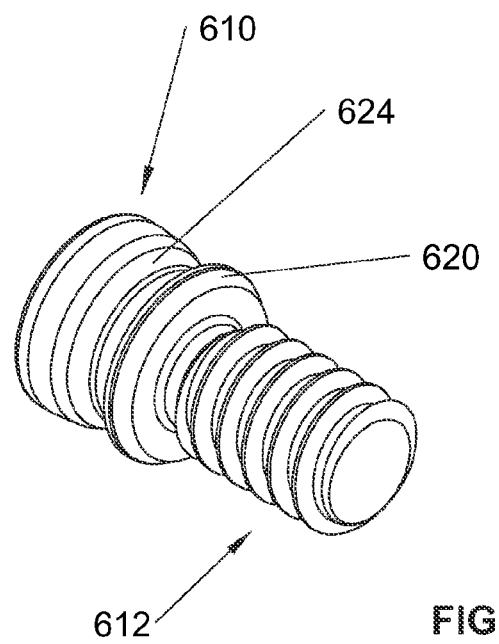
FIG. 16 is a side elevational view of the locking fastener of FIG. 15 showing an annular collar between the head and neck portion.
Figure 17:
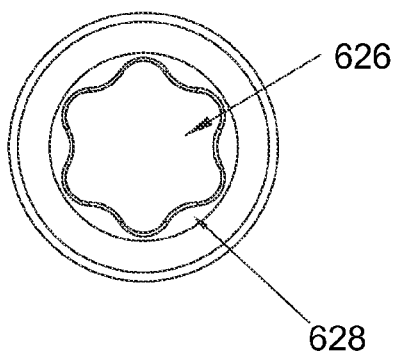
FIG. 17 is a plan view of the locking fastener of FIG. 8 showing a bore of the locking fastener configured to receive a driver.

As shown in FIGS. 15-17, the locking fastener 600 has an upper head portion 610 that is configured for driving the locking fastener 600 into the bone anchor bore 412 and is sized to be received within the upper opening portion 416 of the bone anchor bore 412. The locking fastener shank 612 may have a number of different designs to permit the fastener 600 to advance longitudinally along the bone anchor bore 412 while resisting back out, including but not limited to threads, an expanding end, or teeth that engage a pawl. In a preferred embodiment, the locking fastener shank 612 is threaded to engage the threaded portion 414 of the bone anchor bore 412. The locking fastener shank 612 is adjacent an annular collar 614 of the locking fastener 600. The annular collar 614 has a flat upper surface 616, a flat lower surface 618, and a radially extending lower cam surface 620 extending therebetween. Axially above the flat upper surface 616 is a narrow portion 622 that may be generally cylindrically shaped and leads to a radially extending upper cam surface 624. As shown in FIG. 17, the locking fastener upper head portion 610 has a driver bore 626 for receiving a hex-lobe driver and an undulating wall 628 that contacts the lobes of the driver and transfers rotation of the tool to the locking fastener 600.

Referring now to FIGS. 18-24, a method of assembling the bone anchor assembly 400 into a preassembled condition will be disclosed. Once the preassembled condition is complete, the bone anchor assembly 400 is ready to be driven through a bone plate through bore and into a bone. Preferably, the assembly process is performed by the manufacturer to limit preparatory work required for surgery.

Figure 18:
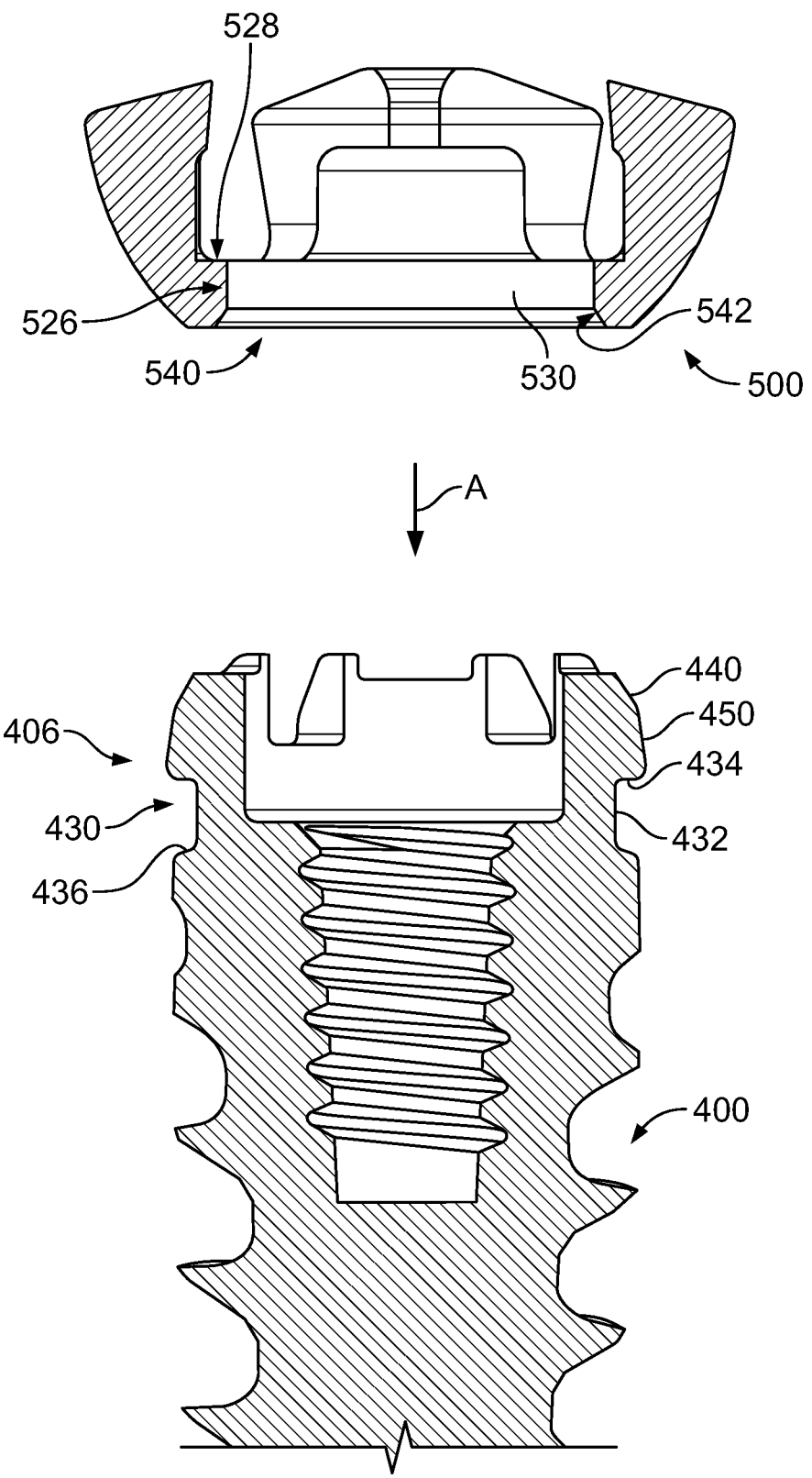
FIGS. 18-24 are cross-sectional views of the bone anchor assembly of FIG. 8 that illustrate the assembly of the locking cap and locking fastener to the bone anchor.

The process begins with passing an open end 540 of the locking cap 500 over the anchor head portion 406 in direction A once the locking cap 500 and bone anchor 408 have been aligned. In the embodiment shown, the locking cap open end 540 includes the radially inner lower end portion 526 that is configured to fit within the channel 430 formed in anchor head portion 406. As is shown in FIG. 18, the radially inner lower end portion 526 has a lower chamfered portion 542 that is designed to guide the radially outer upper surface 440 into the locking cap open end 540 and thereby expand the open end 540 over the anchor head portion 406.

Figure 19:
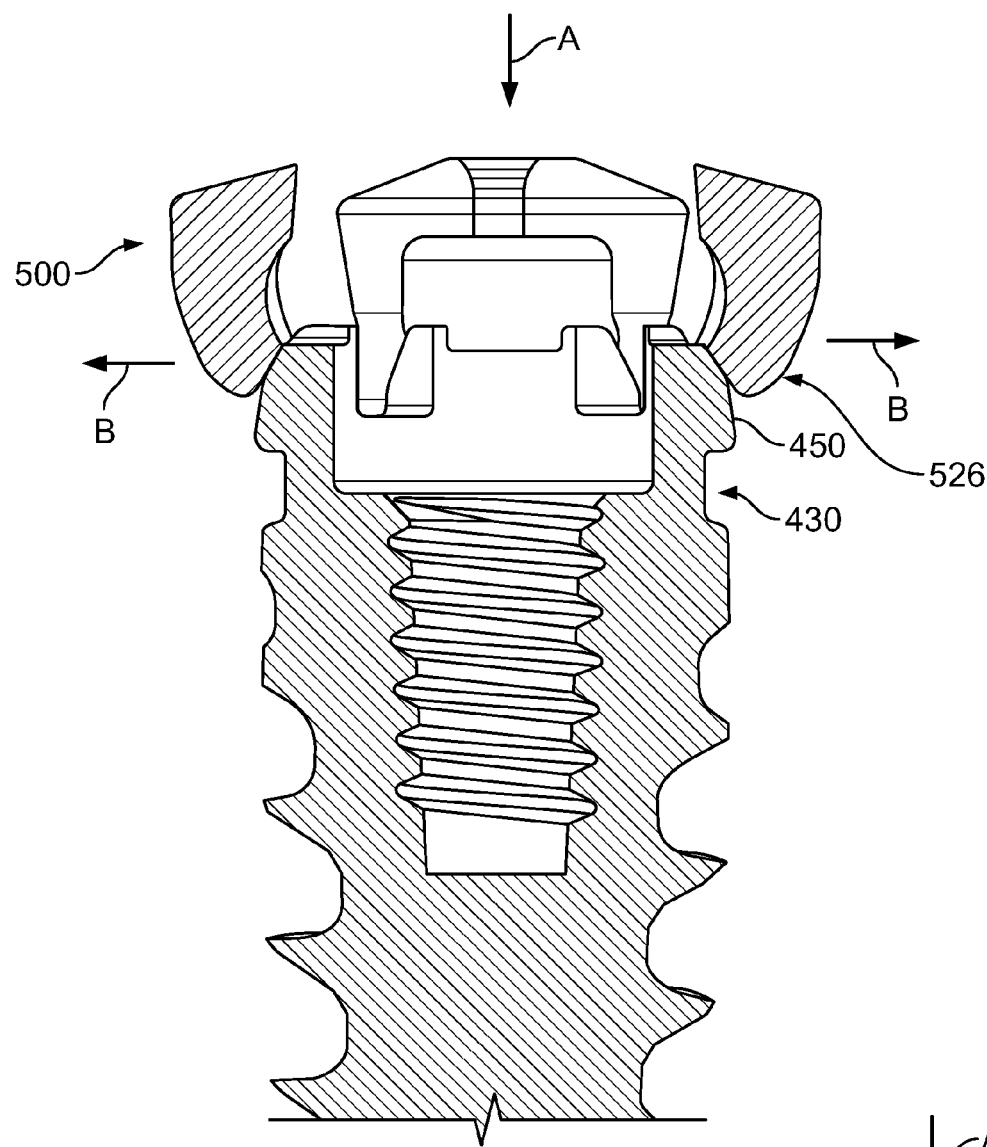
Figure 20:
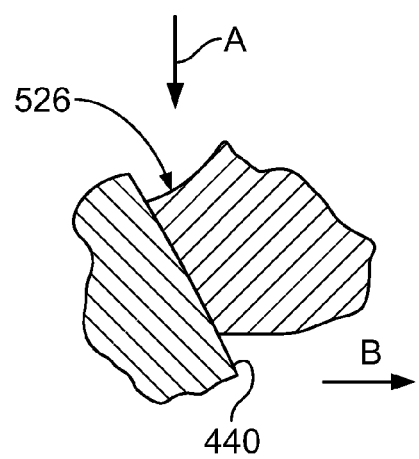
Figure 21:
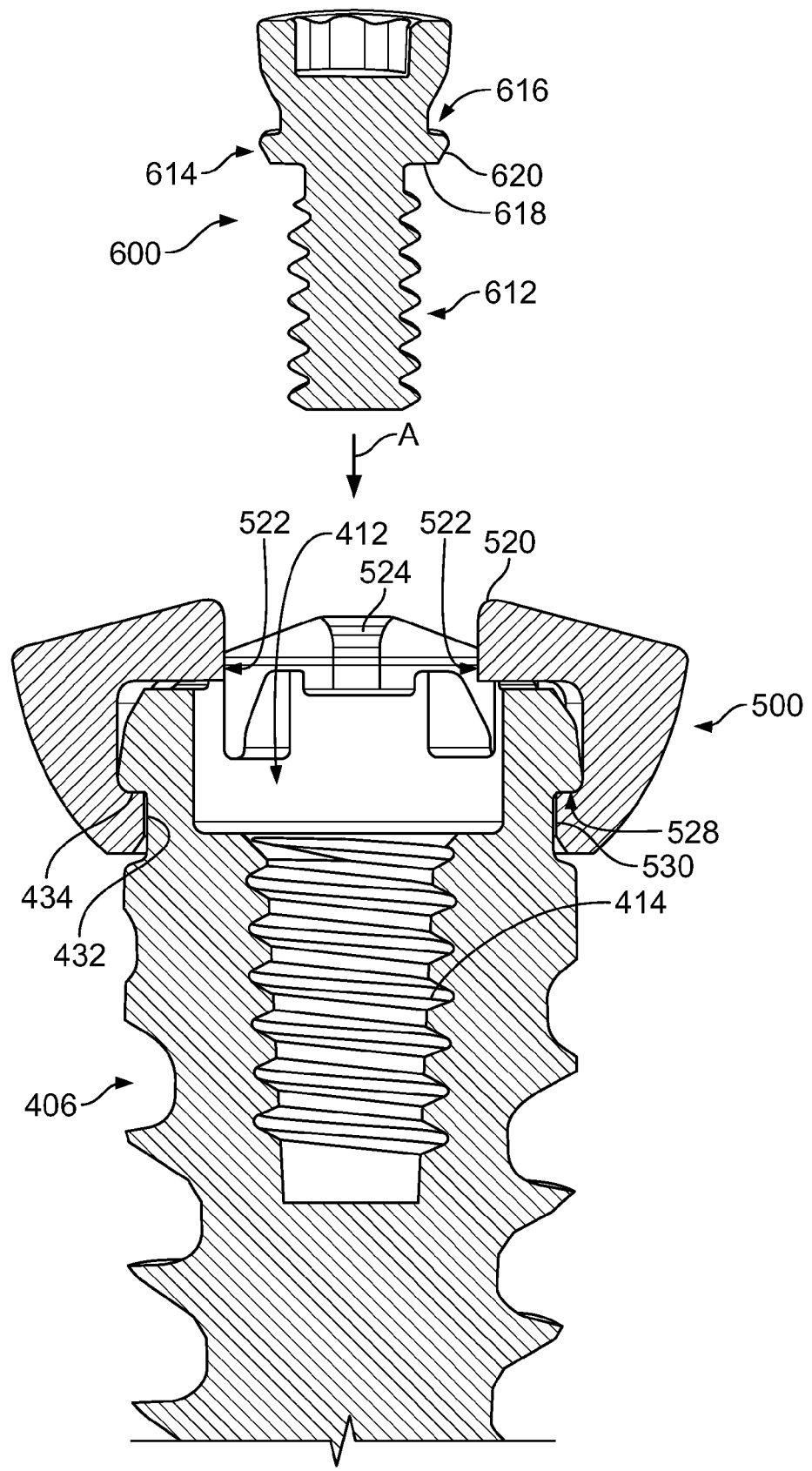

As the locking cap 500 is advanced in direction A onto anchor head portion 406, the locking cap curved inner surface 530 acts as a lower cam portion against the radially outer upper surface 440 such that the radially inner lower end portion 526 is shifted radially outward in direction B, as shown in FIGS. 19 and 20. Further, an enlarged radially outer upper surface 450 of the anchor head portion 406 continues to expand the radially inner lower end portion 526 as the locking cap 500 is advanced in direction A. Eventually, the radially inner lower end portion 526 reaches the bone anchor annular channel 430 and contracts radially into the channel 430 to form a snap-fit connection between the locking cap 500 and the anchor head portion 406, as shown in FIG. 21. Stated differently, snap-fitting the radially inner lower end portion 526 into channel 530 engages the locking cap flat annular upper surface 528 and curved inner surface 530 respectively against the anchor head portion annular upper surface 434 and cylindrical inner surface 432 to retain the locking cap 500 on the anchor head portion 406. As the radially inner lower end portion 526 reaches the channel 430, the locking cap projections 502, if present, should be aligned between the pairs of axially upwardly projecting bosses 422a, 422b so that the projections 502 may be seated therein once the lower end portion 526 reaches the channel 430 and the locking cap 500 is seated on the anchor head portion 406.

Figure 22:
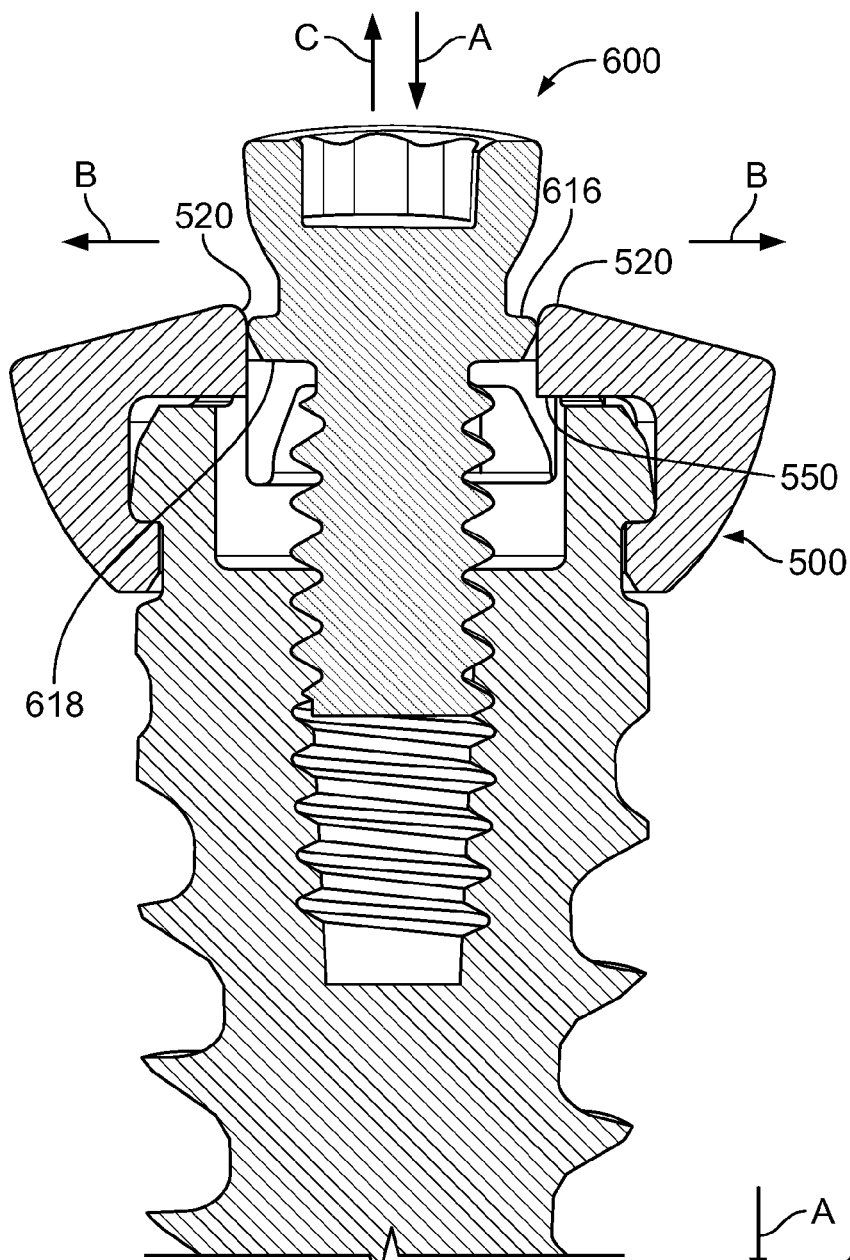
Figure 23:
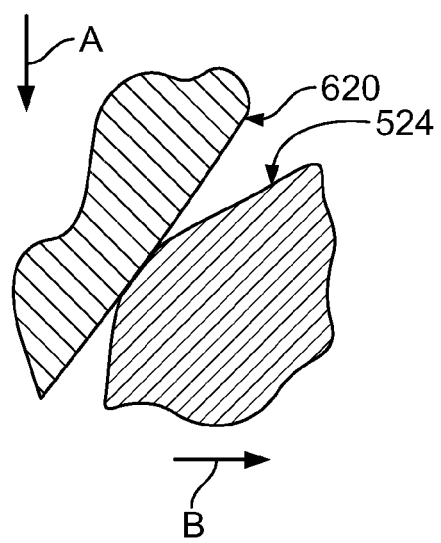
Figure 24:
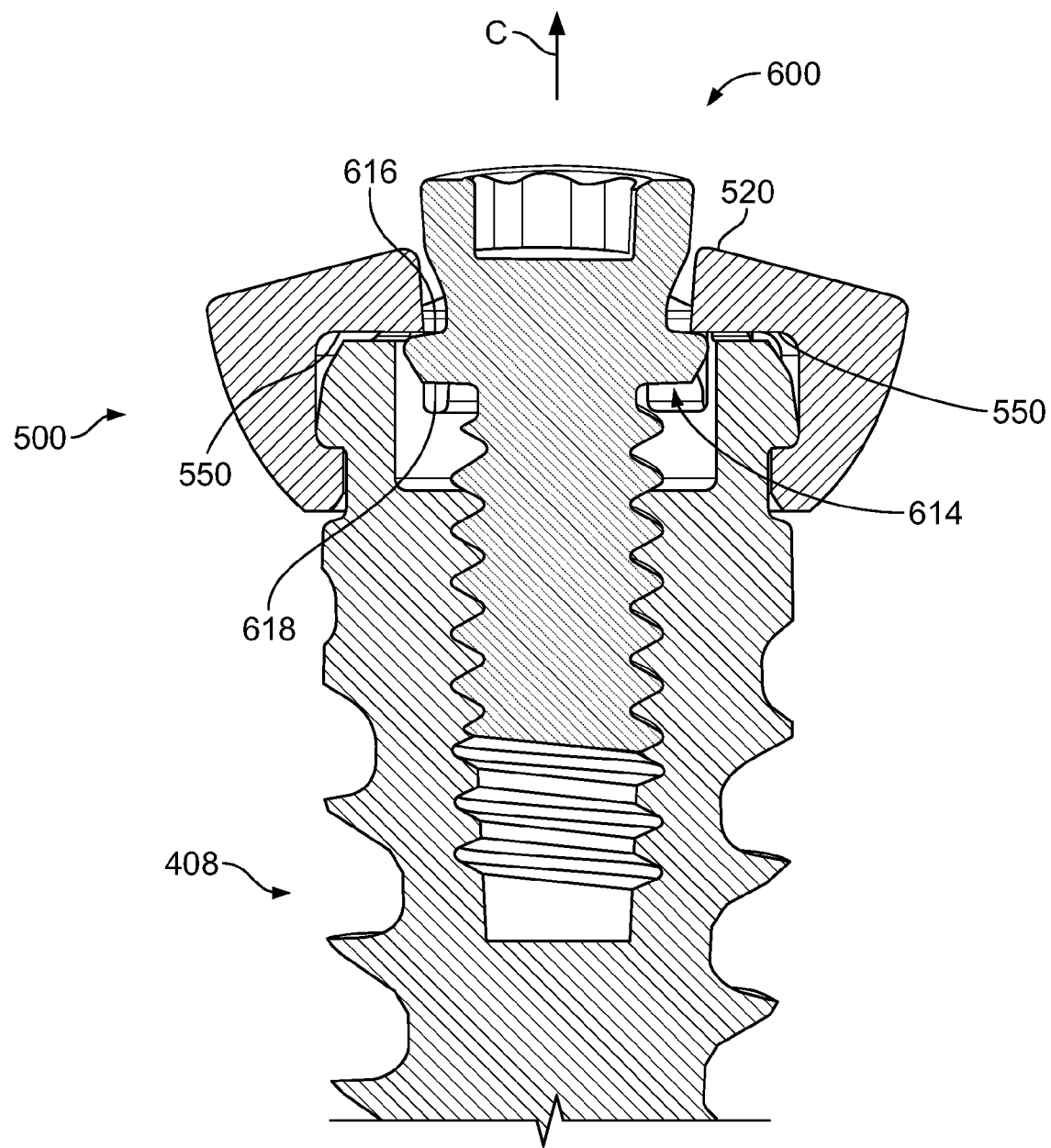
Figure 25:
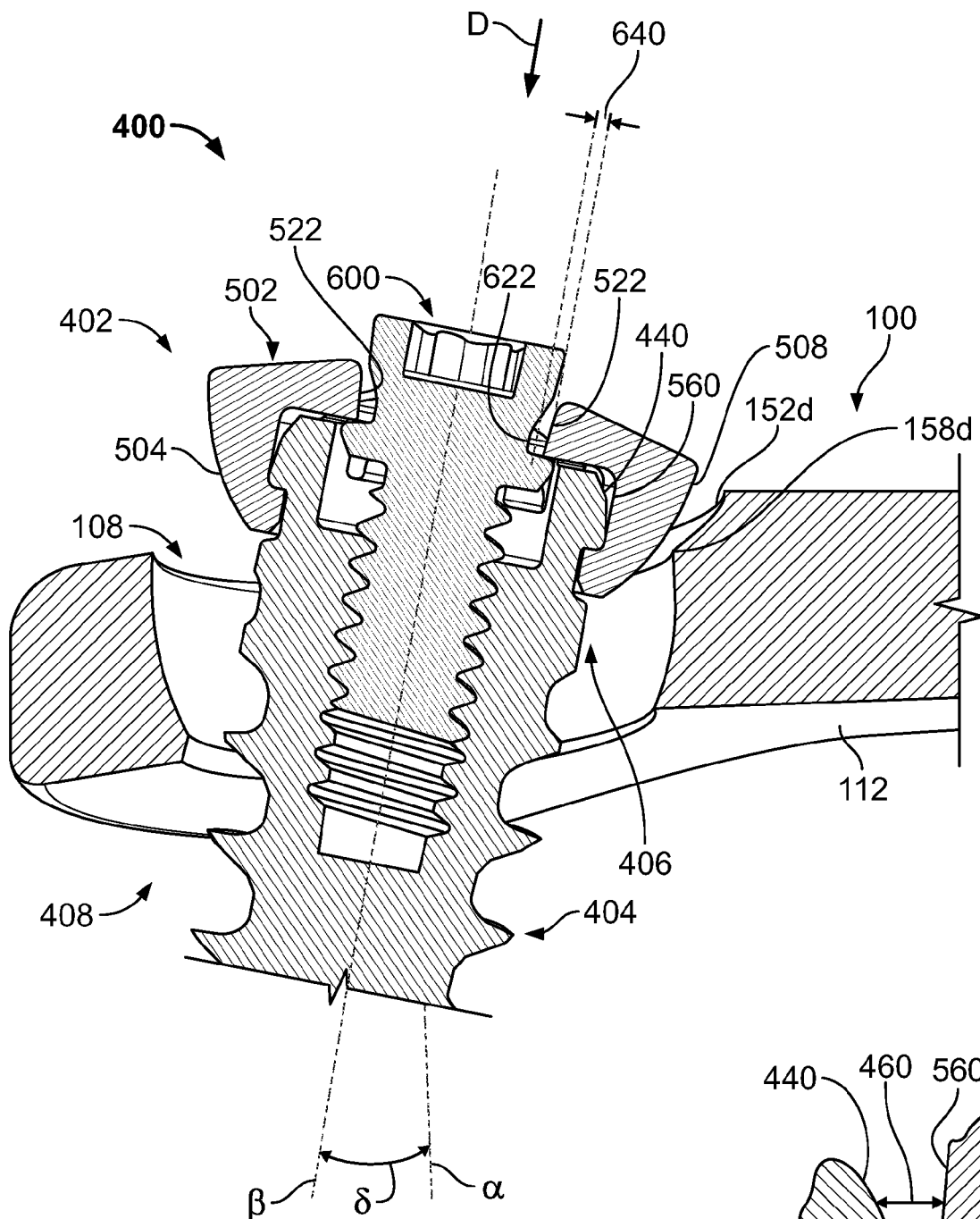
FIGS. 25-31 are cross-sectional views of the bone plate system showing the bone anchor assembly being driven through one of the bone plate through bores and the locking cap being radially expanded to fix the bone anchor assembly to the bone plate.

FIGS. 21-24 illustrate the step of connecting the locking fastener 600 to the anchor head portion 406. The locking fastener shank 612 is passed into the anchor head portion bore 412 in direction A and into engagement with bore threaded portion 414 or other surfaces therein. Preferably, the locking fastener shank 612 and the flat lower surface 618 are sized to permit these features of the locking fastener 600 to pass beyond the radially inner upper cam surface 520 of the locking cap 500 in direction A. However, the radially extending lower cam surface 620 of the locking fastener is preferably sized to contact the radially inner upper cam surface 520 and cam the surface 520 radially outward in direction B such that the larger flat upper surface 616 may pass beyond the radially inner upper cam surface 520 and into an intermediate axial position along the longitudinal axis of the anchor head portion 406. Preferably, the radially inner upper cam surface 520 will resiliently contract radially inward so that the locking fastener annular collar 614 is positioned axially below the locking cap radially inner upper cam surface 520, as shown in FIG. 24. In this intermediate axial position, the locking cap 500 may resist back out of the locking fastener 600 in direction C. By positioning the locking fastener annular collar 614 below the radially inner upper cam surface 520, the bone anchor 408, locking cap 500, and locking fastener 600 are maintained in the preassembled condition, as shown in FIG. 24. In the preassembled condition, the bone anchor assembly 400 is ready to be driven through a bone plate bore and into a bone.

In one embodiment, the flat upper and lower surfaces 616, 618 have a generally circular outer periphery that defines a diameter for each. Further, the distance between radial inner ends 522 is greater than the diameter of the flat lower surface 618 but greater than the diameter of the flat upper surface 616 so that the fastener shank 612 and flat lower surface 618 may pass beyond the plurality of cam surfaces 524 without radially expanding the projections 502. As the locking fastener 600 continues to advance in direction A, the radially extending lower cam surface 620 will cam against the cam surfaces 524 and expand the projections 502 until the locking fastener inner collar 614 passes beyond the projections 502, as shown in FIGS. 22-24. Then, the resilient properties of the locking cap 500 will tend to shift the projections 502 radially inward such that the locking fastener inner collar 614 is positioned below the locking cap projections 502. Further, the locking cap projections 502 may include substantially flat lower surfaces 550 that extend over the anchor head portion 406. With the locking fastener 600 in the intermediate axial position, the flat upper surface 616 is arranged axially below and in overlapping confronting relation with the substantially flat lower surfaces 550 such that the flat lower surfaces 550 contact and resist the locking fastener 500 if the fastener 500 travels in direction C.

An exemplary method of installing the bone plate system 10 onto one or more bones will now be disclosed in conjunction with FIGS. 25-31. The lower face 112 of bone plate 100 is placed against the one or more bones that are to be rigidly secured by the bone plate 100. A drill or an awl (not pictured) is inserted through bore 108 along axis β, the desired angle of insertion for the bone anchor assembly 400, to form a hole in the target bone. The bone anchor assembly 400 is then driven in direction D into the bore 108 until shank end 404 engages the hole formed in the bone. In one embodiment, the shank end 404 is in the form of a screw such that the bone anchor assembly is rotatably driven in direction D until the bone anchor assembly driving head 402 begins to enter the bore 108. As shown, the bone anchor assembly 400 is driven along an axis β having an angle δ relative to the normal axis α of the lower surface 112 of the bone plate 110, as taken from the center of bore 108. Because δ is a relatively large angle, the locking cap annular wall 504 will contact upper lip 158d as anchor assembly 400 is rotatably engaged with the bone and the bone anchor assembly driving head 402 is seated within the bore 108.

Figure 26:
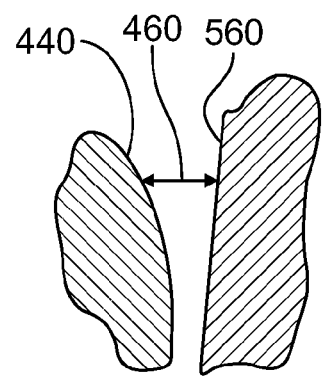
Figure 27:
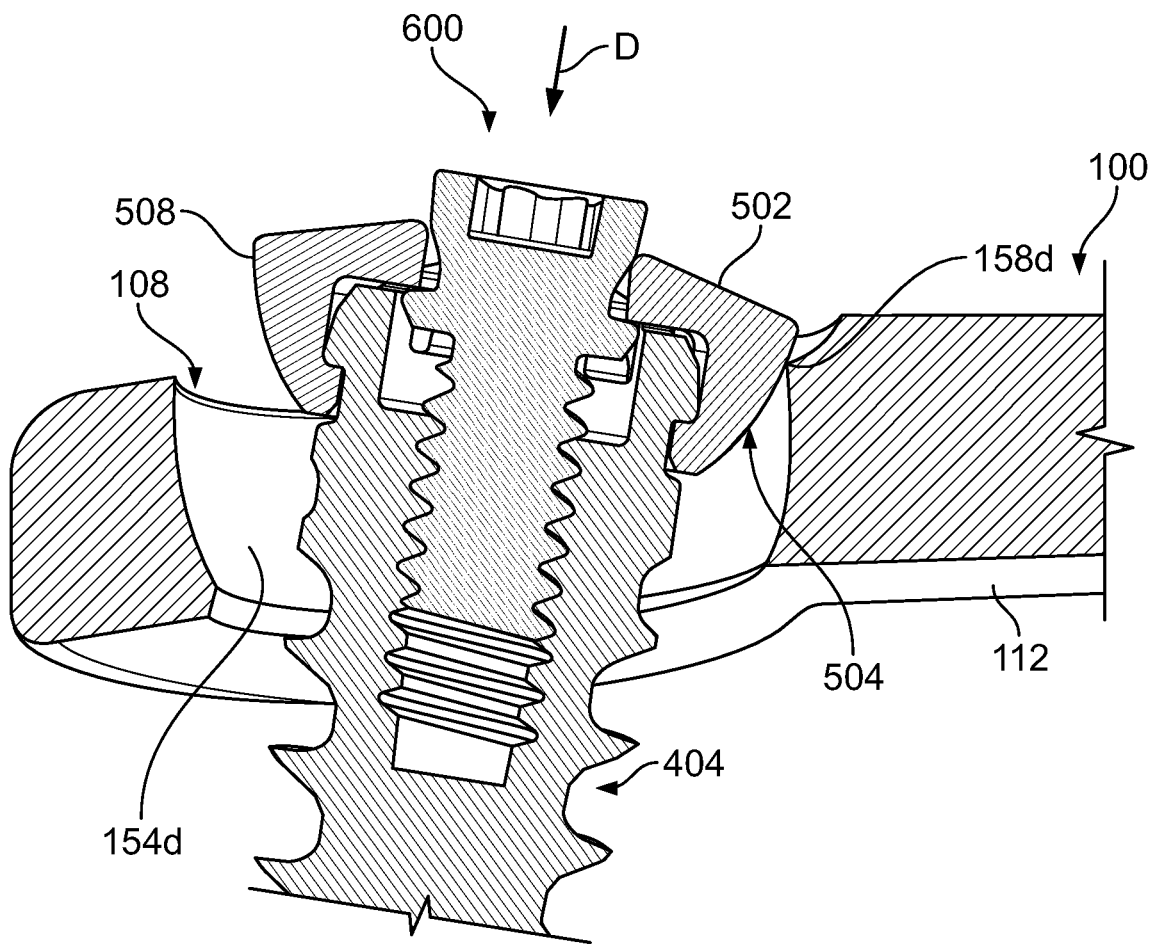

As previously discussed, bone anchor assembly 400 may include locking cap projections 502 extending from the locking cap annular wall 504 with radially inner ends 522. In the preassembled condition, such an embodiment preferably has the locking cap projections 502 aligned with the locking fastener narrow portion 622 with the locking fastener at the intermediate axial position in the bone anchor 408. The radially inner ends 522 are each separated from the locking fastener narrow portion 622 by a gap spacing 640. The gap spacing 640 permits one or more radially inner ends 522 to shift radially inward due to contact of the locking cap annular wall portion 504 with the upper lip 158d or other features of the bone plate 100 as the locking cap 500 and anchor head portion 406 enter the bore 108. The radially inward shift is best shown by the difference between FIGS. 25 and 27. In one form, the locking cap 500 may have a radially inner upper surface 560 that is separated by a gap spacing 460 from the radially outer upper surface 440 of the anchor head portion 406, as shown in FIG. 26. The gap spacing 460 permits the locking cap annular wall portion 504 to deflect radially inward as the annular wall portion 504 contacts the upper lip 158d or other features of the bone plate 100.

Figure 28:
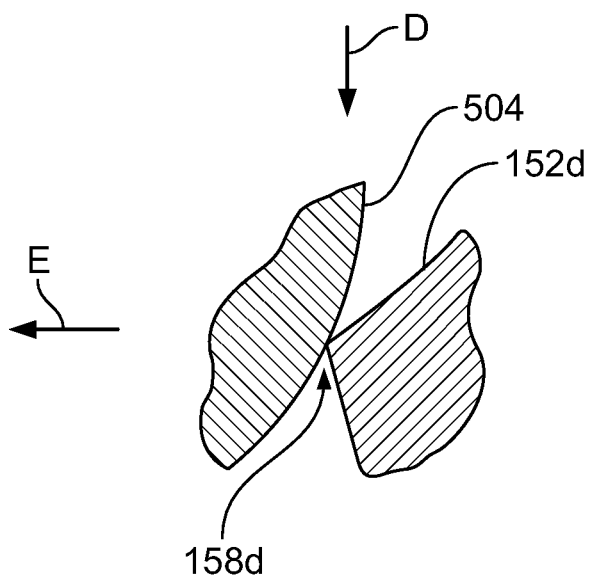

To ease insertion into the bore 108, the locking cap annular wall portion 504 is preferably arcuate such that the annular wall portion 504 will cam against the upper lip 158d. In this manner, the annular wall portion 504 may be shifted radially inward in direction E as the bone anchor assembly is driven in direction D, as shown in FIG. 28. Additionally, the radially outer upper end portion 508 may have an outer curvature that is flush with the rest of annular wall portion 504 so that the locking cap 500 will tend not to get caught on upper lip 158d or other features of the bone plate 100.

Once the anchor head portion 406 and locking cap 500 carried thereon are positioned within the bore 108, the locking cap 500 is seated against the bore annular surface 154d. In a preferred form, at least the locking cap radially outer upper end portion 508 is seated against the bore annular surface 154d due to the smaller diameter of lower lip 160 that restricts the bone anchor driving end 402 from fully passing beyond the bone plate 100. Next, the locking fastener 600 may be driven axially into the anchor head portion 406 to expand the locking cap 500 and fix the bone anchor assembly 400 relative to the bone plate 100. In the illustrated embodiment, the locking fastener 600 has a threaded shank 612 so the locking fastener 600 is rotated in direction F to drive the locking fastener 600 into the anchor head portion 406.

Figure 29:
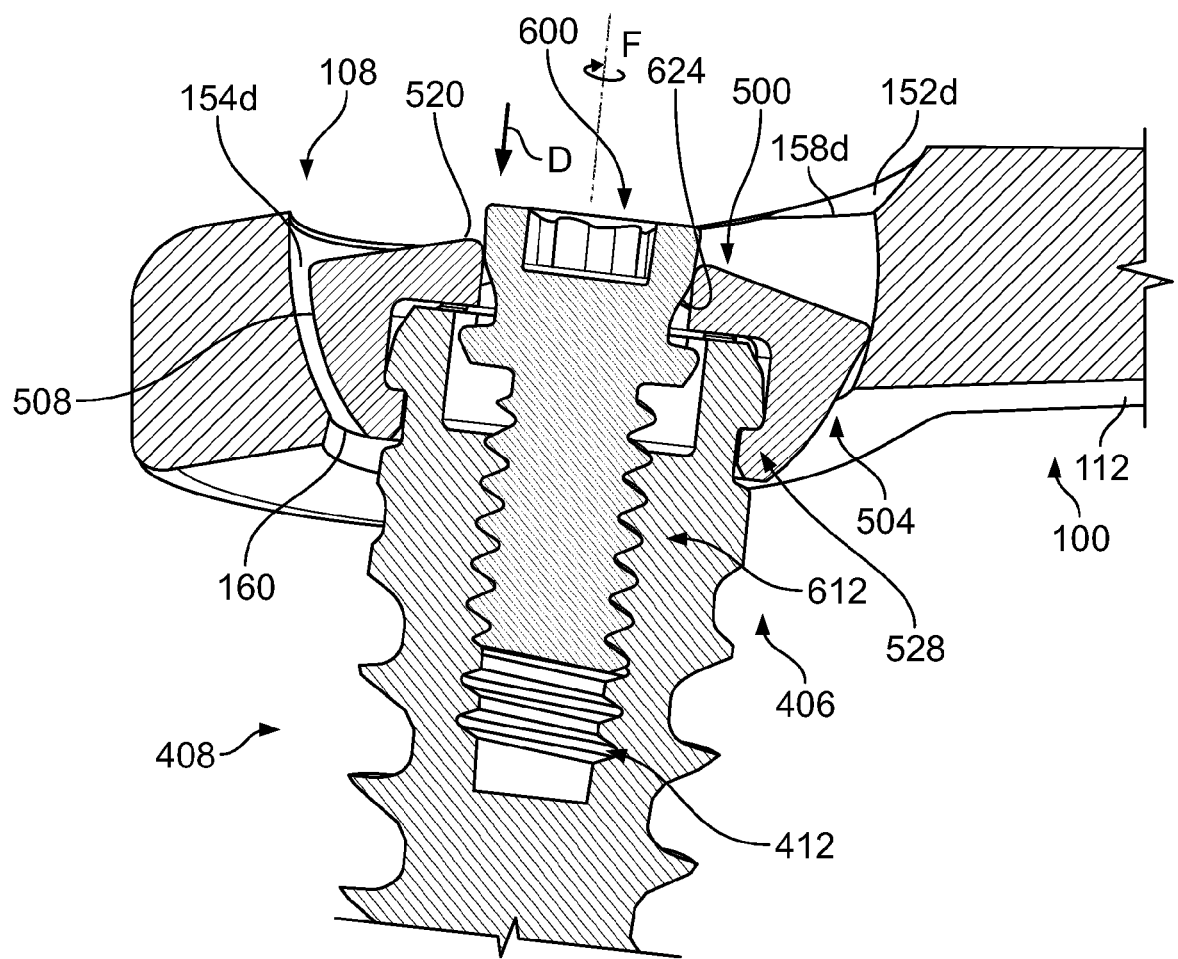
Figure 30:
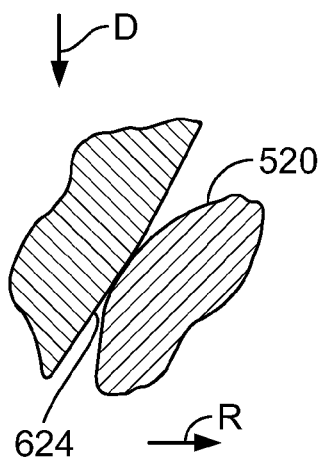

By driving the bone anchor assembly 400 into the bore 108, the locking fastener upper cam surface 624 cooperates with the locking cap radially inner upper cam surface 520 to deflect the locking cap annular wall portion 504, as shown in FIGS. 29 and 30. Specifically, the locking cap radially outer upper end portion 508 shifts radially outward in direction R into tight engagement with the bore annular surface 154d. Further, the shifting of radially outer upper end portion 508 radially outward pivots the annular wall portion so that the radially inner lower end portion 528 is shifted inward into tight engagement with the anchor head portion 406. With respect to embodiments with projections 502 and cam surfaces 524 at radially inner ends 522, driving the locking fastener 600 into the anchor head portion 406 brings the locking fastener upper cam surface 624 into contact with the cam surfaces 524 such that the projections 502 shift radially outward and expand the locking cap radially outer upper end portion 508 into tight engagement with the bore annular surface 154d.

Figure 31:
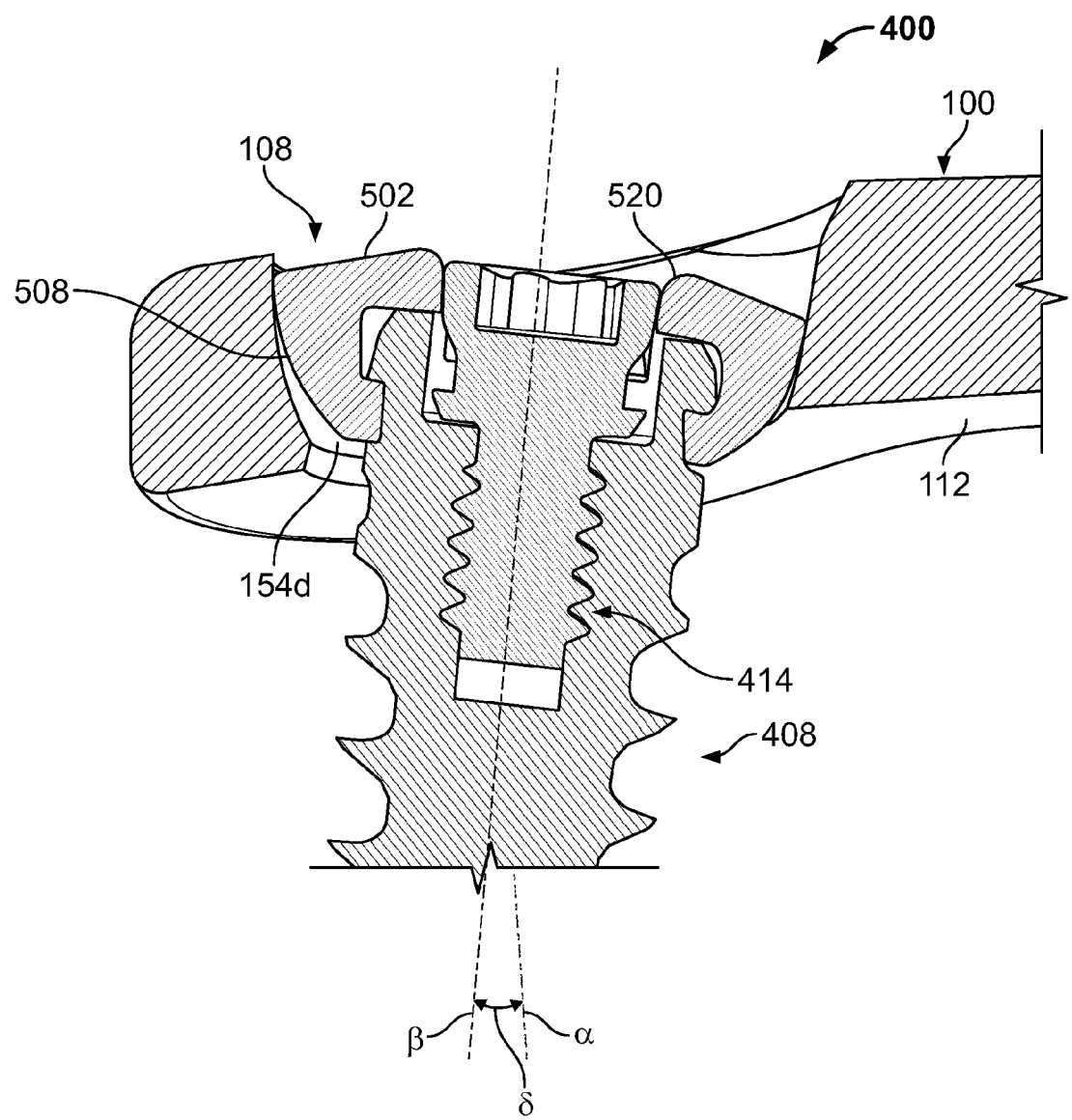

As the locking fastener 600 is driven deeper into the bone anchor 408, the locking fastener upper cam surface 624 gradually increases in size. Thus, the locking cap radially outer upper end portion 508 tends to continue to expand radially outward. However, because the bone plate 100 and bore annular surface 154d are relatively rigid, the bore annular surface 154d exerts a reactive force which resists further expansion of the locking cap 500 by way of friction against the locking fastener upper cam surface 624. Accordingly, the firmness of the engagement of the locking cap radially outer upper end portion 508 against the bore annular surface 154d may be controlled by way of the torque applied to drive locking fastener 600 into the bone anchor 408. Once a predetermined amount of torque will no longer rotate the locking fastener 600, the bone anchor assembly 400 will be fixed relative to the bone plate 100 with a correlated amount of firmness. In this manner, the locking fastener 600 generally sits proud within axial bore 412 since the locking cap radially inner upper cam surface 520 frictionally resists further rotation of fastener 600 into the axial bore 412. FIG. 31 illustrates the bone anchor assembly 400 rigidly secured at angle δ within bore 108 after the locking fastener 600 has been driven into the bone anchor 408 a predetermined distance to provide the desired engagement of the locking cap radially outer upper end portion 508 against the annular surface 154d.

Two additional bone plate system embodiments 1010, 2010 are shown in FIGS. 32-42. Bone plate system embodiments 1010, 2010 may include bone anchor assembly 400 or an alternative embodiment, bone anchor assembly 1400. Bone plate system embodiments 1010, 2010 are similar to the bone plate system 10 in that preassembled bone anchor assemblies 400, 1400 may be polyaxially driven through bores in the bone plates 1100, 2100 and fixed at an angle relative to the bone plates 1100, 2100. Additionally, the bone anchor assemblies 400, 1400 have locking fasteners 600, 1600 that are driven into bone anchor head portions 406, 1406 to expand locking caps 500, 1500 carried thereon.

Figure 32:
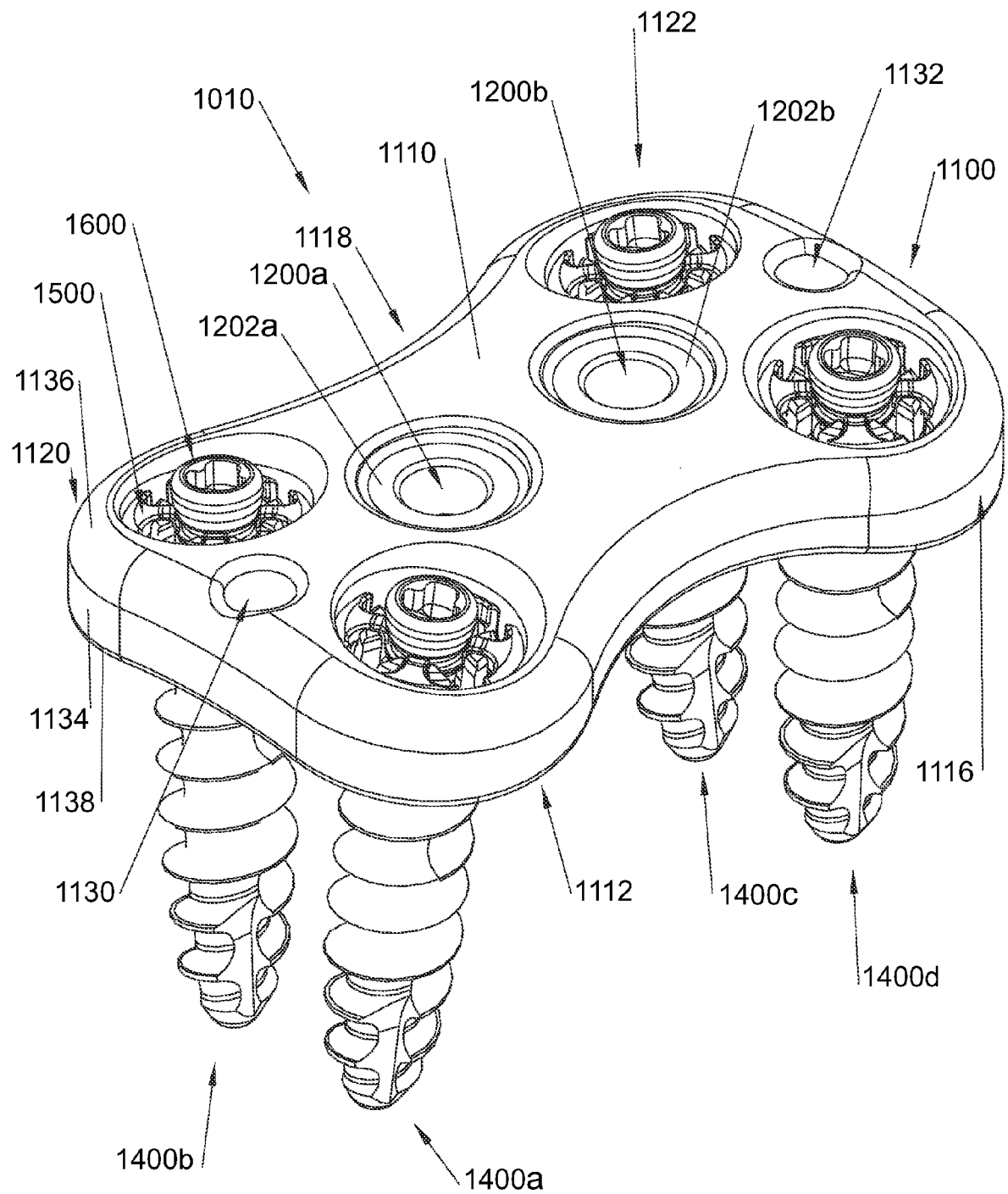
FIG. 32 is a perspective view of another bone plate system in accordance with the present invention including a bone plate and bone anchor assemblies.

Bone plate system 1010 has an elongated bone plate 1100 with a dog-bone shape similar to the bone plate 100, as shown in FIG. 32. The bone plate 1100 has upper and lower surfaces 1110 and 1112 and a sidewall 1116 extending about the periphery of the bone plate 1100. The bone plate 1100 generally has a narrow middle portion 1118 and wider opposing ends 1120, 1122. Preferably, the middle portion 1118 has a width of 19 mm and the opposing ends 1120, 1122 have a width of 26 mm. Further, the bone plate 1100 preferably has a thickness of 3.5 mm at the middle portion 1118 and a thickness of 5.0 mm at the opposing ends 1120, 1122. The sidewall 1116 may include a generally flat outer surface 1134 and upper and lower curved outer surfaces 1136, 1138 that form a smooth transition between the generally flat outer surface 1134 and the bone plate upper and lower surfaces 1110, 1112. To aid in installation, the bone plate 1100 includes installation tool bores 1200a, 1200b that receive the expanding ends of an installation tool (not shown). Flat annular surfaces 1202a, 1202b are provided about the bores 1200a, 1200b to permit the installation tool to firmly abut the flat annular surfaces 1202a, 1202b and maintain a secure connection between the tool and the bone plate 1100.

The bone plate 1100 also has temporary holding pin bores 1130, 1132 positioned at the outermost ends 1120, 1122 of the bone plate 1100. If the bone plate 1100 is placed on two adjacent vertebral bodies, the separation of the holding pin bores 1130, 1132 permits the holding pins to be placed away from the end plates of the vertebral bodies, which would be positioned toward the middle of the bone plate 1100. Further, using bore 1130, 1132 limits movement of the bone plate 1100 away from the temporary holding pins even if there is only one pin used to temporarily maintain the bone plate 1100 against the bone.

Figure 33:
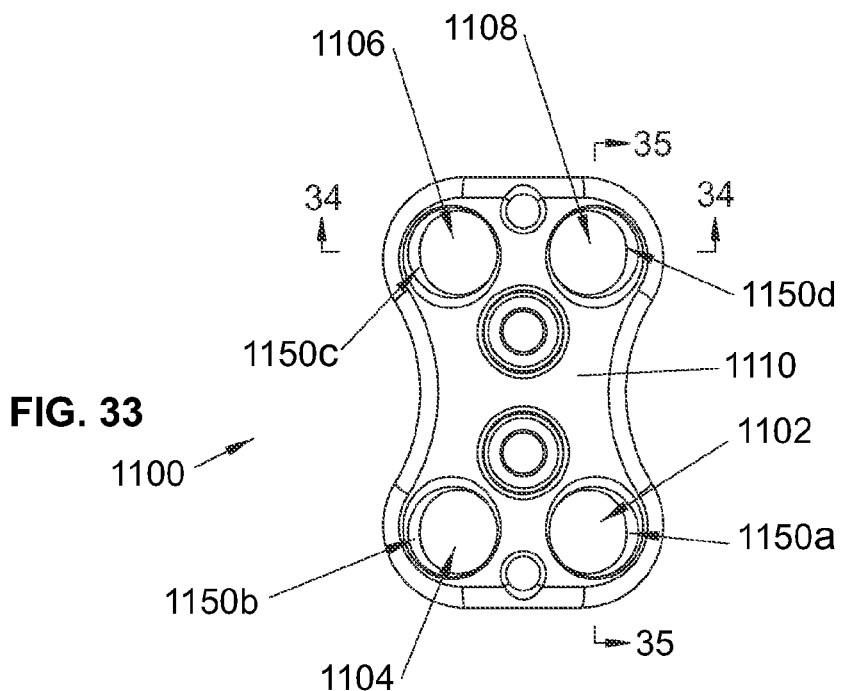
FIG. 33 is a plan view of the bone plate of FIG. 32 showing sidewalls of the bone plate through bores.
Figure 34:
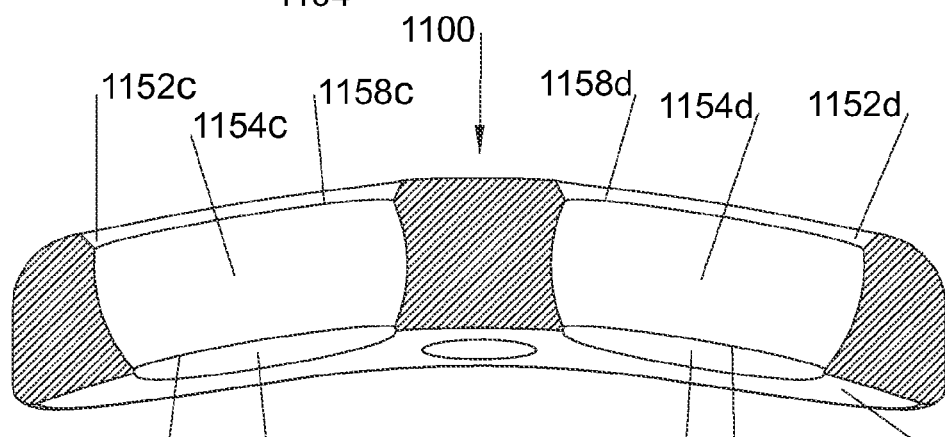
FIG. 34 is a cross-sectional view taken across line 34-34 of FIG. 33 showing an annular surface of the bone plate through bores.
Figure 35:
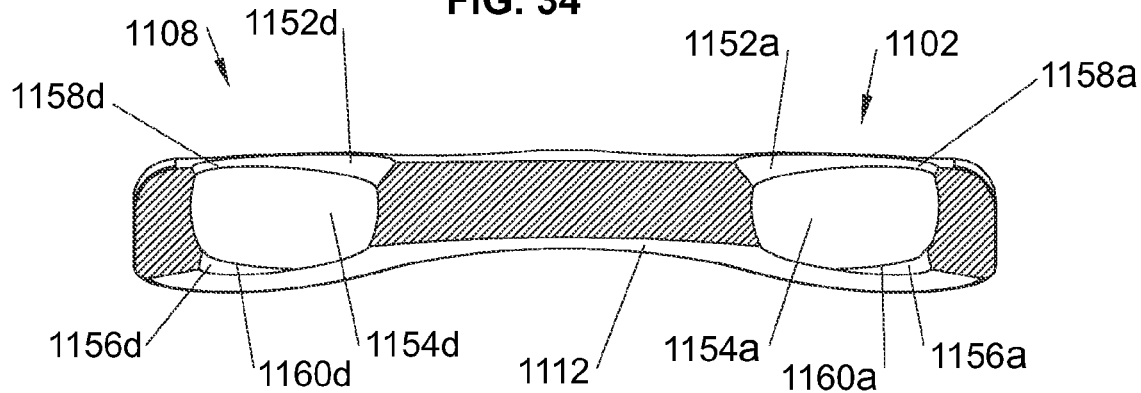
FIG. 35 is a cross-sectional view taken across line 35-35 of FIG. 33 showing upper and lower chamfered surfaces of the bone plate through bores.

Positioned at the corners of the bone plate 1100 are through bores 1102, 1104, 1106, and 1108, as shown in FIG. 33. The bone plate 1100 includes bore sidewalls 1150a, 1150b, 1150c, and 1150d that generally define a respective bore. Like the sidewalls 150 of bone plate 100, each bore sidewall 1150 includes an upper chamfer 1152, an upper lip 1158, a bore annular surface 1154, a lower lip 1160, and a lower chamfer 1156, as shown in FIGS. 34 and 35. The upper chamfer 1152 provides clearance for a bone anchor assembly 1400 as it is inserted into, for example, bore 1108. The upper chamfer 1152 generally tapers radially inward to upper lip 1158d, which has a smaller diameter to resist back out of the bone anchor assembly 1400. The bore annular surface 1154d forms a generally spherical pocket that the locking cap 1500 expands into contact with to fix the bone anchor assembly 1400 within the bore 1108. The lower lip 1160d preferably has a smaller diameter than the upper lip 1158d so that the lower lip 1160d restricts the bone anchor assembly 1400 from passing completely therethrough.

Figure 36:
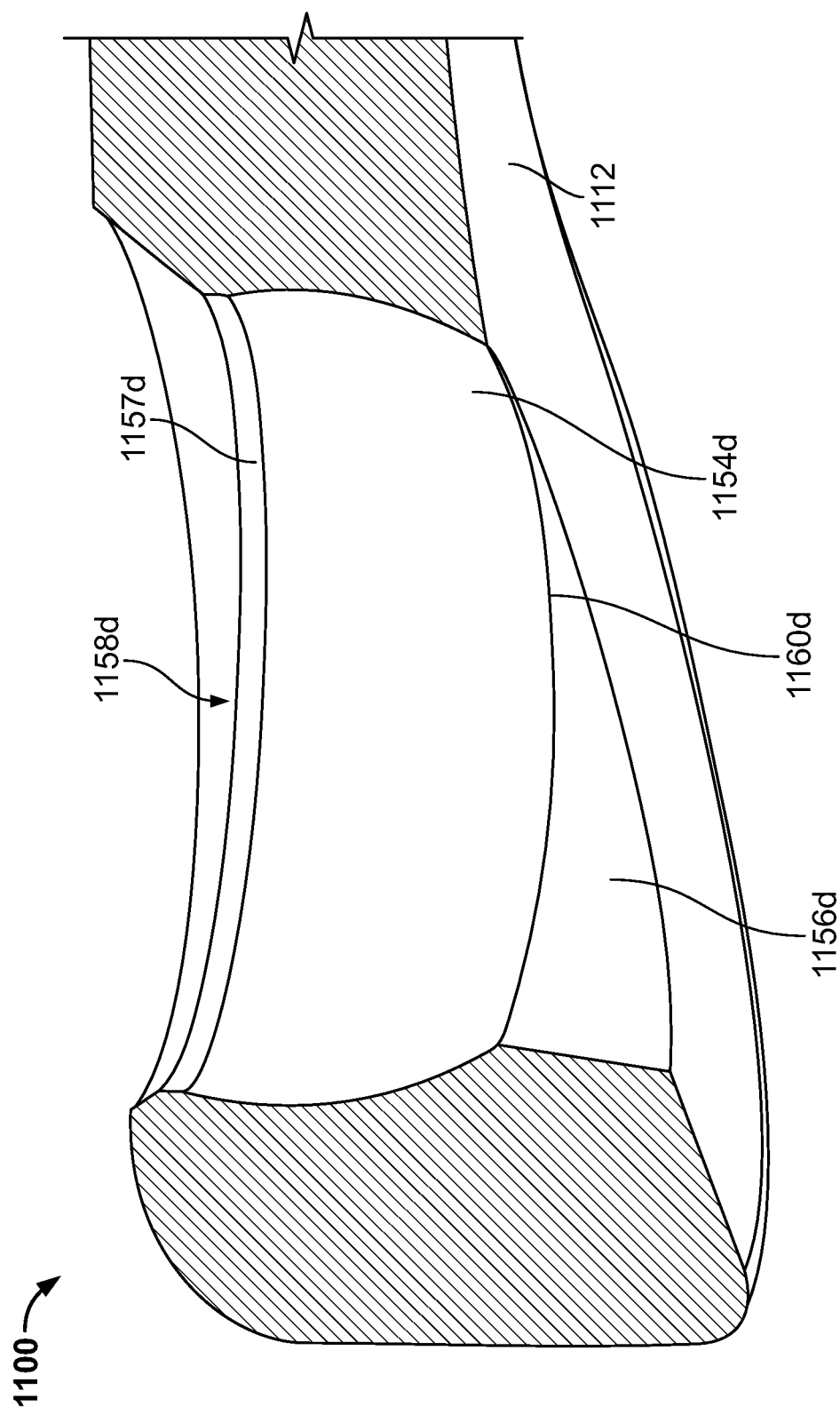
FIG. 36 is a cross-sectional view of an alternative embodiment of an upper lip of a bone plate bore.

In some instances, the procedure of driving the bone anchor assembly 1400 and the contact of the locking cap 1500 against the bone plate 1100 may damage the bones sought to be fused. Here, it may be desirable to reduce the interference between the upper lip 1158 and the locking cap 1500. A preferred embodiment that addresses this issue is shown in FIG. 36. Specifically, the upper lip 1158 includes a flat annular wall 1157d positioned above the bore annular surface 1154d. In this embodiment, the upper lip 1158d effectively has a larger opening so that the bone anchor assembly 1400 may pass through with less interference between the locking cap 1500 and the bone plate 1100. One downside to this configuration is that the increased size of upper lip 1158d decreases the amount lip 1158d projects over the locking cap 1500 which reduces the ability of the lip 1158d to resist back-out of bone anchor assembly 1400. This configuration of upper lip 1158 may be used in any bone plate system embodiment.

Figure 37:
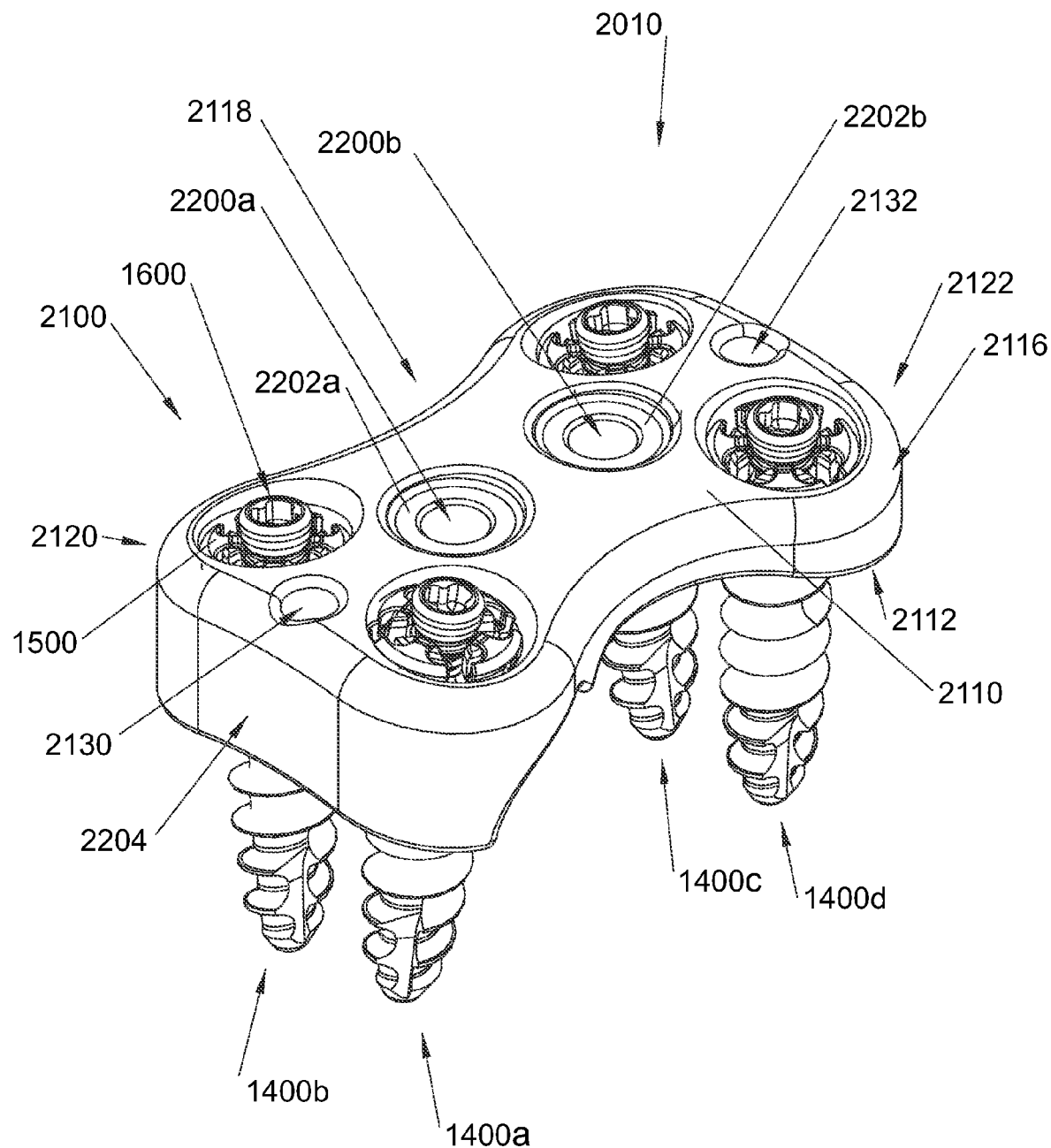
FIG. 37 is a perspective view of another bone plate system in accordance with the present invention including a bone plate and bone anchor assemblies.

Turning now to FIG. 37, bone plate system 2010 includes a bone plate 2100 that is similar in many respects to bone plate 1100. For example, bone plate 2100 has upper and lower surfaces 2110, 2112 and a sidewall 2116 extending around the periphery of the bone plate 2100. Preferably, the sidewall 2116 is curved to limit interference with soft tissues. The bone plate 2100 also has a dog-bone shape with a narrow middle portion 2118 and wider opposing ends 2122. In a preferred embodiment, the middle portion 2118 has a width of 19 mm and the opposing ends have a width of 26 mm. To aid in installation, the bone plate 2100 has temporary installation tool bores 2200a, 2200b configured to receive the expanding ends of an installation tool (not shown) and flat annular surfaces 2202a, 2202b to provide a flat abutting surface for the installation tool. Additionally, the bone plate 2100 has temporary holding pin bores 2130, 2132 positioned at the outermost ends 2120, 2122 of the bone plate 2100.

Figure 38:
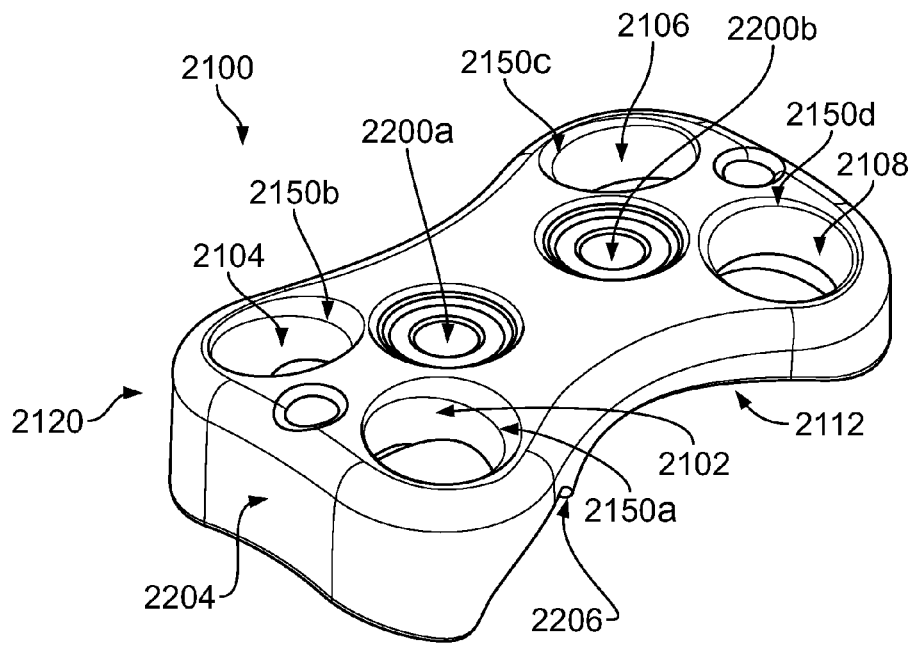
FIG. 38 is a perspective view of the bone plate of FIG. 37 showing a lower projection at one end of the bone plate.
Figure 39:
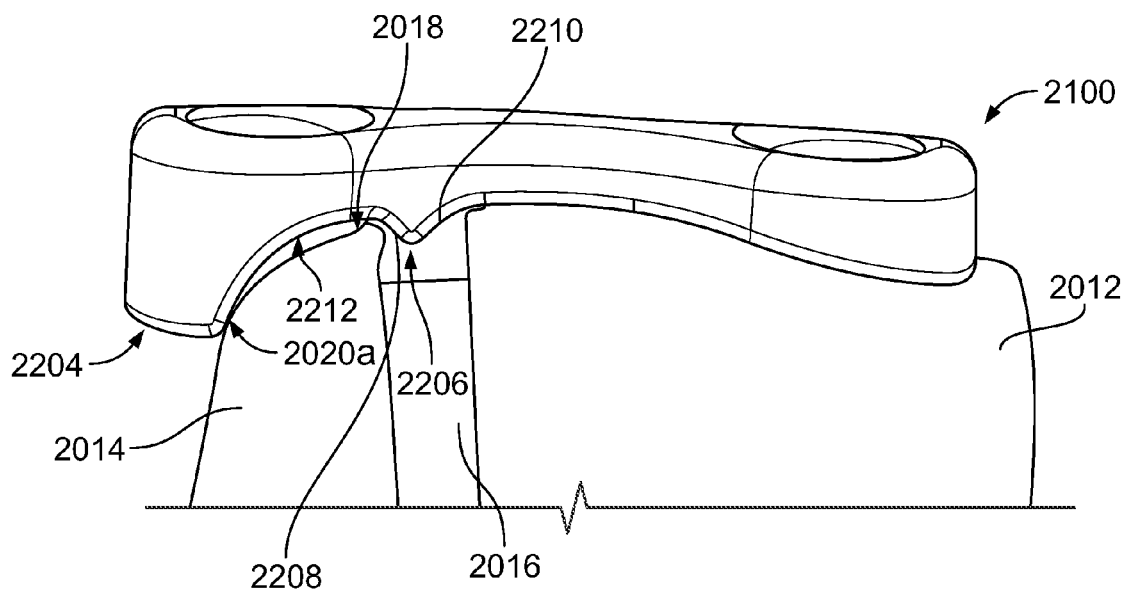
FIG. 39 is a side elevational view of the bone plate of FIG. 37 showing the bone plate mounted on anterior surfaces of S1 and L5 vertebrae.
Figure 40:
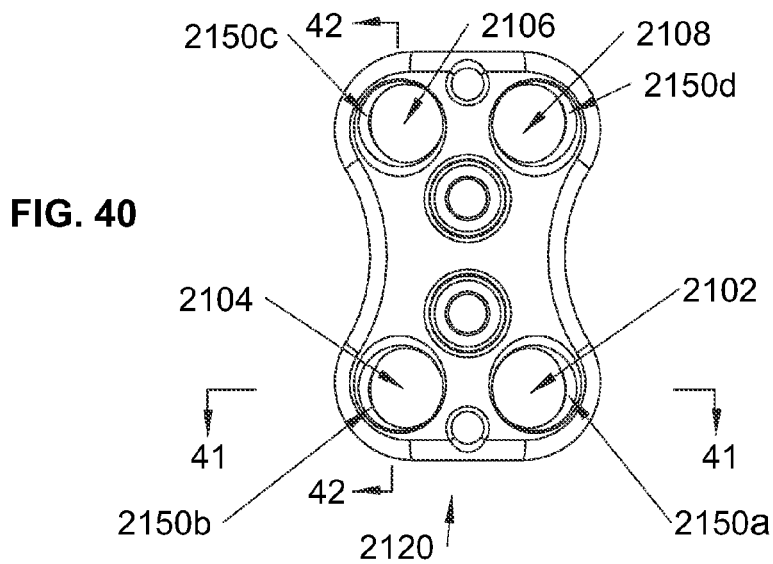
FIG. 40 is a plan view of the bone plate of FIG. 37 showing sidewalls of the bone plate through bores.

One difference between bone plates 2010 and 1010 is the presence of a lower projection 2204 on bone plate 2010. As shown in FIGS. 38 and 39, the bone plate 2100 has lower projection 2204 and a seating projection 2206 extending from the bone plate lower surface 2112. The seating projection 2206 is spaced from the lower projection 2204 such that the bone plate 2100 may be positioned on the L5 vertebra 2012 and the S1 vertebra 2014 with the seating projection 2206 resting on a sacral promontory 2018 and the lower projection 2204 contacting the S1 vertebra 2014. With respect to the seating projection 2206, the temporary installation tool bore 2200a may intersect the seating projection 2206 such that the seating projection 2206 is comprised of two aligned, spaced portions extending laterally across the bone plate 2100. Further, the seating projection 2206 may include a flat inclined surface 2208 for contacting the sacral promontory 2018 and a curved inclined surface 2210 that generally faces the L5 vertebra 2012.

Figure 41:
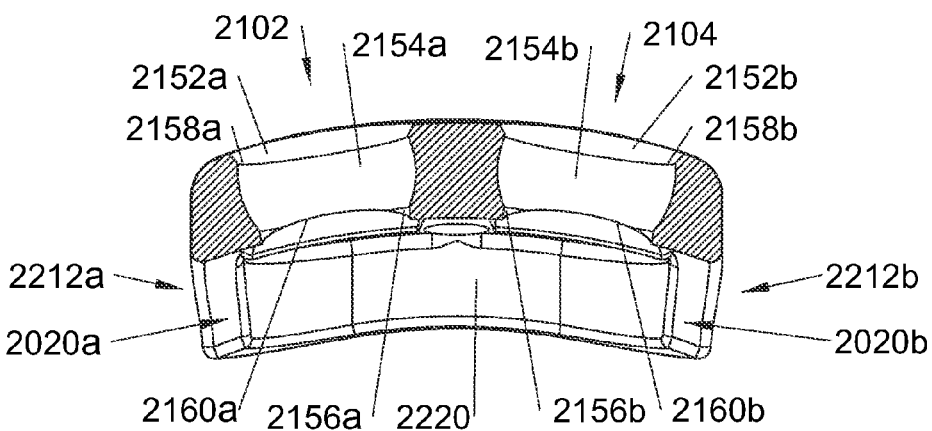
FIG. 41 is a cross-sectional view taken across line 41-41 of FIG. 40 showing undercuts of the lower projection.

The lower projection 2204 extends from the bone plate 2100 at end 2120 and is generally curved about the longitudinal axis of the bone plate 2100 to conform to bone surfaces, as shown in FIGS. 39-42. The lower projection 2204 includes an undercut 2212 inclined away from the bone plate lower surface 2112 that increases in height heading away from the seating projection 2206. An inner wall portion 2220 extends between the undercuts 2212a, 2212b and has a curvature that matches bone plate end 2120. In a preferred form, the undercut 2212 is dimensioned such that the lower projection 2204 contacts the S1 vertebra at points 2020a, 2020b which are laterally spaced from each other on the lower projection 2204, as shown in FIGS. 39 and 41.

The bone plate 2100 includes bores 2102, 2104, 2106, and 2108 that are each preferably configured to receive bone anchor assemblies 1400 that are polyaxially driven therethrough. The bone plate 2100 has bore sidewalls 2150 that each define a bore and include an upper chamfer 2152, an upper lip 2158, a bore annular surface 2154, a lower lip 2160 and a lower chamfer 2156. The sizing and configuration of the sidewalls 2150 are similar to the embodiments of bone plates 100 and 1100 and provide similar functionality with respect to receiving and retaining bone anchor assemblies.

Figure 43:
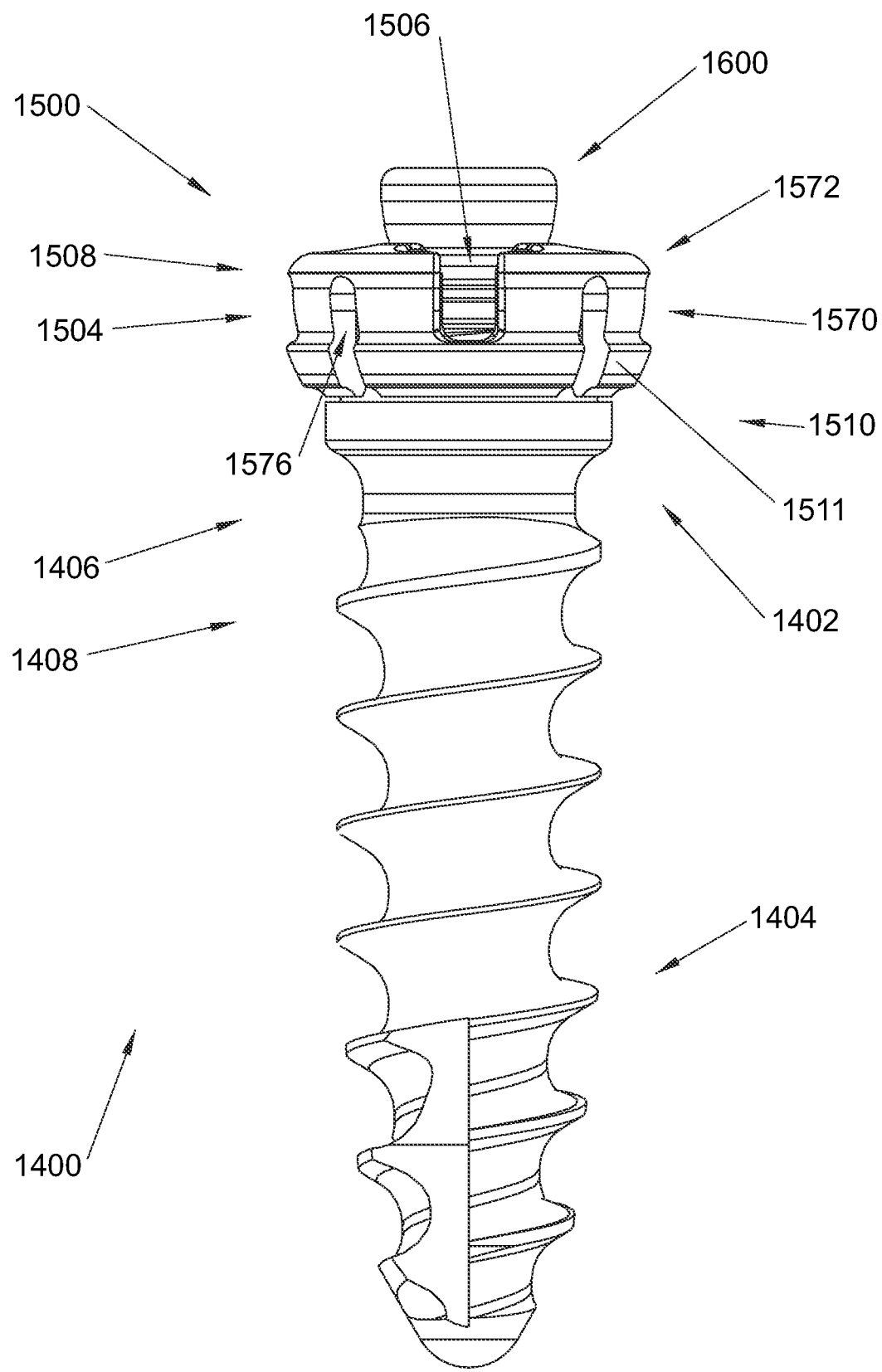
FIG. 43 is an elevational view of one of the bone anchor assemblies of FIG. 37 including a bone anchor, a locking cap, and a locking fastener.

As shown in FIG. 43, bone anchor assembly 1400 is another embodiment of a preassembled bone anchor that may be used in any of the bone plate system embodiments disclosed herein. Bone anchor assembly 1400 has a shank end 1404 that may have a number of different configurations, including a screw, a relatively smooth shank, or even a threaded configuration for engaging a member disposed in bone. In a preferred form, shank end 1404 is a self-tapping bone screw. The bone anchor assembly 1402 has an opposing driving end 1402 that is configured to be driven into a bone plate through bore.

The bone anchor assembly 1400 includes a bone anchor 1408 having a bone anchor head portion 1406 with a locking cap 1500 mounted thereon. A locking fastener 1600 is connected to the anchor head portion 1406 when the bone anchor assembly 1400 is in a preassembled configuration. Further, the locking fastener 1600 is driven into the anchor head portion 1406 to expand the locking cap 1500 and fix the bone anchor assembly 1400 within a bone plate bore.

Though the locking cap 1500 is similar to the locking cap 500, there are several differences between the two embodiments. Generally, the locking cap 1500 has an annular wall portion 1504 that extends axially along the bone anchor head portion 1406 with the locking cap 1500 carried on the anchor head portion 1406. However, instead of a C-ring design, the locking cap 1500 includes a plurality of close-ended upper and lower slots 1506, 1576 axially extending along the locking cap 1500. The plurality of slots 1506, 1576 permit portions of the locking cap 1500 to flex inwardly and outwardly as required to accept the anchor head portion 1406 and to fix the bone anchor assembly 1400 within a bone plate bore, as will be discussed below. By using a number of lower slots 1576, expansion of the locking cap 1500 is more evenly distributed around the locking cap 1500, thereby minimizing stress concentrations which could potentially yield the locking cap 1500 material. Additionally, it has been found that using a number of lower slots 1576 increases the retention load of the locking cap 1500 on the anchor head portion 1406. A greater retention load tends to keep the locking cap 1500 on the anchor head portion 1406 despite interference with, for example, upper lip 2158*b* as the bone anchor assembly 1400 is driven into bore 2104.

Figure 42:
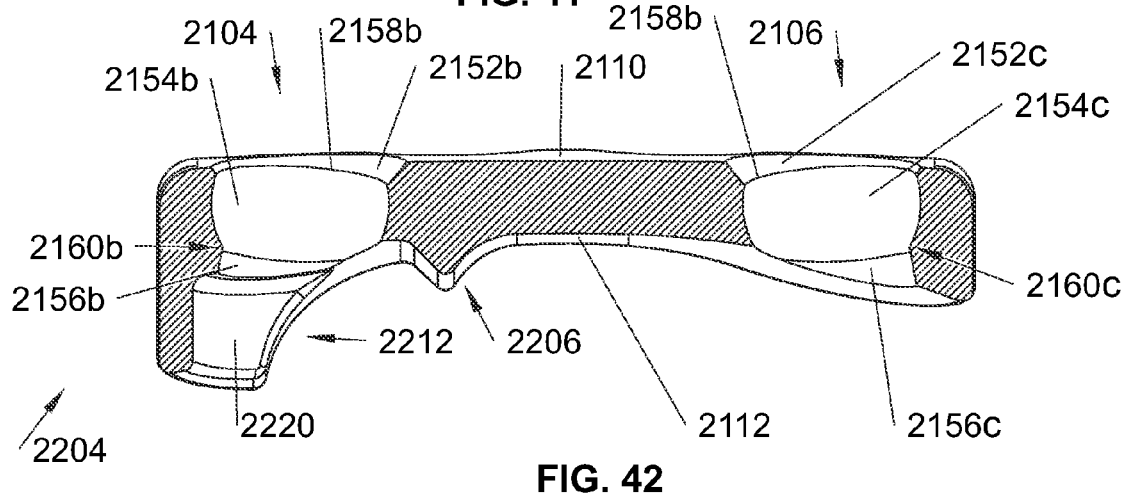
FIG. 42 is a cross-sectional view taken across line 42-42 of FIG. 40 showing an annular surface and upper and lower chamfered surfaces of the bone plate through bores.

With continued reference to FIG. 43 and the bone plate system 2010 of FIG. 42, the locking cap annular wall 1504 includes a lower radially raised arcuate outer surface portion 1510 configured for engaging the bone plate annular surface 2154. Preferably, the outer surface portion 1510 includes a plurality of outer surfaces 1511 that are separated by the lower slots 1576 and are complimentary to the bone plate bore annular surface 2154. This way, the outer surface portion 1510 tends to shift the locking cap annular wall 1504 radially inward as the bone anchor assembly driving end 1402 is seated within a bone plate bore. Also, above the lower arcuate outer surface portion 1510 is a radially recessed outer surface portion 1570.

At the other end of annular wall 1504 is a radially outer upper end portion 1508 that is expanded into contact with the bore annular wall 2154. The outer upper end portion 1508 includes an upper radially raised, arcuate outer surface portion 1572 configured to engage the bore annular surface 2154. Thus, the upper and lower radially raised arcuate outer surface portions 1572, 1510 are positioned at opposite ends of the locking cap 1500 and are separated by a radially recessed outer surface portion 1570. In this manner, there is a spaced contact between the raised arcuate outer surface portions 1572, 1510 and the bore annular surface 2154.

Figure 44:
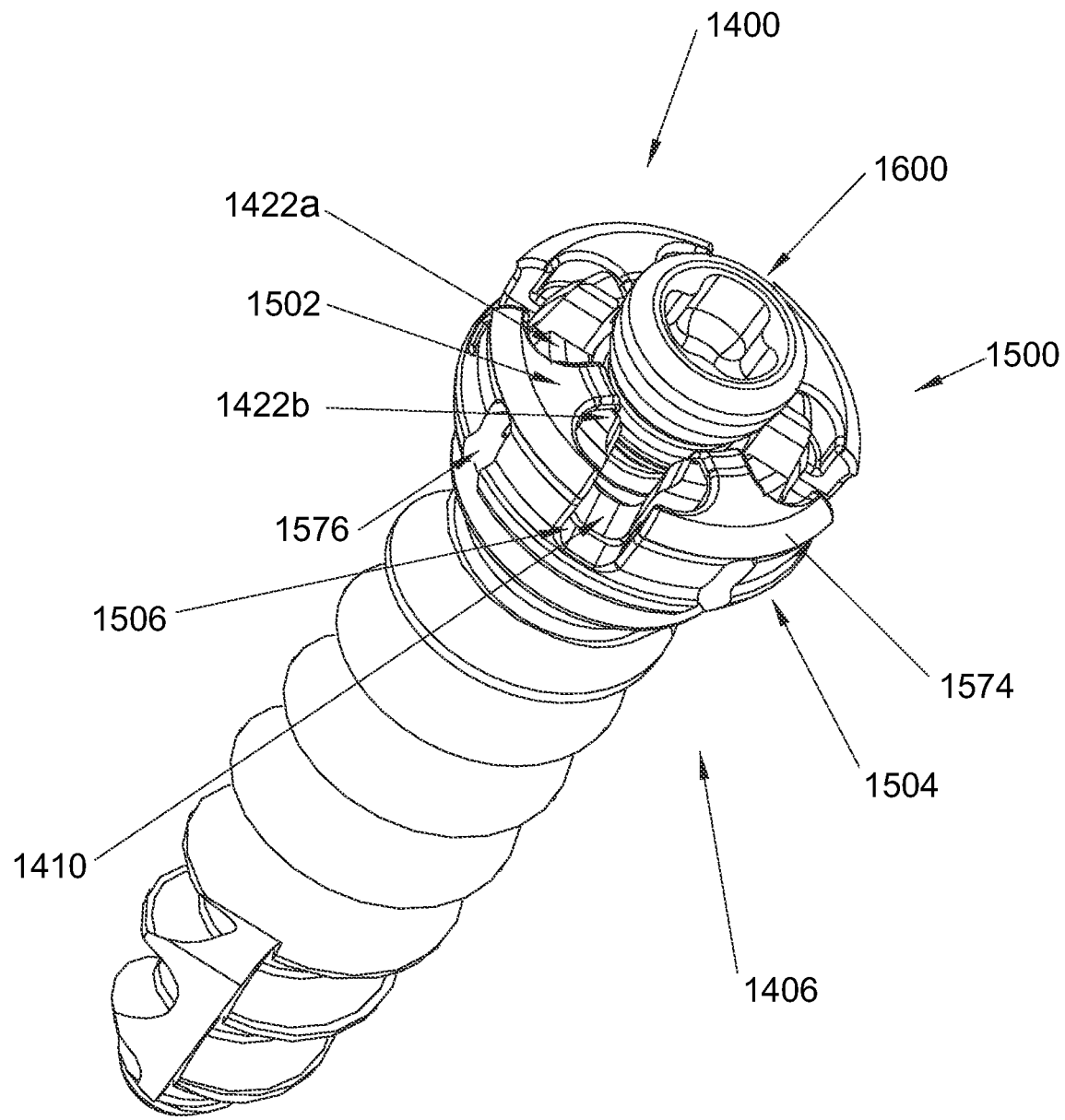
FIG. 44 is a perspective view of the bone anchor assembly of FIG. 43 showing projections of the locking cap received between bosses of a bone anchor head portion of the bone anchor.

As shown in FIG. 44, the bone anchor head portion 1406 includes a plurality of depressions 1410 that are aligned with upper slots 1506 in the locking cap 1500 when the lock cap 1500 is carried on the anchor head portion 1406. In a manner similar to bone anchor assembly 400, a driver may be inserted into contact with the depressions 1410 to drive the bone anchor assembly 1400 through a bone plate bore and into engagement with a bone without rotating the locking cap 1500 relative to the anchor head portion 1406. In one embodiment, the locking cap 1500 also has projections 1502 that extend radially inward from the locking cap annular wall 1504. Further, the anchor head portion 1406 may have axially upwardly projecting bosses 1422*a*, 1422*b* that receive one of the projections 1502 therebetween to resist rotation of the locking cap 1500. The locking cap 1500 may also have a plurality of circumferentially extending shoulders 1574 spaced by the upper slots 1506 that are expanded into contact with the bore annular surface 2154 and may contact the bore upper lip 2158 to resist back out of bone anchor 1408.

Figures 45, 46:
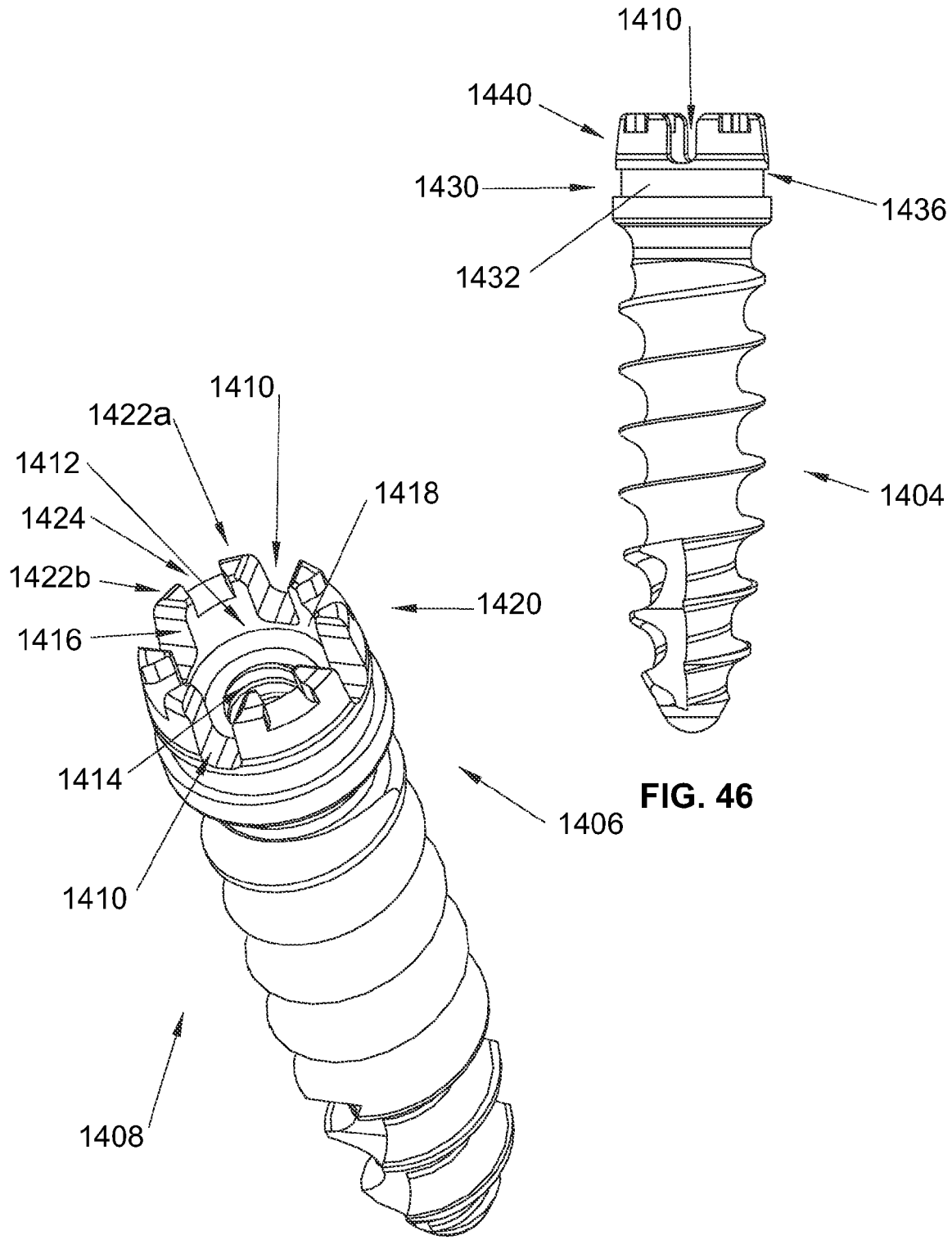
FIG. 45 is a perspective view of the bone anchor of FIG. 43 showing a bore extending axially through a portion of the bone anchor.
FIG. 46 is an elevational view of the bone anchor of FIG. 43 showing a channel formed in the bone anchor head portion.

The bone anchor head portion 1406 has a central axial bore 1412 in communication with an upper opening portion 1416 at the upper end of the bone anchor 1408. A solid wall portion 1420 of the anchor head portion 1406 may extend axially with an inner annular surface 1418 thereof defining a portion of the axial bore 1412. The axial bore 1412 may include a threaded portion 1414 for receiving a threaded shank of the locking fastener 1600. The bone anchor head portion 1406 also has a plurality of circumferentially spaced depressions 1410. As best shown in FIG. 45, the pairs of bosses, 1422*a*, 1422*b* are positioned on either side of a recess 1424 that is sized to receive one of the locking cap projections 1520.

To connect the locking cap 1500 to the bone anchor 1408, the anchor head portion 1406 includes a radially outer upper surface 1440 that becomes progressively wider approaching an annular channel 1430. The radially outer upper surface 1440 expands the locking cap 1500 over the anchor head portion 1406 before a radially inner lower end portion 1526 of the locking cap 1500 snaps into the annular channel 1430. In one embodiment, the radially outer upper surface 1440 may be conical. The annular channel 1430 includes a cylindrical inner surface 1432 and upper annular surface 1436 that are configured to restrict longitudinal movement of the locking cap 1500 along the bone anchor 1408.

Figure 47:
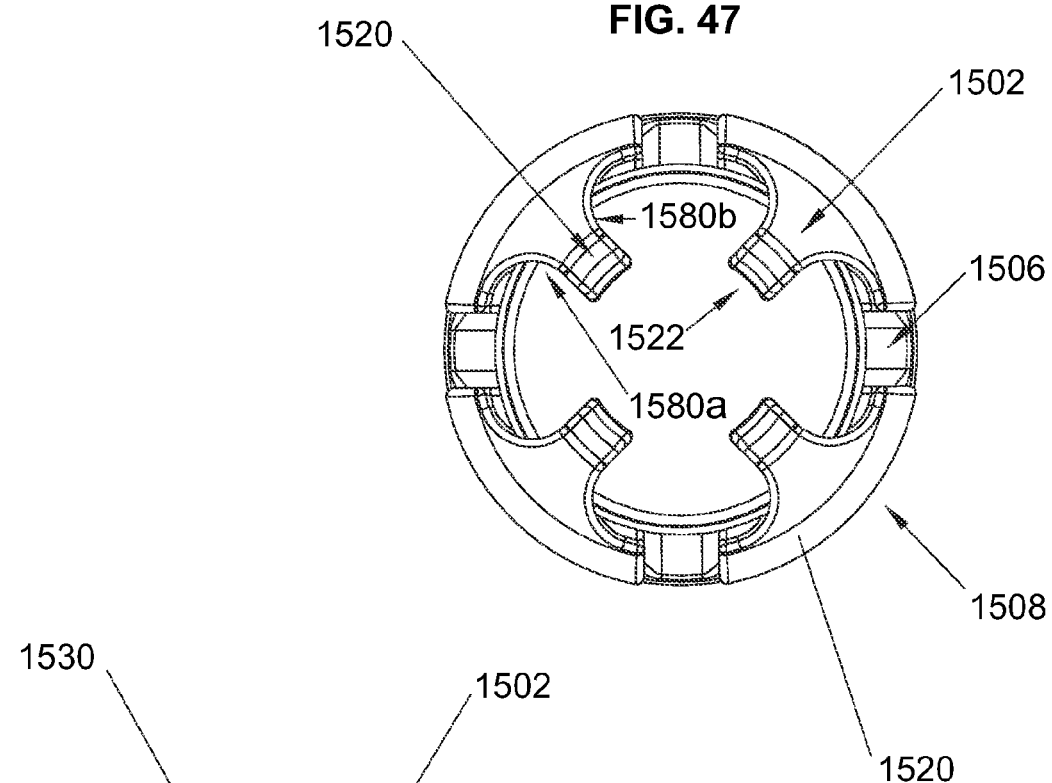
FIG. 47 is a plan view of the locking cap of FIG. 43 showing radially inner ends of the locking cap projections.
Figure 48:
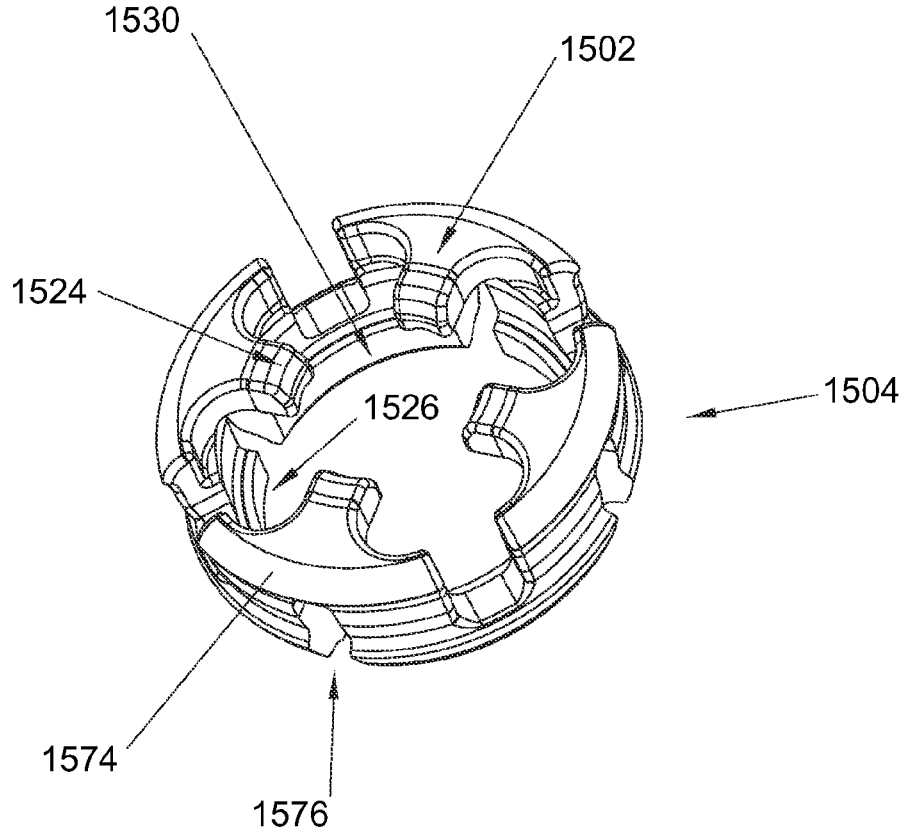
FIG. 48 is a perspective view of the locking cap of FIG. 43 showing a radially inner lower end portion of the locking cap.

With respect to the locking cap 1500, the projections 1502 include fillets 1580*a*, 1580*b* on either side thereof that reduce the width of the projections 1502, as shown in FIGS. 47 and 48. Though narrower, the projections 1502 are sufficiently strong to shift and hold the locking cap radially outer upper end portion 1508 in tight engagement with, for example, the bore annular surface 2154. The narrower projections 1502 also permit the bosses 1422*a*, 1422*b* to be larger without reducing the size of spaced depressions 1410 so that the bosses 1422*a*, 1422*b* are more rigid and resist shearing forces caused by rotation of the locking cap 1500.

The locking cap 1500 also has a radially inner upper cam surface 1520 that cooperates with the locking fastener 1600 to deflect the locking cap radially outer upper end portion 1508 radially outwardly as the locking fastener 1600 is driven into the bone anchor bore 1412. In the embodiment shown, the locking cap 1500 has projections 1502 with radial inner ends 1522 and a plurality of cam surfaces 1524 formed on the radial inner ends 1522. Here, the plurality of cam surfaces 1524 cooperate with the locking fastener 1600 to shift the projections 1502 radially outward.

As the radially outer upper end portion 1508 expands, the locking cap annular wall 1404 tends to pivot such that the radially inner lower end portion 1526 is brought into tight engagement with the bone anchor head portion 1406. In one embodiment, the lower end portion 1526 includes a plurality of circumferentially extending ribs 1530 spaced by lower slots 1576. Due to the radially inward movement of the lower end portion 1526, the ribs 1530 contract together within the bone anchor annular channel 1430 to tightly engage the anchor head portion 1406.

Figure 49:
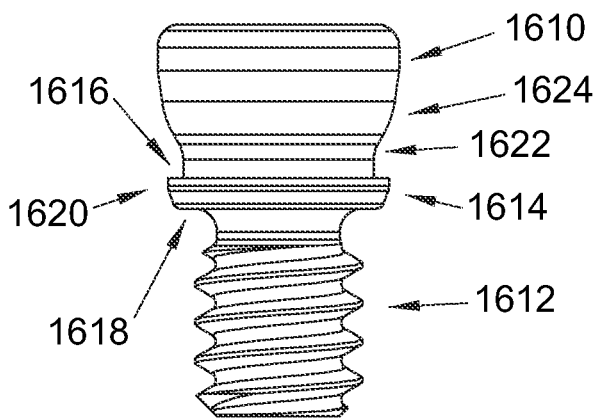
FIG. 49 is an elevational view of the locking fastener of FIG. 43 showing an annular collar and narrow portion of the locking fastener.
Figure 50:
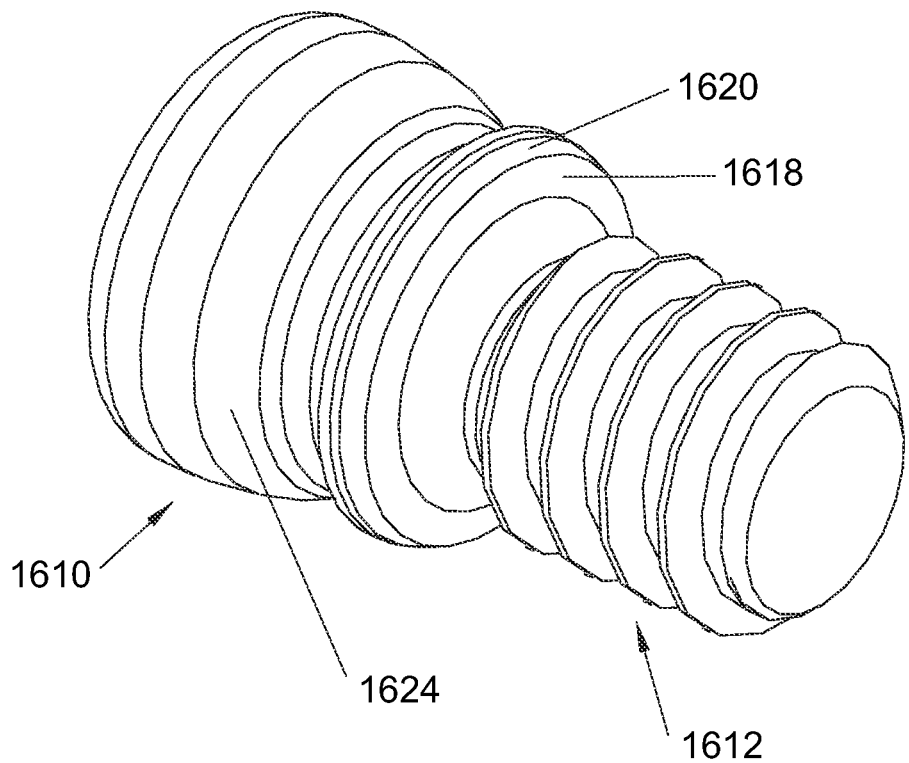
FIG. 50 is a perspective view of the locking fastener of FIG. 43 showing radially outer cam surfaces of the locking fastener.
Figure 51:
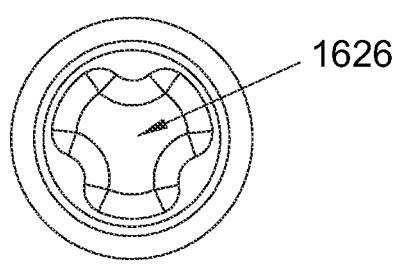
FIG. 51 is a plan view of the locking fastener of FIG. 43 showing a bore configured to receive a driver.

The locking fastener 1600 is similar to the locking fastener 600, as is apparent from FIGS. 49-51. The locking fastener 1600 includes a fastener shank 1612 that may be threaded, an annular collar 1614, and an enlarged upper head portion 1610. A narrow portion 1622 is positioned between the collar 1614 and the head portion 1610 and is aligned with the locking cap radial inner ends 1522 when the locking fastener 1600 is connected to the bone anchor member 1406 at an intermediate axial position. There is preferably a gap spacing between the narrow portion 1622 and the radially inner ends 1522 to permit the projections 1502 to shift radially inward due to contact of the locking cap annular wall 1504 with the bone plate 100, 1100, or 2100 during insertion of the bone anchor assembly 1400 into a bone plate through bore.

Another similarity is that the locking fastener annular collar 1614 includes a flat upper surface 1616 that is in confronting overlapping relation with a lower surface of the projections 1502 when the locking fastener 1600 is in the intermediate axial position. To reach the intermediate axial position, the annular collar radially extending lower cam surface 1620 cooperates with the locking cap radially inner upper cam surface 1520 to shift the upper cam surface 1520 or in some embodiments, shifts the projections 1502, out of the path of the locking fastener. Additionally, the annular collar 1614 has a radially extending upper cam surface 1620 that cooperates with the locking cap radially inner upper cam surface 1520 to expand the locking cap radially outer upper end portion 1508 into engagement with the bore annular surface 154, 1154, or 2154.

One difference between the locking fasteners 600, 1600 is that locking fastener 1600 has a driver bore 1626 for receiving a three-lobed bore. This is the preferred approach, as using a higher number of lobes requires smaller corresponding features within the bore that may shear off during rotation.

Given the similar designs of bone anchor assemblies 400, 1400, the methods of assembling bone anchor assembly 1400 into the preassembled configuration wherein the locking cap 1500 and locking fastener 1600 are connected to the bone anchor 1408 are substantially similar. Likewise, the process of driving the bone anchor assembly 1400 into a through bore of bone plates 10, 1010 or 2010 and fixing the bone anchor assembly 1400 therein is similar to the process disclosed with respect to bone anchor assembly 400.

Figure 52:
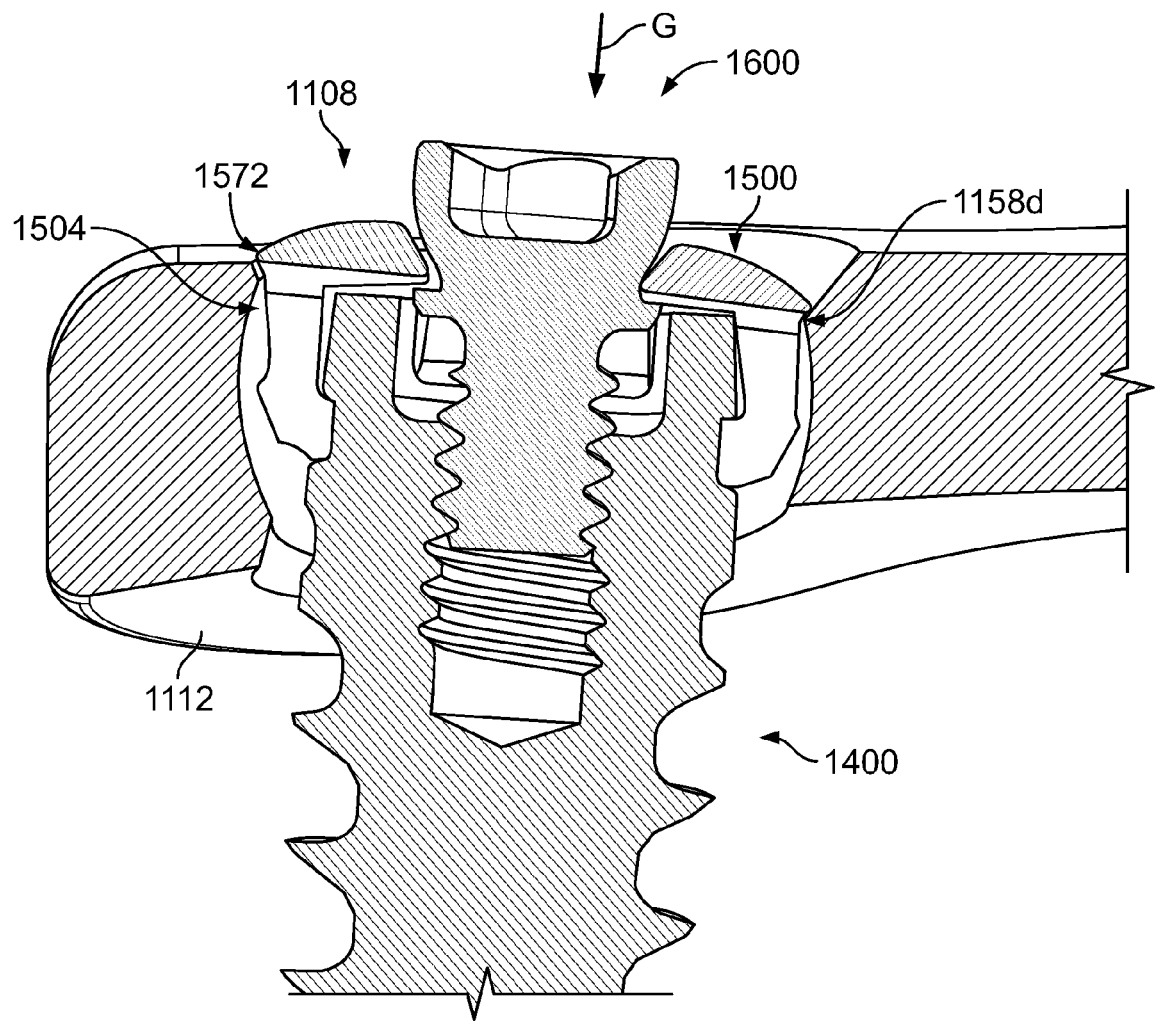
FIG. 52 is a cross sectional view of the bone anchor assembly and bone plate of FIG. 37 showing a locking cap annular wall portion contacting the bone plate and shifting a radially inner upper cam surface of the locking cap radially inward.
Figure 53:
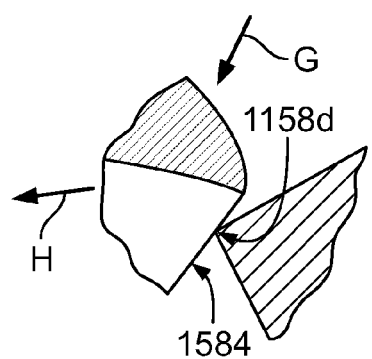
FIG. 53 is an enlarged view of FIG. 52 showing the contact between an upper lip of the bone plate through bore and the locking cap annular wall portion.

However, in one embodiment, the upper radially raised, arcuate outer surface portion 1572 of the locking cap 1500 includes a lower cam surface 1584, as shown in FIGS. 52 and 53. As the bone anchor assembly 1400 is driven into bone plate bore 1108, the lower cam surface 1584 cooperates with the upper lip 1158d and shifts the radially outer upper end portion 1508 radially inward. Once the locking cap upper end portion 1508 passes the upper lip 1158d, the upper end portion 1508 shifts radially outward before being fixed into position by set screw 1600.

The components of bone plate system embodiments 10, 1010, 2010 are preferably made from titanium alloy. The locking caps 500, 1500 are preferably resilient to deflect and expand as required, yet strong enough to fixedly maintain the bone anchor assemblies 400, 1400 within the bone plates 100, 1100, 2100. It is appreciated that a number of other materials may be acceptable for the different components of the bone plate system embodiments. These materials preferably have a high strength-to-weight ratio, are biocompatible, and are sufficiently durable to potentially remain within the patient for an extended period of time. Metallic alloys and polymers including polyetheretherketone (PEEK) are also contemplated for use as one or more components of the bone plate system embodiments.

Figure 54:
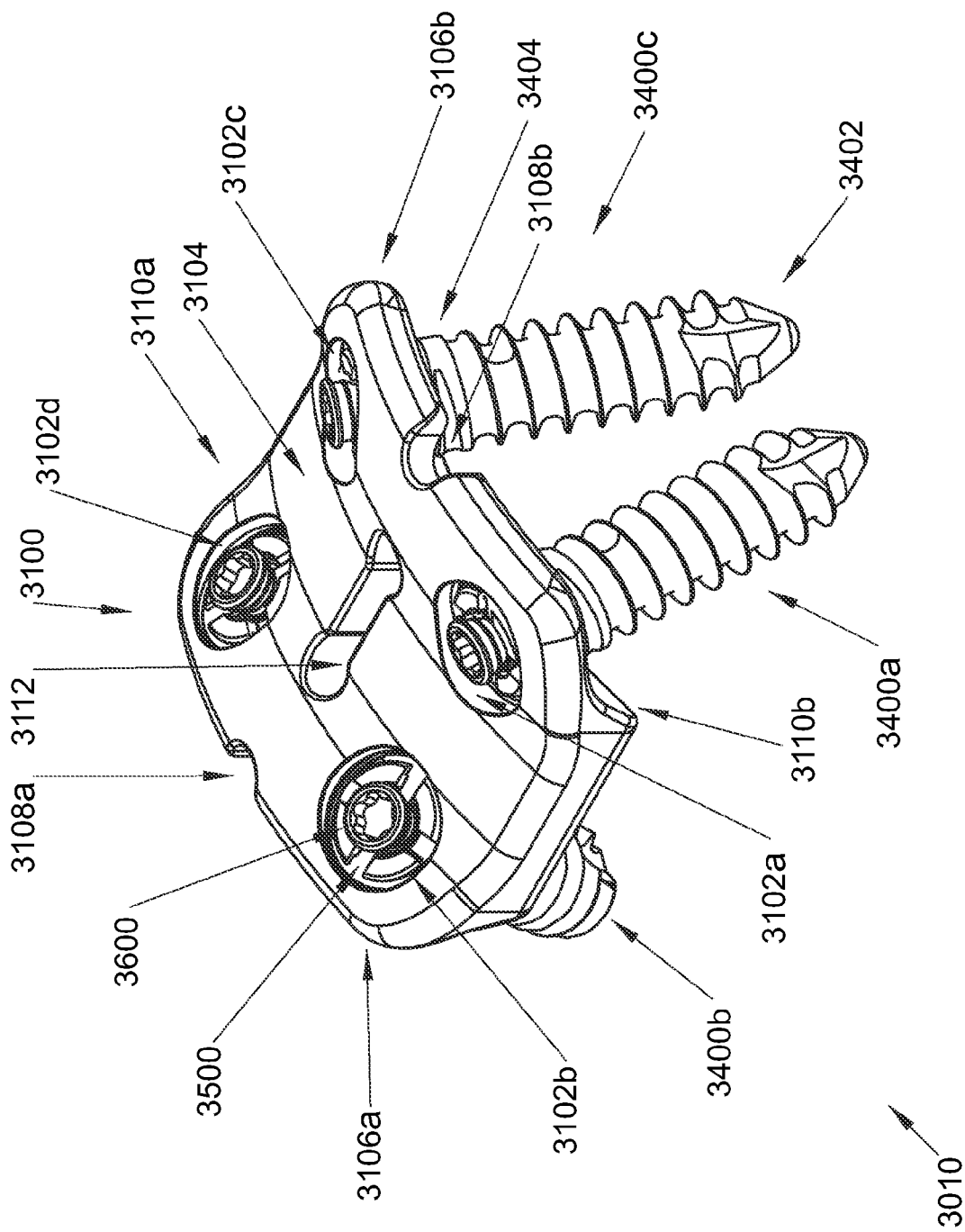
FIG. 54 is a perspective view of another bone plate system in accordance with the present invention including a bone plate and bone anchor assemblies.

In FIG. 54, another embodiment of a bone plate system 3010 is presented. Bone plate system 3010 includes a bone plate 3100 and a plurality of bone anchor assemblies 3400 received within through bores 3102 of the bone plate 3100. The bone plate system 3010 has a relatively short profile and in one embodiment is configured to partially extend into the intervertebral space between vertebra. Further, the bone plate system 3010 preferably includes a general V-shape which positions the bone anchor assemblies 3400 at an angle relative to the vertebrae so that the bone anchor assemblies 3400 may be driven diagonally into the corner of each vertebra.

Each bone anchor assembly 3400 includes a bone anchor 3402, a locking cap 3500 carried on the bone anchor 3402, and a locking fastener 3600 engaged with a bone anchor head portion 3404. Preferably, the bone anchor assembly 3400 is preassembled and ready to be driven through a bone plate through bore 3102 and into a bone. Once the bone anchor head portion 3404 is received within the bore 3102, the locking fastener 3600 is driven axially further into the bone anchor head portion 3404 to expand the locking cap 3500 and resist back out of the bone anchor assembly 3400 from the bore 3102.

More specifically, the bone plate 3100 has a relatively thick middle portion 3104 between opposing ends 3106a, 3106b. At the ends 3106a, 3106b there are corresponding temporary pin notches 3108a, 3108b. Also near the ends are transition portions 3110a, 3110b that transition between the relatively thick middle portion 3104 to the thinner ends 3106. Bone plate 3100 also has a tool insertion bore 3112 where an insertion tool with an expandable end is preferably connected to position the bone plate 3100 on bone.

Figure 55:
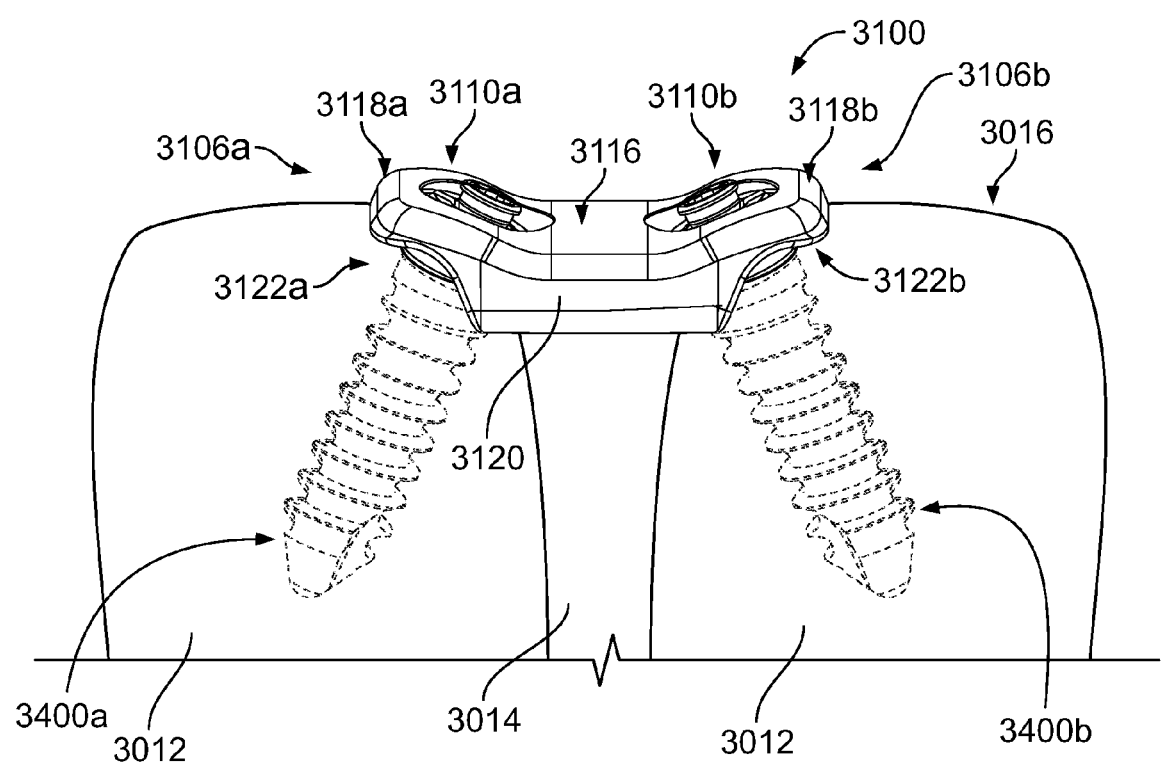
FIG. 55 is a side elevational view of the bone plate system of FIG. 54 showing the bone plate positioned on the corners of two vertebral bodies and partially extending into the intervertebral space.

As shown in FIG. 55, the bone plate 3100 may be positioned on an anterior vertebral surface 3016 between two vertebrae 3012 such that the middle portion 3104 projects partially into the intervertebral space 3014. The bone plate 3100 includes an upper surface 3116 that faces away from the vertebrae 3012 and lips 3118a, 3118b at the ends 3106a, 3106b that are thin and extend over the anterior vertebral surface 3016. In a preferred embodiment, the bone plate 3100 has a sidewall 3120 with undercuts 3122a, 3122b that are configured to conform to the curvature of the adjacent vertebrae 3012.

Figure 56:
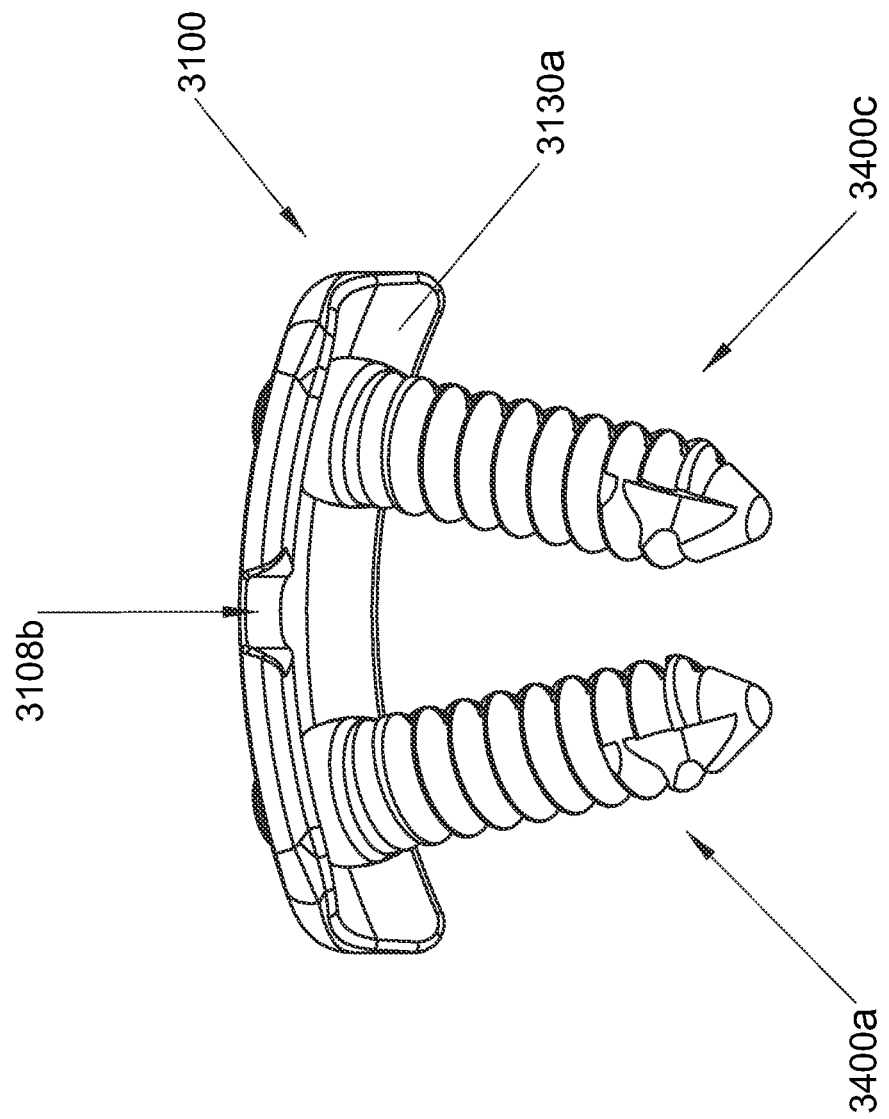
FIG. 56 is a front view of the bone plate of FIG. 54 showing an arcuate surface on the underside of the bone plate.
Figure 57:
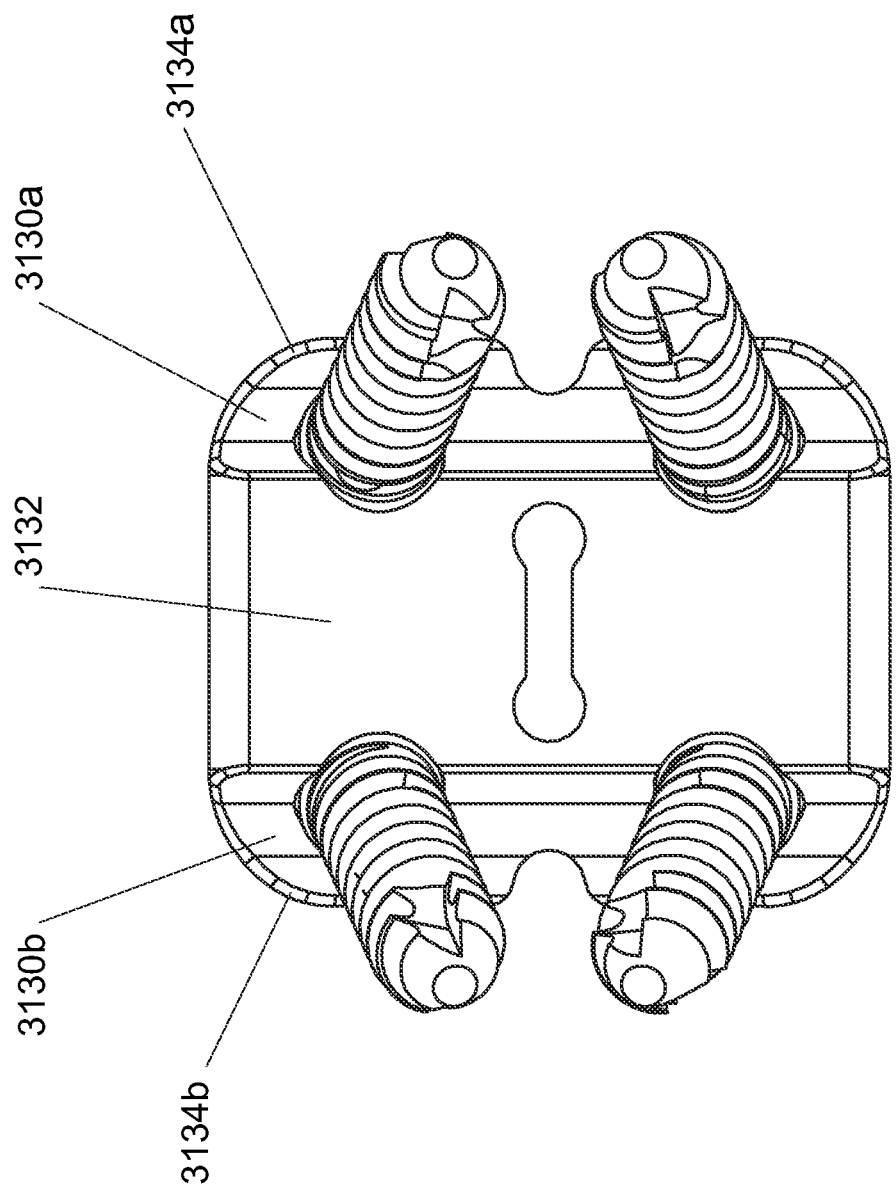
FIG. 57 is a bottom view of the bone plate of FIG. 54 showing arcuate surfaces extending away from a lower surface of the bone plate.
Figure 61:
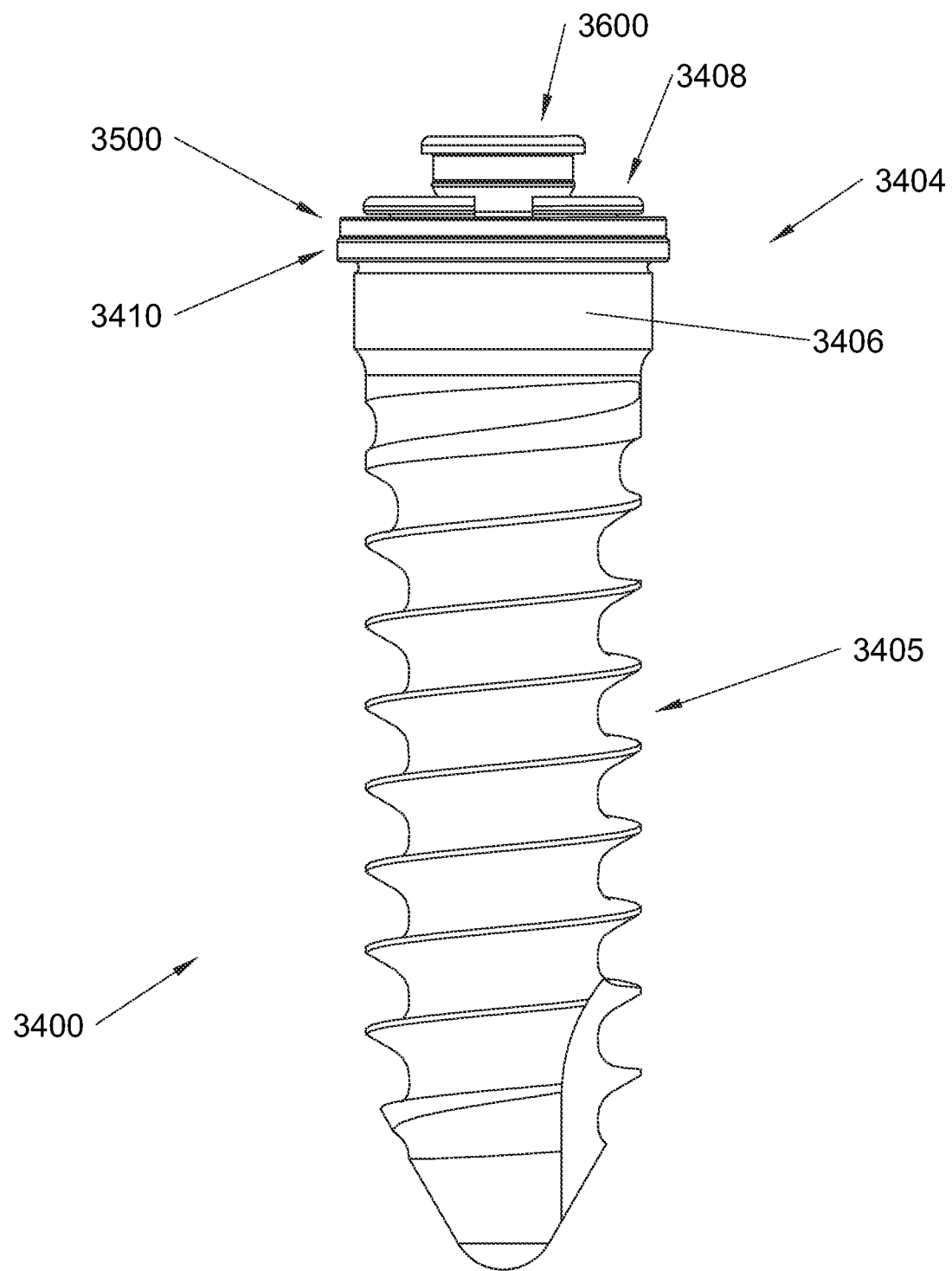
FIG. 61 is a side elevational view of a bone assembly of FIG. 54 showing a locking cap and a locking fastener connected to a bone anchor head portion.

The bone plate 3100 may also be generally curved to conform to the anterior surfaces 3016 or other bone features, as shown in FIG. 56. To receive the end of a bone, the bone plate 3100 may have arcuate surfaces 3130a, 3130b which may seat against a corner of the bone. FIG. 57 presents a bottom view of the bone plate 3100 that shows the arcuate surfaces 3130a, 3130b meeting at a lower surface 3132. Also present on the bone plate 3100 are raised ridges 3134a, 3134b that project away from the respective arcuate surface 3130a, 3130b and may be configured to engage bone surfaces.

The bone plate 3100 preferably includes four bores 3102a, 3102b, 3102c, and 3102d generally defined by respective bore sidewalls 3140a, 3140b, 3140c, and 3140d, as shown in FIGS. 58-60. Each bore sidewall 3140 includes an upper bore surface 3142, a lower bore surface 3144, an annular seating surface 3146, and an arcuate channel 3148. The lower bore surface 3144 has the smallest opening, which restricts the anchor head portion 3404 from passing completely through the bore 3102. The anchor head portion 3404 rests against annular seating surface 3146, so the annular seating surface 3146 is preferably sized larger than the lower bore surface 3144. The upper bore surface 3142a is smaller than the arcuate channel 3148 to restrict back out of the bone anchor assembly 3400 once the locking cap 3500 has expanded within the arcuate channel 3148 to a size larger than the opening defined by the upper bore surface 3142.

The bone anchor assembly 3400 includes a head portion 3404 and a shank portion 3405. The head portion includes a cylindrical outer surface 3406 that is sized to be in tight engagement with lower bore surface 3144 when placed into a through bore 3102. The head portion 3404 also includes projections 3408 that serve to retain the locking cap 3500 on an upper radially extending portion 3410. The shank portion 3405 may be threaded or non threaded, but is preferred to be of a self-tapping bone screw configuration.

Figure 64:
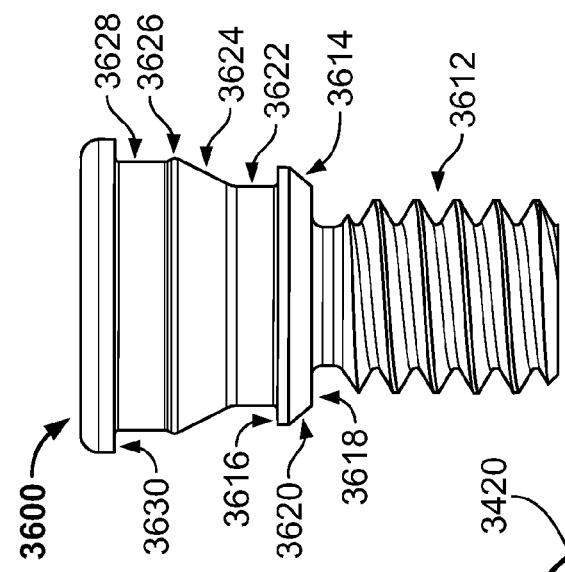
FIG. 64 is a side elevational view of the locking fastener of FIG. 61 showing an annular collar, narrow portion, and radially outer cam surfaces of the locking fastener.
Figure 63:
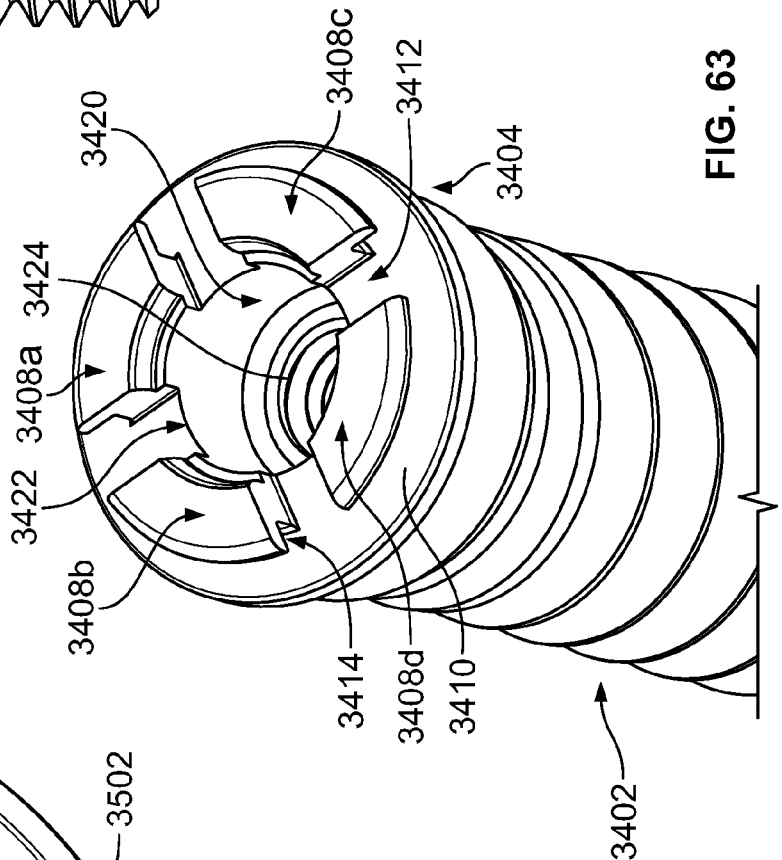
FIG. 63 is a perspective view of the bone anchor of FIG. 61 showing a plurality of projections extending axially upward from an upper radially extending portion of the anchor head.
Figure 62:
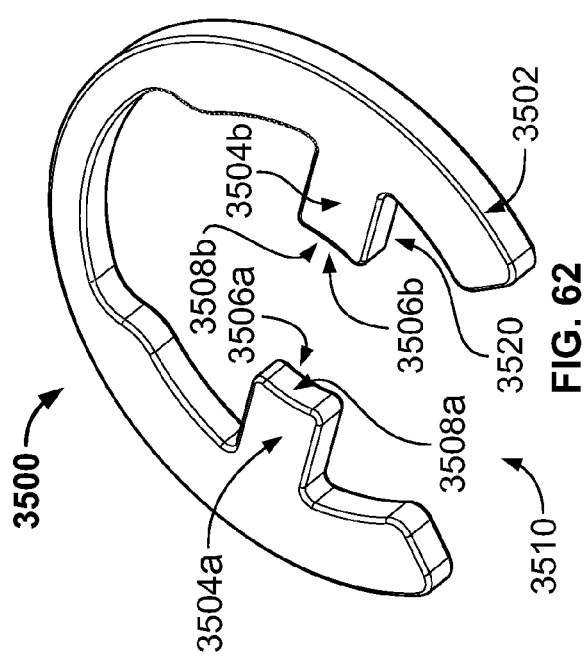
FIG. 62 is a perspective view of the locking cap of FIG. 61 showing projections that extend radially inward from an outer ring.

With reference to FIGS. 62-64, the locking cap 3500 includes an outer ring 3502 and projections 3504a, 3504b that extend radially inward from the outer ring 3502. The projections 3504a, 3504b have radially inner ends 3056a, 3506b and cam surfaces 3508a, 3508b disposed thereon. The outer ring 3502 is generally C-shaped with a gap spacing 3510 between ends thereof.

The bone anchor head portion 3404 carries the locking cap 3500 on the upper radially extending portion 3410 that extends about the periphery of the anchor head portion 3404. As shown in FIG. 63, the anchor head portion 3404 may include four projections 3408a, 3408b, 3408c, and 3408d extending axially upward from the upper radially extending portion 3410. To position the locking cap 3500 onto the anchor head portion 3404, the locking cap gap spacing 3510 is expanded and the locking cap 3500 is translated toward the anchor head portion 3404 and along the longitudinal axis of the bone anchor 3402 until the locking cap projections 3504a, 3504b are received within channels 3412 formed between projections 3408. Then, the locking cap 3500 is released such that the outer ring 3502 resiliently snaps into undercuts 3414 formed in the projections 3408. Also shown in FIG. 63 is an axially extending bore 3420 of the bone anchor 3402. The axially extending bore 3420 is in communication with an opening 3422 at the upper end of bone anchor 3402. In a preferred form, the bore 3420 has a threaded portion 3424.

Once the locking cap 3500 is positioned on the anchor head portion 3404, the locking fastener shank 3612 is advanced into the axially extending bore 3420. In a preferred form, the locking fastener shank 3612 is threaded to engage the threaded portion 3424 of axially extending bore 3420. The locking fastener 3600 has an annular collar 3614 that includes flat upper and lower surfaces 316, 318, as well as a radially extending outer cam surface 3620. As the locking fastener 3600 is axially advanced along the bone anchor head portion 3402, the locking cap cam surfaces 3508 cooperate with the locking fastener outer cam surface 3620 to shift the locking cap projections 3504 radially outward which permits the annular collar 3614 to pass by the projections 3504. With the locking fastener annular collar 3614 axially below the projections 3504, the locking fastener flat upper surface 3616 is in overlapping and confronting relation with a lower surface 3520 of the projections 3504. The bone anchor assembly 3400 is now assembled in such a manner that the locking cap 3500 and locking fastener 3600 are retained on the anchor head portion 3404. The bone anchor assembly 3400 is now ready to be driven into a bone plate bore 3102.

Figure 65:
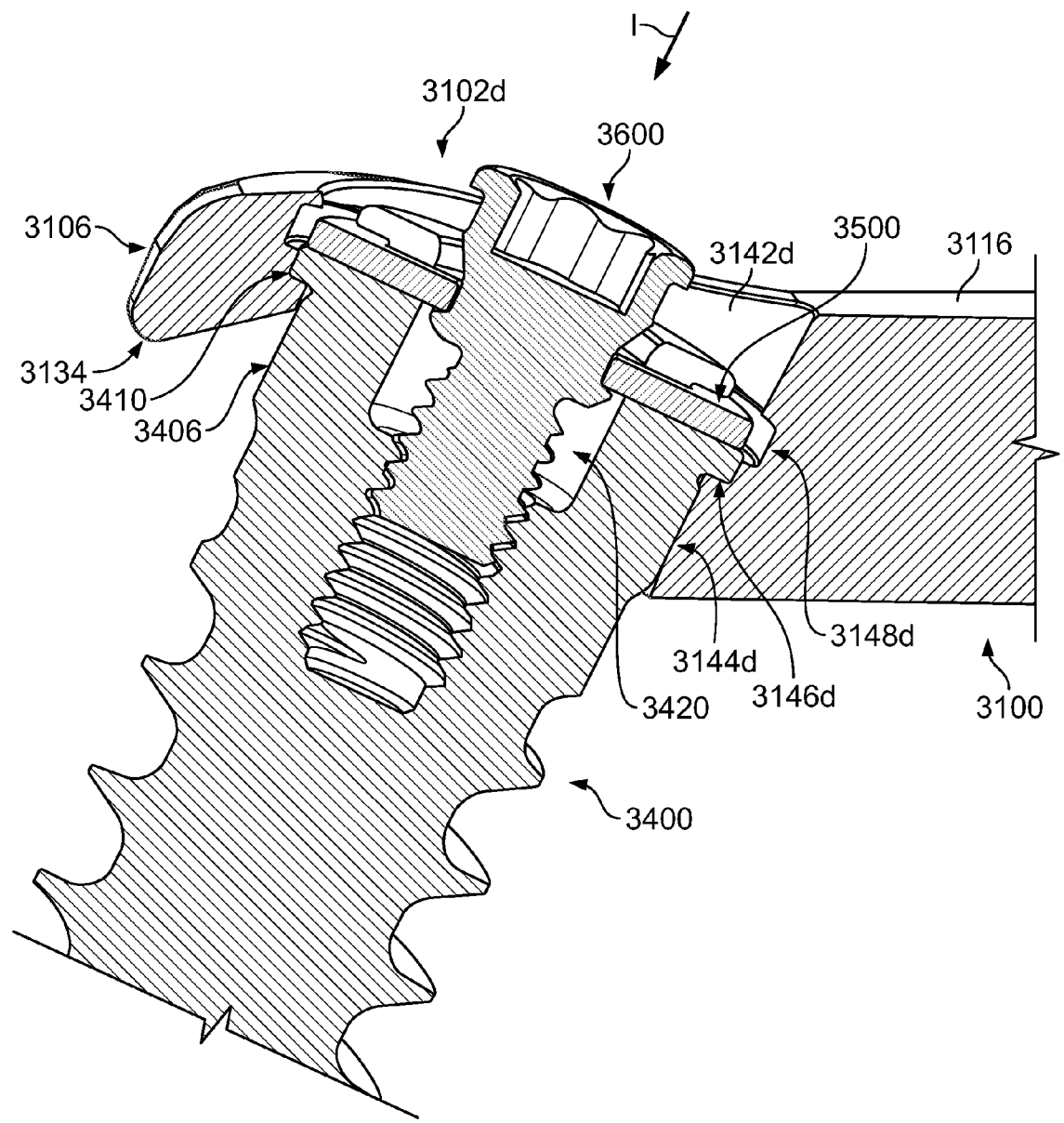
FIG. 65 is a cross sectional view of the bone plate and locking fastener of FIG. 54 showing the bone anchor assembly seated within the bone plate through bore.

With respect to FIGS. 64 and 65, the bone anchor assembly 3400 is driven in direction I into bore 3102d. The bone anchor cylindrical outer surface 3406 is received in close contact with the lower bore surface 3144d such that the lower bore surface 3144d to securely hold the bone anchor assembly 3400 within the bore 3102d. As shown, the bone anchor radially extending portion 3410 is seated against the bone plate annular seating surface 3146d. Further, the locking cap 3500 is substantially aligned with the arcuate channel 3148d. The bone anchor 3400 may be fixed within the bone plate 3100 by driving the locking fastener 3600 in direction I into the axially extending bore 3420.

Figure 66:
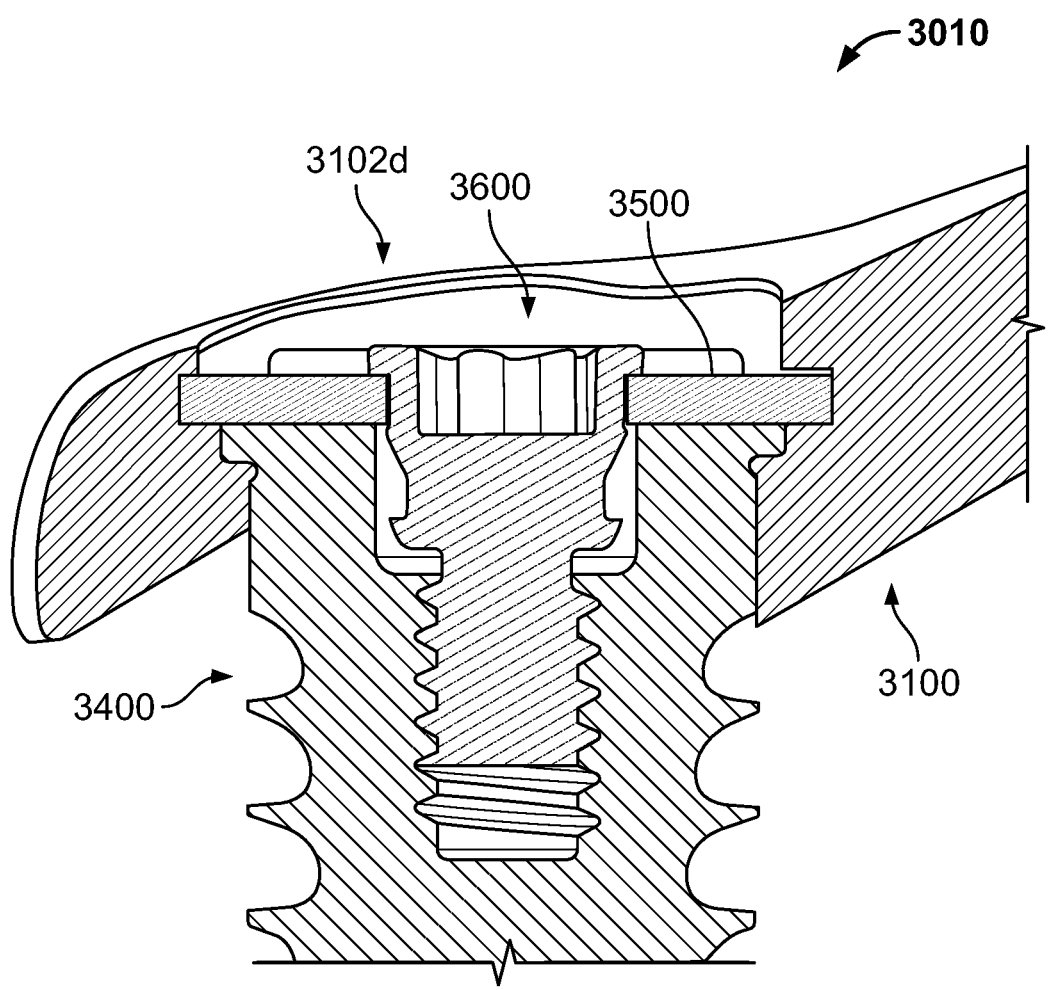
FIG. 66 is a cross sectional view similar to FIG. 65 showing the locking fastener axially shifted into bone anchor to expand the locking collar and fix the bone anchor assembly within the bone plate through bore.

In the preassembled condition, the radially inner ends 3508 are substantially aligned with a narrow portion 3622 of the locking fastener such that the projections 3504 may translate radially inward as needed. Driving the locking fastener 3600 brings a radially extending upper cam surface 3624 of the locking fastener 3600 into contact with cam surfaces 3508 disposed on the projections 3504. This contact shifts the projections 3504 and the outer ring 3502 radially outward. The locking fastener 3600 continues to translate in direction I until projections 3504 pass shoulder 3626 and arrive into contact with an enlarged annular surface 3628. Here, the projections 3504 are forced to remain in their radially extended positions which maintain the locking cap 3500 in the expanded state which resists back out of the bone screw assembly 3400. Additionally, an upper lip 3630 may restrict further movement of the locking fastener 3600 in direction I. FIG. 66 shows the bone plate system 3010 with the bone anchor 3400 fixed within the bone plate 3100.

Figure 67:
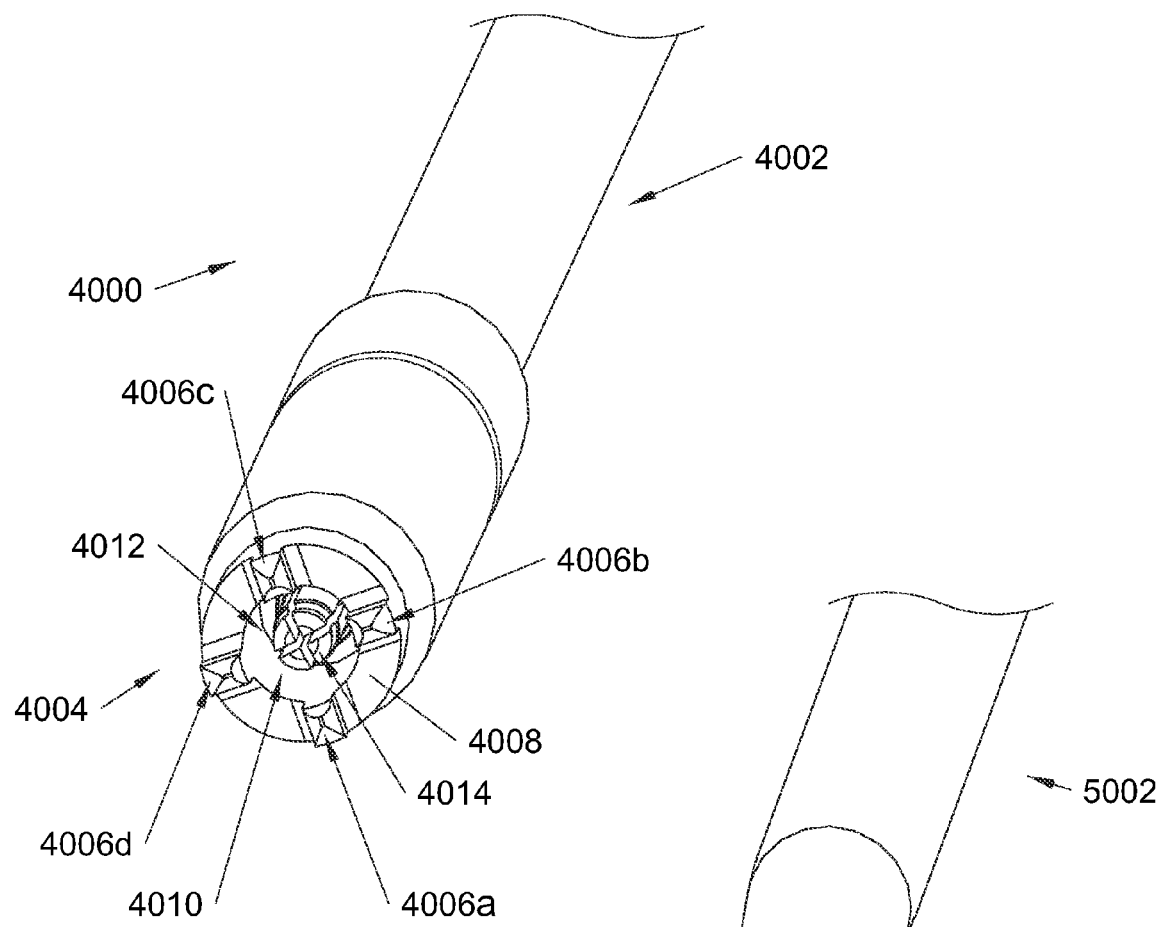
FIG. 67 is a perspective view of a bone anchor driver tool that may be used with the bone plate system.

Several tools associated with the bone plate system embodiments discussed above will now be disclosed. It is contemplated that the tools may be configured to be used in any of the bone plate system embodiments 10, 1010, 2010, and 3010, but features of particular bone plate system embodiments will be used for exemplary purposes. One approach to inserting the bone anchor assembly 1400 involves using a bone anchor driver 4000, as shown in FIG. 67. The bone screw driver has a handle end 4002 and a driver end 4004. The handle end 4002 is preferably a quarter inch square drive configuration adapted to be received within a modular ratcheting T-handle. The driver end 4004 has four prongs 4006a, 4006b, 4006c, and 4006d, which may engage the spaced depressions 1410 on bone anchor head portion 1406. At the base of the prongs 4006 is a flat annular surface 4008 that contacts the locking cap 1500. The driver end 4004 also includes a bore 4010 extending axially along the bone anchor driver 4000 that houses a press fit member 4012. The press fit member 4012 has a plurality of resilient fingers 4014 that are biased radially outward but deflect radially inward when the press fit member 4012 is pressed into a driver bore 1626. The radial bias of press fit member 4012 engages the locking fastener 1600 and the rest of the bone anchor assembly 1400 to the driver end 4004. A user may then drive the bone anchor assembly 1400 through a bone plate bore and into bone.

Figure 68:
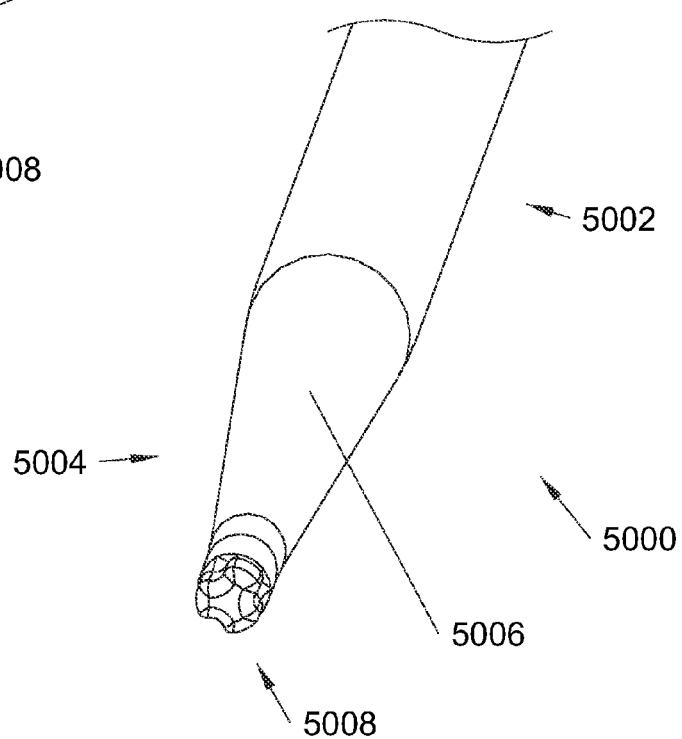
FIG. 68 is a perspective view of a final driver that may be used with the bone plate system.

A final driver 5000 shown in FIG. 68 is used to rotate the locking fastener 1600 and expand the locking cap 1500 to fix the bone anchor assembly 1400 within a bone plate bore. The final driver 5000 has a handle end 5002 and a driver end 5004. The handle end 5002 is preferably connected to a modular torque limiting T-handle to restrict over-tightening of locking fastener 1600. The driver end 5004 includes a tapered portion 5006 that leads to a tri-lobed driver 5008. Alternative driver configurations, such as a hex or other driver may be used.

Figure 69:
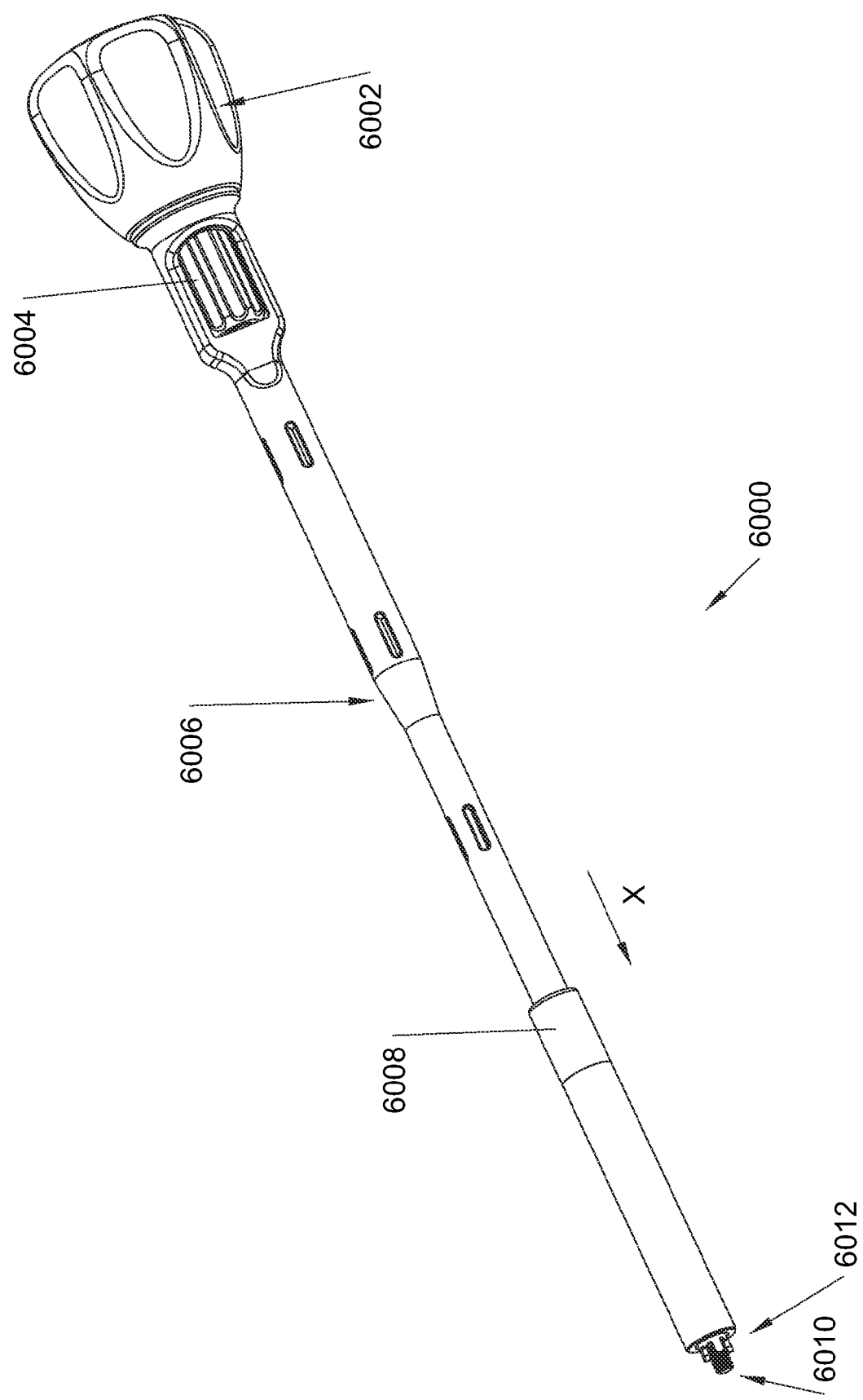
FIG. 69 is a perspective view of a threaded pin inserter that may be used with the bone plate system.

To temporarily hold the bone plate system 10, 1010, 2010, 3010 onto the bone, a self-centering threaded pin inserter 6000 may be used. The pin inserter 6000 includes a handle 6002, a knob 6004, an inner tool shaft 6006, and an outer tool shaft 6008, as shown in FIG. 69. At one end of the pin inserter 6000 is a threaded male end 6010 surrounded by a plurality of fingers 6012. The pin inserter 6000 has an internal spring (not shown) that generally maintains the inner tool shaft 6006 and outer tool shaft 6008 in an expanded configuration, as shown in FIG. 69. However, the inner tool shaft 6006 may be shifted into outer tool shaft 6008 in direction X.

More specifically, the threaded male end 6010 is configured to engage a threaded bore 6108 of a threaded pin 6100, as shown in FIG. 70. The pin inserter fingers 6012 are also sized to fit within depressions 6106 formed in anchor head portion 6102. In an initial preassembled state, the threaded pin 6100 is held within a bore 6204 of a pin cap 6200 by resilient fingers 6202. The pin cap 6200 is received within an opening 6302 formed in a pin centering tip 6300. In the preassembled state, the threaded pin 6100, pin cap 6200, and pin centering tip 6300 are rigidly held together. In an alternative embodiment, the pin cap 6200 and the pin centering tip 6300 may be integrally formed.

As an example, once the bone plate 1100 is in position against a target bone, the pin inserter tool may be used to drive the threaded pin 6100 into the bone to temporarily hold the bone plate 1100 in place. Initially, the threaded male end 6010 is inserted into the head portion 6102 of the threaded pin 6100. Holding the handle 6002 firmly, the knob 6004 is turned clockwise to rotate the threaded male end 6010 and engage the threaded male end 6010 to the pin threaded bore 6108. Once the knob 6004 is fully tightened, the threaded pin 6100, pin cap 6200, and pin centering tip 6300 are firmly attached to the pin inserter 6000.

Next, an arcuate collar 6306 of the pin centering tip 6300 is inserted into bone plate bore 1108 and seated against the bore annular surface 1154d. Preferably, the arcuate collar 6306 is complimentary to the annular surface 1154d such that the arcuate collar 6306 firmly seats therein and is centered within the bore 1108. The pin centering tip 6300 includes slits 6304 formed therein which generally divide the arcuate collar 6306 into portions that may flex relative to one another. In conjunction with a generally curved outer profile of the arcuate collar 6306, this flexibility permits the pin insertion tool 6000 to be adjusted to the desired bone anchor insertion angle.

Once the pin insertion tool 6000 is at the desired bone anchor insertion angle, the handle is shifted in the X direction. As shown in FIG. 71, this movement releases the threaded pin 6100 from the pin cap 6200 and drives the threaded pin 6100 in direction Y through the interior of pin centering tip 6300 and into contact with the underlying bone. To drive the threaded pin 100 to the bone, the user continues to press handle 6002 in direction X and rotates handle 6002 clockwise until the threaded pin head portion 6102 is seated against a narrow portion 6310 of the pin centering tip 6300, as shown in FIG. X. Since the arcuate collar 6306 is centered within the bore 1108 and includes the narrow portion 6310 which defines a central opening 6312 for the threaded pin 6100, the threaded pin 6100 is effectively self-centered within the bone plate bore 1108.

At this point, the threaded pin 6100 has securely pinned the bone plate 1100 against the bone. The force on handle 6002 in direction X is gradually released so that the inner spring may shift the inner tool shaft 6006 back to its initial condition. Knob 6004 is then rotated to disengage the threaded male end 6010 from the threaded bore 6108. Once at least one bone anchor assembly 1400 has been driven into another bore, the threaded pin 6100 may be removed by reversing the procedure. The threaded pin 6100 preferably has a major diameter that is smaller than the major diameter of the bone anchor assembly 1400 so that a bone anchor assembly 1400 may be driven into a bone hole formed by the threaded pin 6100. Further, the threaded pin 6100 preferably has a minor diameter that eliminates the need to re-awl the bone hole before inserting the bone anchor assembly 1400.

While there have been illustrated and described particular embodiments of the present invention, it will be appreciated that numerous changes and modifications will occur to those skilled in the art, and it is intended in the appended claims to cover all those changes and modifications which fall within the true spirit and scope of the present invention.

What is claimed is:

1. A bone plate system for being fastened to one or more bones, the bone plate system comprising:
    a bone plate;
    at least one through bore of the plate having an annular surface extending thereabout;
    an elongate bone anchor for extending through the bone plate bore and driving into a bone, the bone anchor having a longitudinal axis extending between upper and lower ends thereof;
    a non-threaded, rigid upper head portion of the bone anchor and a threaded shank portion depending from the upper head portion which extends from the upper end of the bone anchor, the upper head portion of the bone anchor having a central axial bore including an enlarged diameter upper opening portion thereof that opens to the bone anchor upper end and extends axially downward therefrom;
    a locking cap that is distinct from the elongate bone anchor and is carried on the anchor head portion;
    a locking fastener that is distinct from the bone anchor and the locking cap, the locking fastener being configured to be inserted into the bone anchor bore and movable axially therealong between an unlocked position and a locked position for shifting the locking cap into tight engagement with the bone plate annular surface to keep the anchor fixed relative to the bone plate;
    an upper head portion of the locking fastener configured for driving the locking fastener into the axial bore of the bone anchor and being sized to be received in the upper opening portion of the bone anchor bore;
    an annular wall portion of the locking cap that extends axially along the bone anchor longitudinal axis, the annular wall portion extending about and axially along the bone anchor head portion and being configured to be pivotal relative thereto;
    a radially outer upper end portion of the locking cap annular wall portion configured to engage the bore annular surface;
    a radially inner lower end portion of the locking cap annular wall portion for engaging the bone anchor;
    a radially inner upper cam surface of the locking cap;
    a cam surface of the upper head portion of the locking fastener positioned above the radially inner upper cam surface of the locking cap with the locking fastener in the unlocked position;
    the cam surface of the upper head portion of the locking fastener and the radially inner upper cam surface of the locking cap are configured so that as the locking fastener is moved axially from the unlocked position toward the locked position, the cam surface of the locking fastener cams against the radially inner upper cam surface of the locking cap to deflect and pivot the annular wall portion of the locking cap with the radially outer upper end portion shifting radially outward into tight engagement with the bore annular surface and the radially inner lower end portion shifting radially inward into tight engagement with the bone anchor;
    a plurality of projections of the locking cap extending radially inward from the annular wall portion over the upper head portion of the bone anchor with the radially inner upper cam surface being a plurality of cam surfaces formed on radially inner ends of the projections configured to be cammed against by the cam surface of the upper head portion of the locking fastener to radially translate the projections and deflect the annular wall portion as the locking fastener is moved from the unlocked position toward the locked position;
    an annular collar portion of the locking fastener disposed below the upper head portion thereof;
    wherein the bone anchor, locking cap, and locking fastener are arranged in a preassembled configuration with the locking fastener being inserted in the bone anchor bore at a predetermined axial position so that the annular collar portion is positioned axially below and in confronting relation with the plurality of locking cap projections to resist locking fastener back out from the preassembled configuration thereof.

2. The bone plate system of claim 1 wherein the radially inner lower end portion of the locking cap comprises a plurality of spaced lower circumferentially extending ribs which contract together radially inward toward the bone anchor as the locking fastener cams against the locking cap.

3. The bone plate system of claim 1 wherein the radially outer upper end portion of the locking cap comprises a plurality of spaced upper circumferentially extending shoulders that expand apart radially outward toward the bore annular surface as the locking fastener cams against the locking cap.

4. The bone plate system of claim 1 wherein the annular wall portion has a lower radially raised arcuate outer surface portion configured for engaging the bore annular surface and a radially recessed outer surface portion above the lower arcuate outer surface portion.

5. The bone plate system of claim 4 wherein the annular wall portion has an upper radially raised, arcuate outer surface portion at the radially outer upper end portion thereof configured for engaging the through bore annular surface so that the upper raised outer surface portion and the lower raised outer surface portion are in spaced contact with the through bore annular surface with the recessed outer surface portion spaced from the through bore annular surface.

6. The bone plate of claim 1 wherein the bone anchor rigid upper head portion has an annular channel that extends thereabout below the upper end of the bone anchor and the locking cap radially inner lower end portion is sized and configured to fit in the channel such that the radially inner lower end portion shifts radially inward into the channel as the locking fastener cams the locking cap.

7. A bone plate system for being fastened to one or more bones, the bone plate system comprising:
   a bone plate having at least one through bore and a central axis extending therethrough;
   an elongate bone anchor having a longitudinal axis and being configured for polyaxial insertion through the bone plate bore;
   an upper head portion of the bone anchor configured to be received within the bore;
   a locking cap that is distinct from the elongate bone anchor and is carried on the anchor head portion;
   an annular wall portion of the locking cap that extends axially along the bone anchor longitudinal axis, the annular wall portion extending about and axially along the bone anchor upper head portion with the locking cap carried on the anchor head portion;
   a plurality of projections of the locking cap extending radially inward from the annular wall portion and having radially inner ends;
   a set screw that is distinct from the bone anchor and the locking cap, the set screw being threadingly engaged to the anchor head portion at a predetermined axial position relative thereto and having a narrow portion thereof that is aligned with the projections of the locking cap with the set screw threadingly engaged to the anchor head portion at the predetermined axial position;
   the radially inner ends of the projections being radially spaced from the narrow portion of the set screw to permit the projections to shift radially inward due to contact of the locking cap annular wall portion with the bone plate during insertion of the bone anchor through the through bore at large insertion angles between the bone anchor longitudinal axis and the bore central axis;
   a lower radially enlarged portion of the set screw below the narrow portion thereof that is arranged below the plurality of projections of the locking cap with the set screw engaged to the anchor head portion at the predetermined axial position;
   a radially inner lower end portion of the locking cap annular wall portion that is positioned below the plurality of projections of the locking cap for securely engaging the bone anchor head portion;
   the plurality of projections of the locking cap extend radially inward from the annular wall portion radially beyond the radially inner lower end portion thereof to radially overlap the lower radially enlarged portion of the set screw to resist axial movement of the set screw away from the anchor head portion;
   an upper radially enlarged portion of the set screw above the narrow portion thereof that is arranged above the plurality of projections of the locking cap with the set screw engaged to the anchor head portion at the predetermined axial position, the upper radially enlarged portion of the set screw configured to engage the projections as the set screw is driven into the anchor head portion;
   substantially flat lower surfaces of the projections of the locking cap facing generally axially downward;
   a substantially flat upper surface of the lower radially enlarged portion of the set screw facing generally axially upward;
   a lower surface of the lower radially enlarged portion of the set screw;
   a cam surface extending between the upper and lower surfaces of the lower radially enlarged portion of the set screw, the cam surface being inclined relative to the bone anchor longitudinal axis to be configured to engage the locking cap projections and shift the projections radially outwardly as the set screw is advanced to the predetermined axial position along the bone anchor head portion;
   wherein with the set screw threadingly engaged to the anchor head portion at the predetermined axial position the bone anchor, locking cap, and set screw are in a preassembled configuration with the axially downward facing, substantially flat lower surfaces of the locking cap projections arranged above and in overlapping confronting relation with the axially upward facing, substantially flat upper surface of the set screw lower radially enlarged portion to resist set screw back out from the preassembled configuration thereof.

8. The bone plate system of claim 7 wherein the anchor head portion has a radially outer upper surface and the annular wall portion of the locking cap has a radially inner upper surface separated from the anchor head portion radially outer upper surface by a gap spacing for allowing the locking cap annular wall portion to deflect radially inward as the annular wall portion contacts the bone plate during insertion of the bone anchor through the bone plate through bore at large insertion angles.

9. The bone plate system of claim 7 wherein the upper radially enlarged portion of the set screw includes a cam surface above the locking cap projections with the cam surface tapering radially outward from the set screw narrow portion for camming against the radially inner ends of the projections to shift the projections radially outward and the locking cap into tight engagement with the bone plate as the set screw is driven into the anchor head portion.

10. The bone plate system of claim 7 wherein the lower radially enlarged portion of the set screw is an annular collar with the upwardly facing, substantially flat upper surface disposed thereon.

11. The bone plate system of claim 7 wherein the bone plate includes a bone-facing surface having a lower projection extending therefrom and a seating projection spaced from the lower projection such that the bone plate may be positioned on the L5 and S1 vertebrae with the seating projection resting on the sacral promontory and the lower projection contacting the sacral bone.

12. The bone plate system of claim 7 wherein the locking cap annular wall portion includes a plurality of close-ended slots extending axially therealong to resist separation of the locking cap from the anchor head portion due to contact between the locking cap annular wall portion and the bone plate.

13. A bone plate system for being fastened to one or more bones, the bone plate system comprising:
- a bone plate;
- a through bore of the bone plate having an annular surface extending thereabout;
- an elongate bone anchor for extending through the bone plate through bore and driving into a bone, the bone anchor having a longitudinal axis extending between upper and lower ends thereof;
- a rigid head portion of the bone anchor having a central axial bore, the rigid head portion of the bone anchor extending from the upper end thereof toward the lower end thereof;
- an upstanding wall of the rigid head portion having an axial length and an upper end that extends about an opening that opens to the central axial bore;
- a locking cap that is distinct from the elongate bone anchor and is disposed on the bone anchor head portion, the locking cap having an unlocked configuration wherein the locking cap does not tightly engage the through bore annular surface and a locked configuration wherein the locking cap is radially expanded to tightly engage the through bore annular surface;
- a locking member that is distinct from the bone anchor and the locking cap, the locking member being configured to be connected to the bone anchor head portion and shiftable axially therealong between unlocked and locked positions for shifting the locking cap from the unlocked configuration to the locked configuration which shifts the locking cap into tight engagement with the annular surface of the bone plate through bore;
- an annular wall portion of the locking cap that extends about and axially along the upstanding wall of the bone anchor head portion with the annular wall portion extending axially from the upper end of the upstanding wall axially downward therefrom for substantially the full axial length of the upstanding wall with the locking cap disposed on the bone anchor head portion;
- a radially outer portion of the locking cap annular wall portion configured to engage the annular surface of the bone plate through bore;
- a radially inner cam surface of the locking cap;
- a cam surface of the locking member arranged and configured to cammingly engage the radially inner cam surface of the locking cap as the locking member is shifted to the locked position to cause the annular wall portion to be deflected so that the radially outer portion shifts radially outward into tight engagement with the through bore annular surface thereby shifting the locking cap from the unlocked configuration to the locked configuration thereof;
- a substantially flat retention surface of the locking member extending generally orthogonal to the bone anchor longitudinal axis;
- a substantially flat retention surface of the locking cap extending generally orthogonal to the bone anchor longitudinal axis;
- wherein the bone anchor, locking cap, and locking member are arranged in a preassembled configuration with the locking cap retention surface disposed above and in overlapping confronting relation with the retention surface of the locking member to maintain the preassembled configuration thereof;
- a channel extending about the bone anchor head portion below the opening of the upstanding wall;
- a lower portion of the locking cap annular wall portion spaced axially from the upper end of the upstanding wall; and
- a lower projection of the locking cap that is aligned with the channel of the bone anchor head portion and extends radially inward from the annular wall lower portion toward the channel.

14. The bone plate system of claim 13 wherein the upstanding wall has rotary drive structures for rotary driving of the bone anchor into bone, and the upstanding wall lacks any radial openings or slots extending therethrough.

15. The bone plate system of claim 13 wherein the bone anchor head portion adjacent the channel is solid and lacks any radial through openings therein such that the channel is not in communication with the central axial bore of the bone anchor head portion.

16. The bone plate system of claim 13 wherein the locking cap has a plurality of projections extending radially inward from the annular wall portion with the radially inner cam surface being a plurality of cam surfaces of the plurality of projections which cooperate with the locking member to radially translate the projections and deflect the annular wall portion as the locking member is shifted to the locked position.

17. The bone plate system of claim 16 wherein the plurality of cam surfaces of the plurality of projections of the locking cap taper radially inward along the longitudinal axis of the bone anchor toward the lower end of the bone anchor.

18. The bone plate system of claim 13 wherein the connection between the locking member and the bone anchor head portion comprises a threaded engagement between threads of the locking member and threads of the bone anchor head portion.

* * * * *